US010548895B2

(12) United States Patent
Azzazy et al.

(10) Patent No.: US 10,548,895 B2
(45) Date of Patent: Feb. 4, 2020

(54) **LIGANDS THAT TARGET *PLASMODIUM* SPOROZOITE BINDING SITES ON CD81 AND THERAPEUTIC METHODS USING THEM**

(71) Applicant: American University In Cairo (AUC), New Cairo (EG)

(72) Inventors: Hassan Azzazy, Alexandria (EG); Reem Al-Olaby, Cairo (EG); Rodney Balhorn, Livermore, CA (US)

(73) Assignee: The American University in Cairo, New Cairo (EG)

( * ) Notice: Subject to any disclaimer, the term of this patent is extended or adjusted under 35 U.S.C. 154(b) by 0 days.

(21) Appl. No.: 15/357,760

(22) Filed: Nov. 21, 2016

(65) Prior Publication Data

US 2017/0258792 A1    Sep. 14, 2017

Related U.S. Application Data

(63) Continuation of application No. PCT/US2014/040529, filed on Jun. 2, 2014.
(60) Provisional application No. 62/000,948, filed on May 20, 2014.

(51) Int. Cl.
*A61K 31/513*    (2006.01)
*A61K 31/192*    (2006.01)
(Continued)

(52) U.S. Cl.
CPC .......... *A61K 31/513* (2013.01); *A61K 31/192* (2013.01); *A61K 31/196* (2013.01);
(Continued)

(58) Field of Classification Search
CPC .. A61K 31/192; A61K 31/196; A61K 31/404; A61K 31/405; A61K 31/4545;
(Continued)

(56) References Cited

U.S. PATENT DOCUMENTS

| 4,466,917 | A | * | 8/1984 | Nussenzweig | ....... | C07K 14/445 |
| | | | | | | 530/350 |
| 9,505,812 | B2 | * | 11/2016 | Doolan | ................ | C07K 14/445 |

(Continued)

OTHER PUBLICATIONS

Baldwin et al. (Accession No. 2002:819327, HCAPLUS,Document No. 138:250575, Title: Malarial Dihydroorotate Dehydrogenase; Source: Journal of Biological Chemistry (2002), 277(44), 41827-41834).*

(Continued)

*Primary Examiner* — Sabiha N Qazi
(74) *Attorney, Agent, or Firm* — Oblon, McClelland, Maier & Neustadt, L.L.P.

(57) ABSTRACT

The invention pertains to ligands that bind to CD81 and that inhibit or block *Plasmodium* attachment to CD81, compositions and methods for preventing, inhibiting or treating infection by *Plasmodium* and ligands that target a *Plasmodium* binding site on CD81 and methods of making and using them. A series of ligand binding sites on the large extracellular loop of the open conformation of CD81 have been identified. Several important sites were located in regions identified by mutational studies to be the site of *Plasmodium* binding. Ligands that recognize these sites were identified. Linking together two or three ligands that bind with low or moderate affinities to different structurally unique sites on a target protein were used to generate small molecule ligand conjugates that exhibit very high affinities to their CD81 targets. Hybrid ligand molecules were also designed using fragment-based drug design methods to generate analogs of the ligands that bind more tightly to the protein than the parent compounds. Identification and design of groups of compounds that bind to CD81 for use as therapeutics for treating patients infected by *Plasmodium* and pathogens that interact with CD81. By binding to CD81, these molecules can block 1) *Plasmodium* attachment and (Continued)

entry into cells (infection), especially hepatocytes; 2) block or inhibit inflammatory responses caused by *Plasmodium*, and 3) block or inhibit the induction of other pathologies associated with *Plasmodium* infection.

18 Claims, 34 Drawing Sheets
(22 of 34 Drawing Sheet(s) Filed in Color)

(51) Int. Cl.
| | | |
|---|---|---|
| *A61K 31/196* | (2006.01) | |
| *A61K 31/404* | (2006.01) | |
| *A61K 31/405* | (2006.01) | |
| *A61K 31/4545* | (2006.01) | |
| *A61K 31/496* | (2006.01) | |

(52) U.S. Cl.
CPC .......... *A61K 31/404* (2013.01); *A61K 31/405* (2013.01); *A61K 31/4545* (2013.01); *A61K 31/496* (2013.01)

(58) Field of Classification Search
CPC ... A61K 31/496; A61K 31/513; A61K 47/481
USPC ......................................................... 514/252
See application file for complete search history.

(56) References Cited

U.S. PATENT DOCUMENTS

| | | | |
|---|---|---|---|
| 2003/0032787 A1* | 2/2003 | Lanar | C07K 14/445 536/23.1 |
| 2017/0258792 A1* | 9/2017 | Azzazy | C07K 14/70596 |

OTHER PUBLICATIONS

Guirgis, Bassem et a. (Analytical and Bioanalytical ChemistryJan. 2012, vol. 402, Issue3, pp. 1019-1027 | Cite asGold nanoparticle-based fluorescence immunoassay for malaria antigen detection).*

Meyer-Ilse, W et al (Abstract, HCAPLUS,1999:248434,DN:131:70496,Title: X-ray microscopy in Berkeley, X-Ray Microscopy and Spectromicoscopy, Status Report from the International Conference, 5th Wuerzburg, Germany, Aug. 19-23, 1998, meeting Date 1996, 422-43; Editor(s): Thieme, Juergen. Conference, General Review).*

Glockner Gernot et al. (Current Biology, vol. 24, Issue 1, Jan. 6, 2014, pp. 11-18. The Genome of the Foraminiferan Reticulomyxa filosa)Electronic Publication Date: Dec. 12, 2013 Journal code: 9107782. E-ISSN: 1879-0445. L-ISSN: 0960-9822).*

Yoon, Ji-Ung et al. (AN 2017:624783, HCAPLUS,DN 166:493187,ABstract of Korean Patent KR 1725756, Title:Separation method of olefin and paraffin using skeleton type organic-inorganic hybrid nanoporous materials).*

Li, Xingjun et al. (STN AN 2016:286361 HCAPLUS, DN166:405110, Two microporous metal-organic frameworks constructed, CrystEngComm (2016), 18(13), 2239-2243, CODEN: CRECF4; ISSN: 1466-8033).*

Urbain et al. (J Control Release. Mar. 10, 2014;177:84-95. doi: 10.1016/j.jconrel.2013.12.032. Epub Jan. 7, 2014).*

Tarantola et al. (Scand J Infect Dis. 2005;37(2):131-40).*

Baldwin et al. (Accession No. 2002:819327, HCAPLUS,(Abstract) Document No. 138:250575, Title: Malarial Dihydroorotate Dehydrogenase; Source: Journal of Biological Chemistry (2002), 277(44), 41827-41834).*

* cited by examiner

FIG. 3B

| Ligand (NCI #) | Binding by SPR (RU) |
|---|---|
| 7962 | 74 |
| 30930 | 70 |
| 40614 | 114 |
| 73735 | 440 |
| 75866 | 40 |
| 87504 | 215 |
| 90444 | 13 |
| 93033 | 11 |
| 98026 | 59 |
| 281816 | 64 |

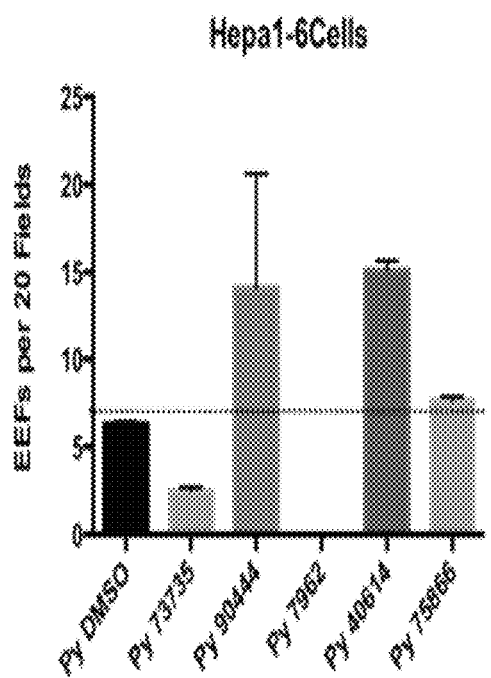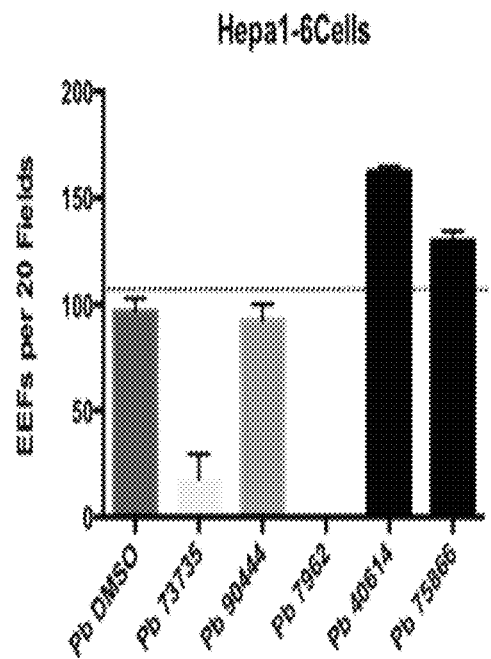

HepG2-CD81

Pf & HepG2-CD81

Lowest free energy conformer
Cluster 35, Rank 1
ΔG = -8.03

Cluster 23, Rank 0
ΔG = -8.07

Cluster 7, Rank 7
ΔG = -7.19

Cluster 30, Rank 2
ΔG = -6.71

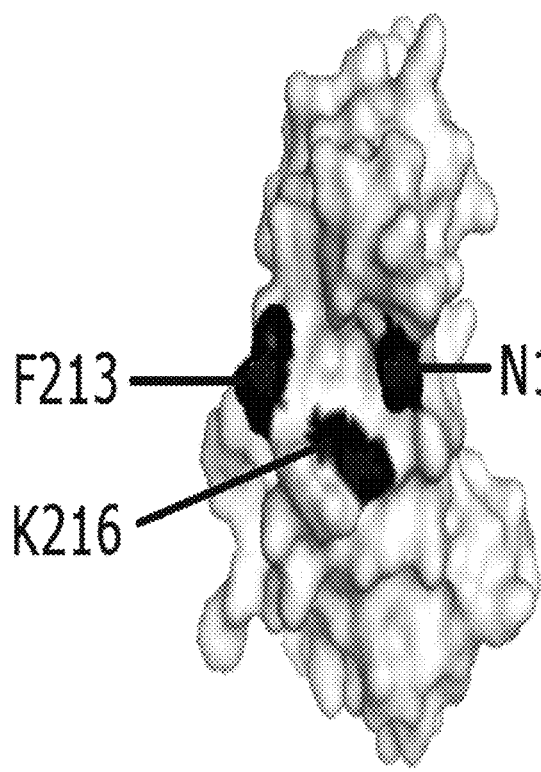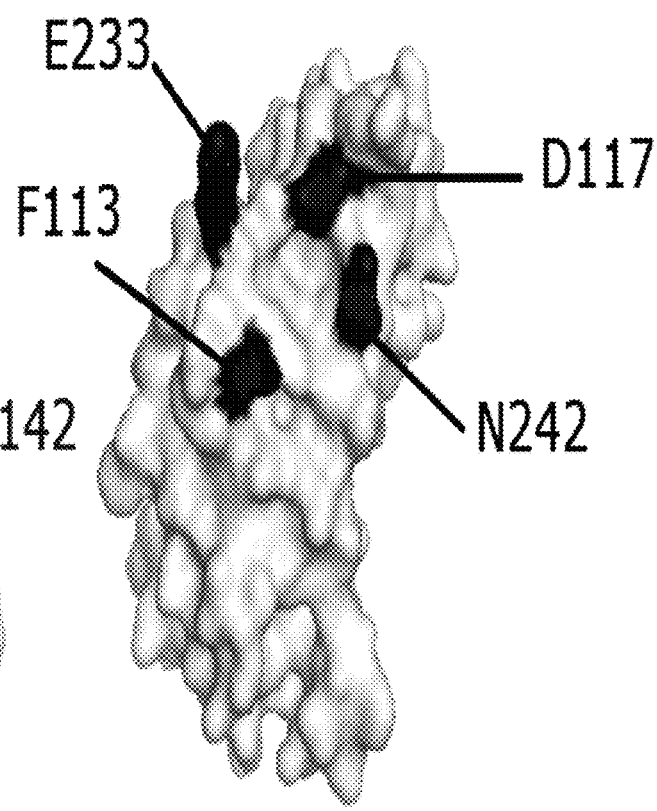
FIG. 9A  SITE 1
FIG. 9B  SITE 2

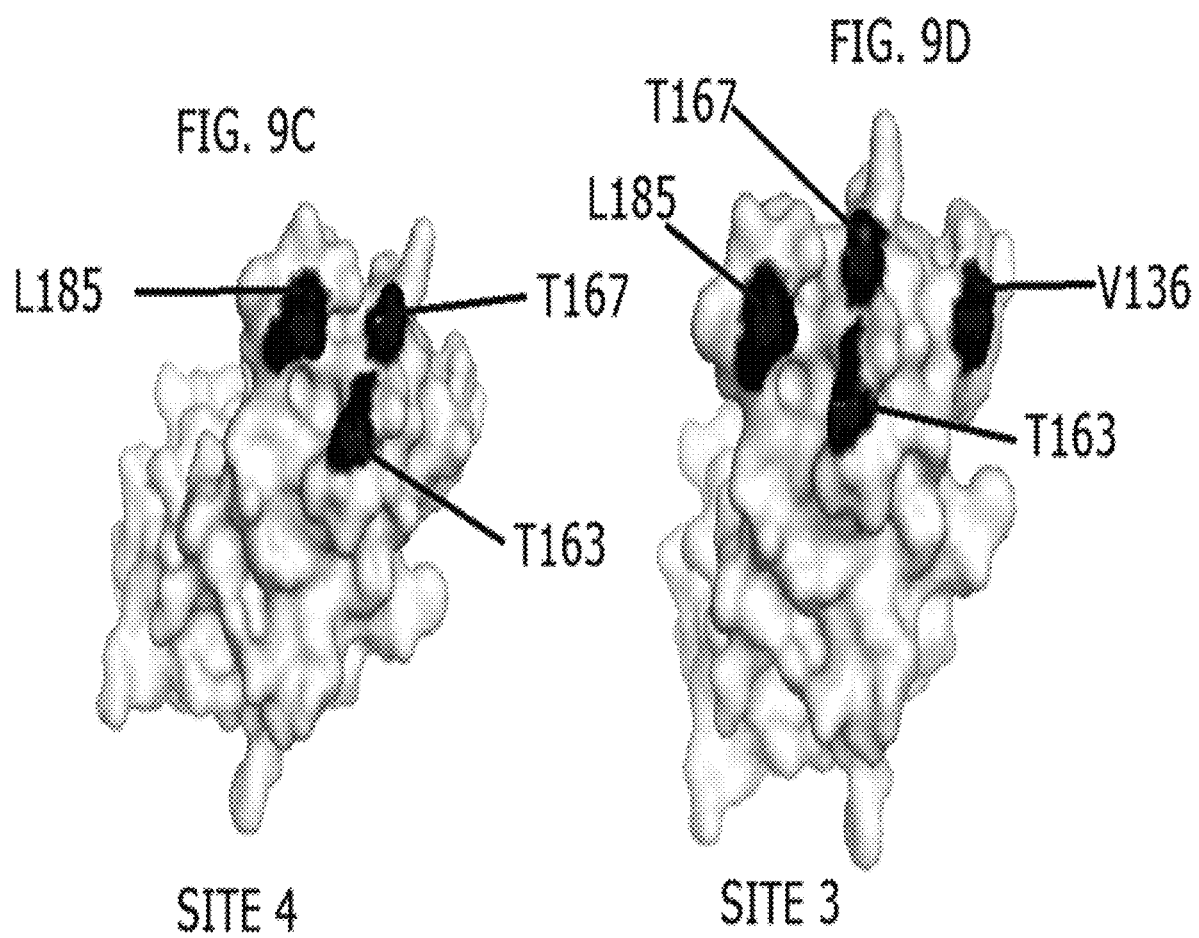

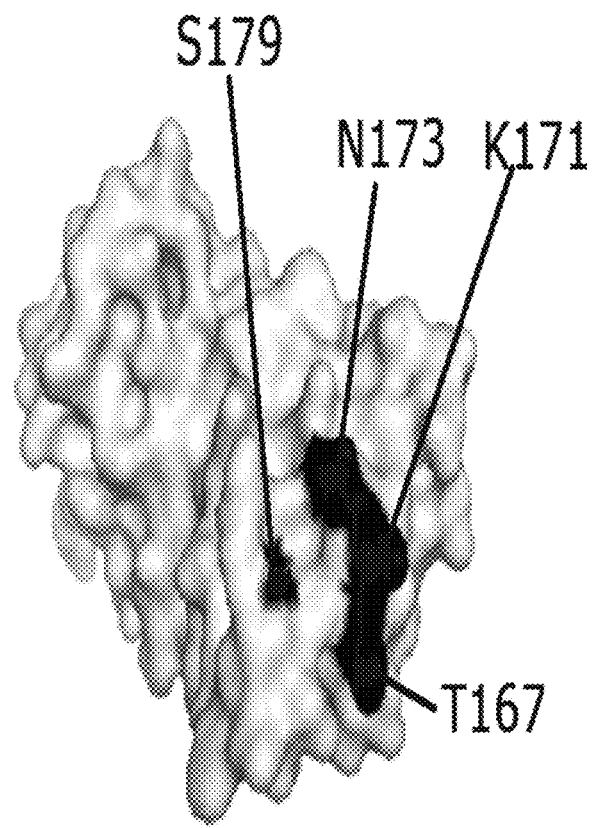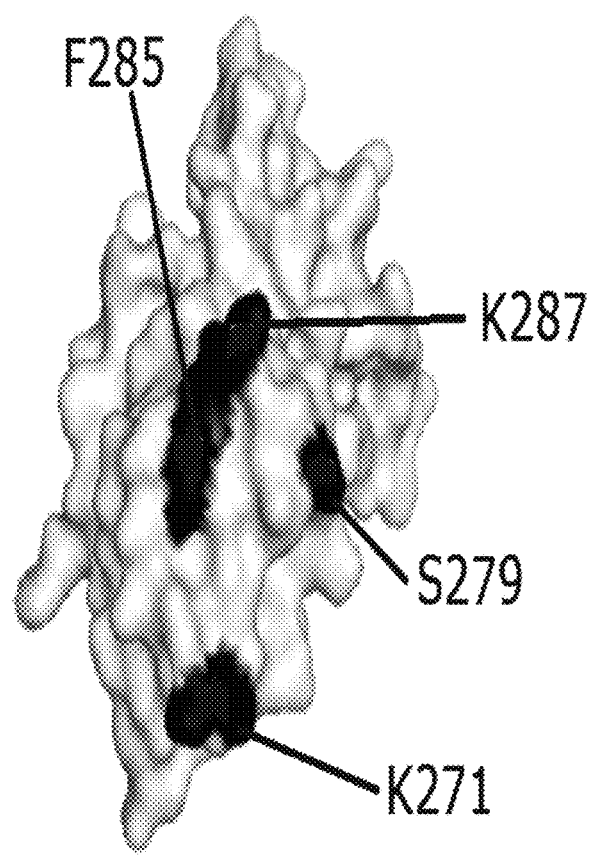
FIG. 9E SITE 5
FIG. 9F SITE 6

SITE 7  SITE 8

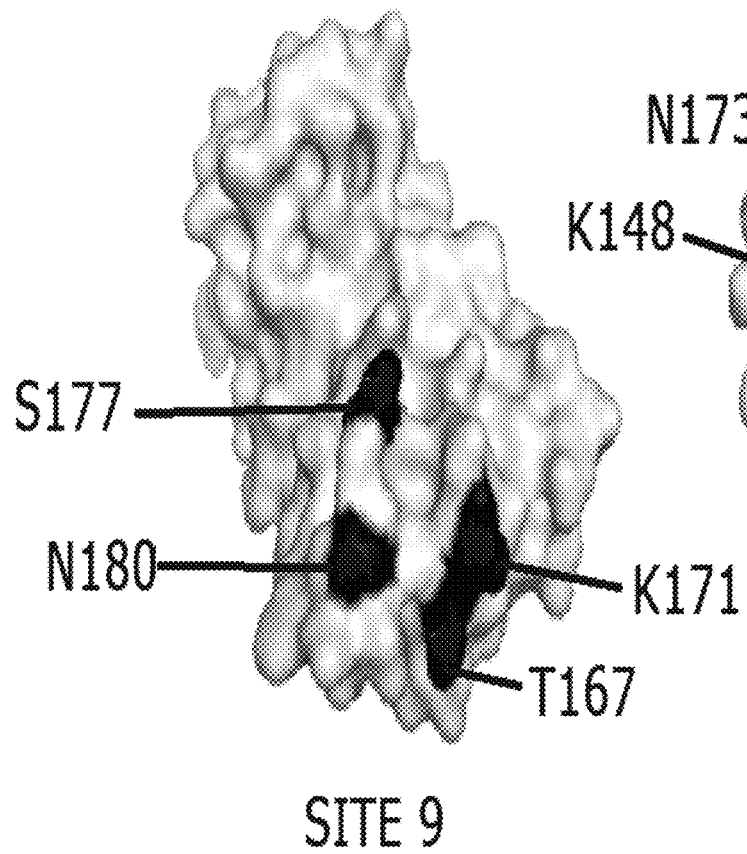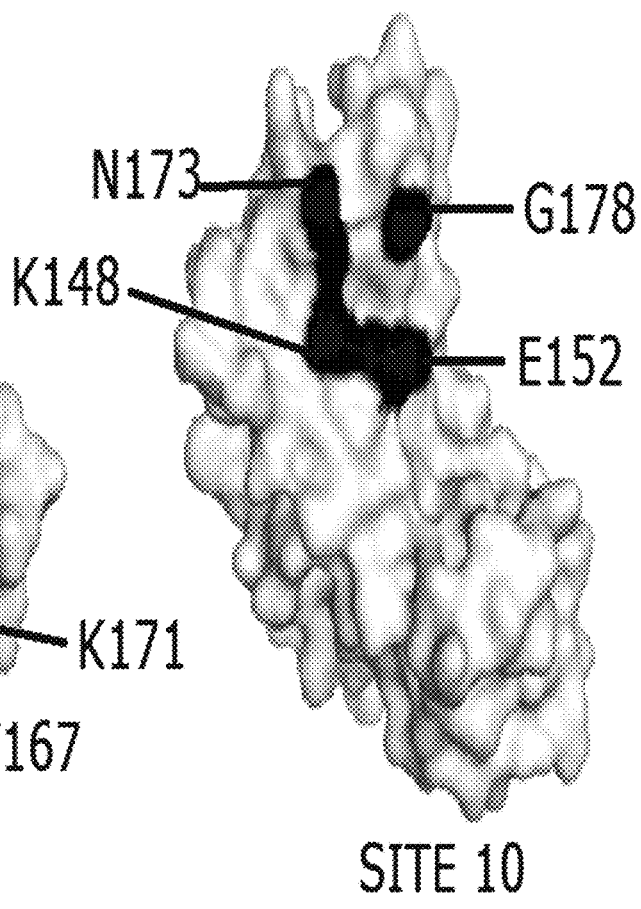
FIG. 9I SITE 9
FIG. 9J SITE 10

281816 Plus 73735 Fragment A

73735 Plus 281816 Fragment

FIG. 11D
281816 Plus 73735 Fragment B
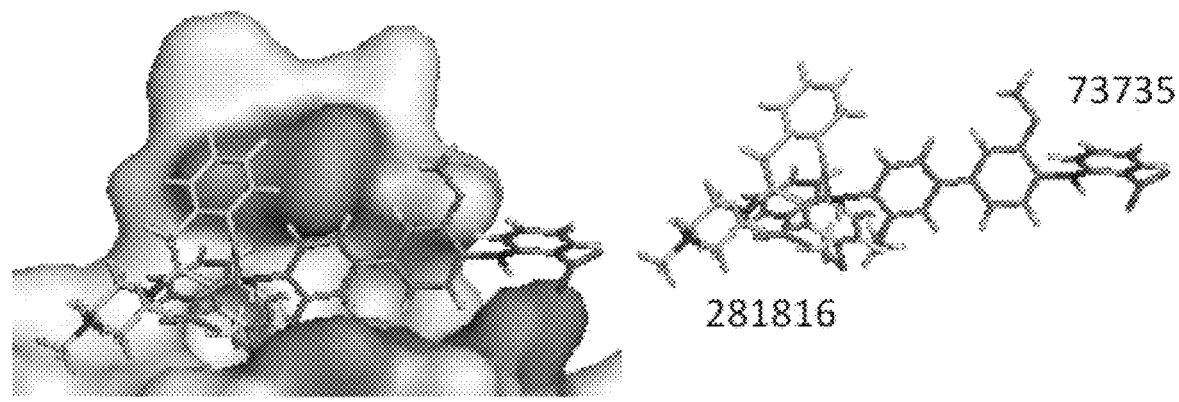
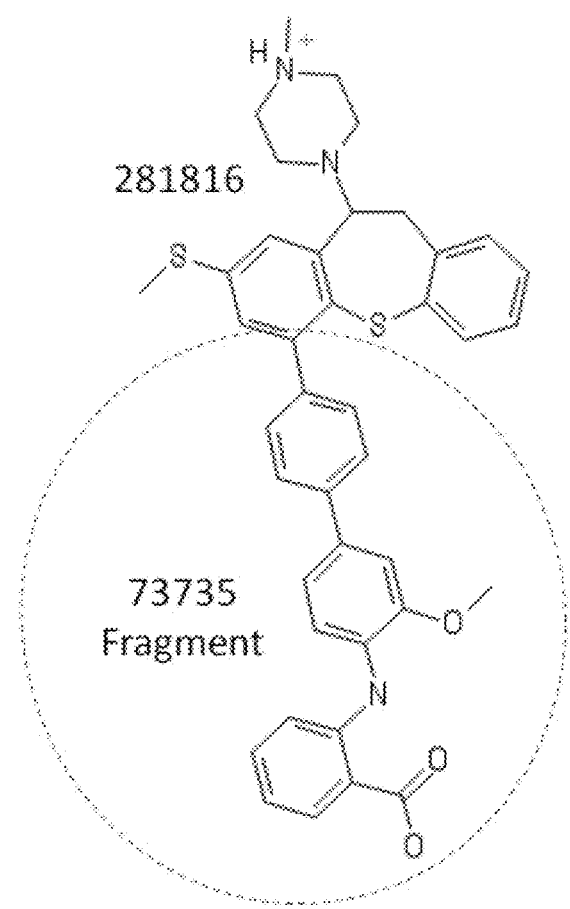

281816 Plus 7962 Fragment

281816 Plus 7962 Fragment

FIG. 11G
281816 Plus 30930 Fragment
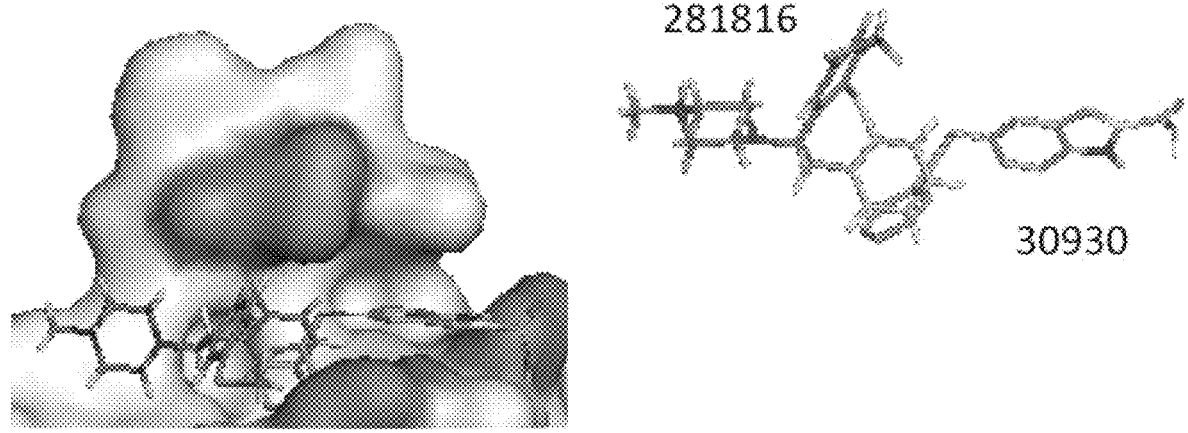
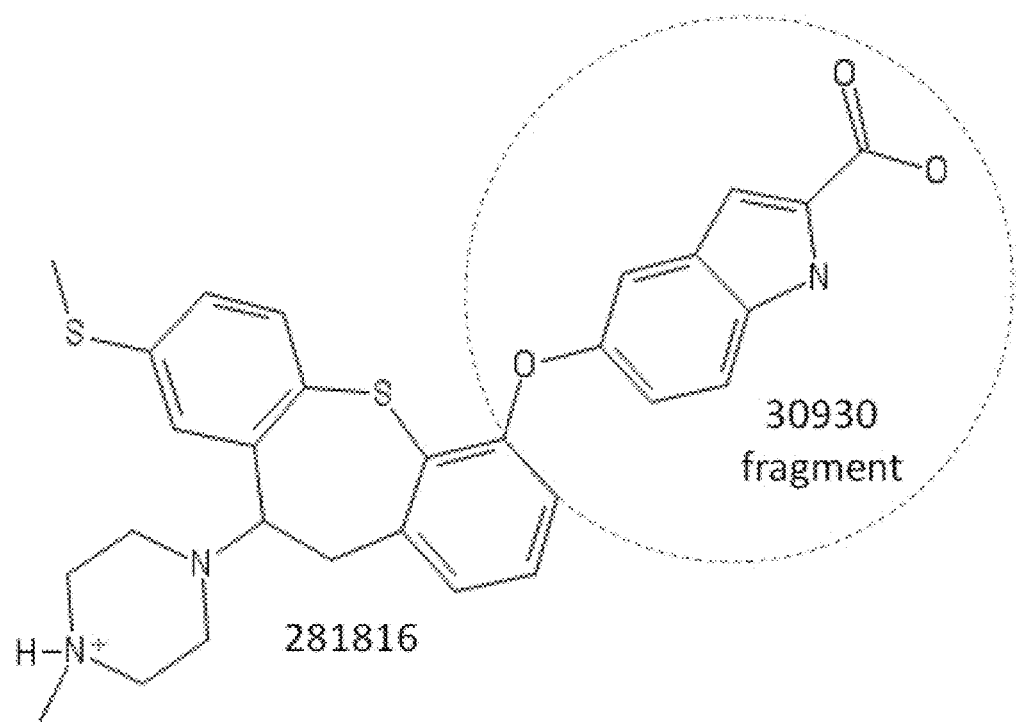

FIG. 11H
281816 Plus 98026 Fragment
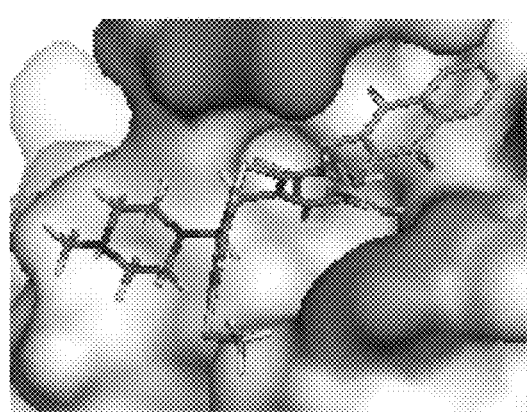
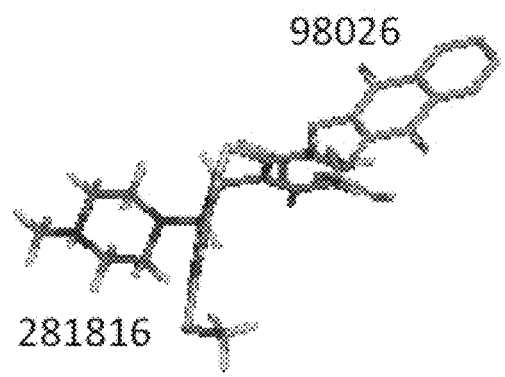
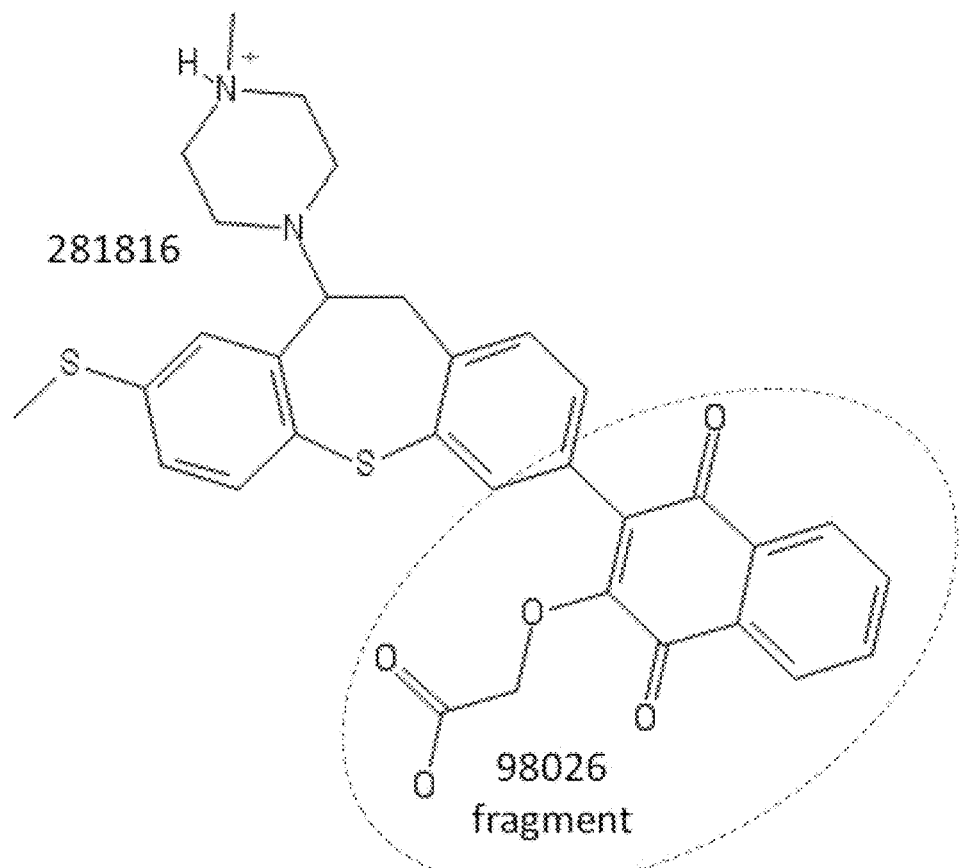

FIG. 11I
281816 Plus 75866 Fragment
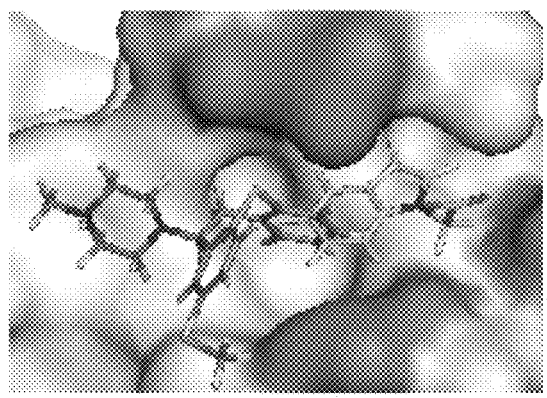
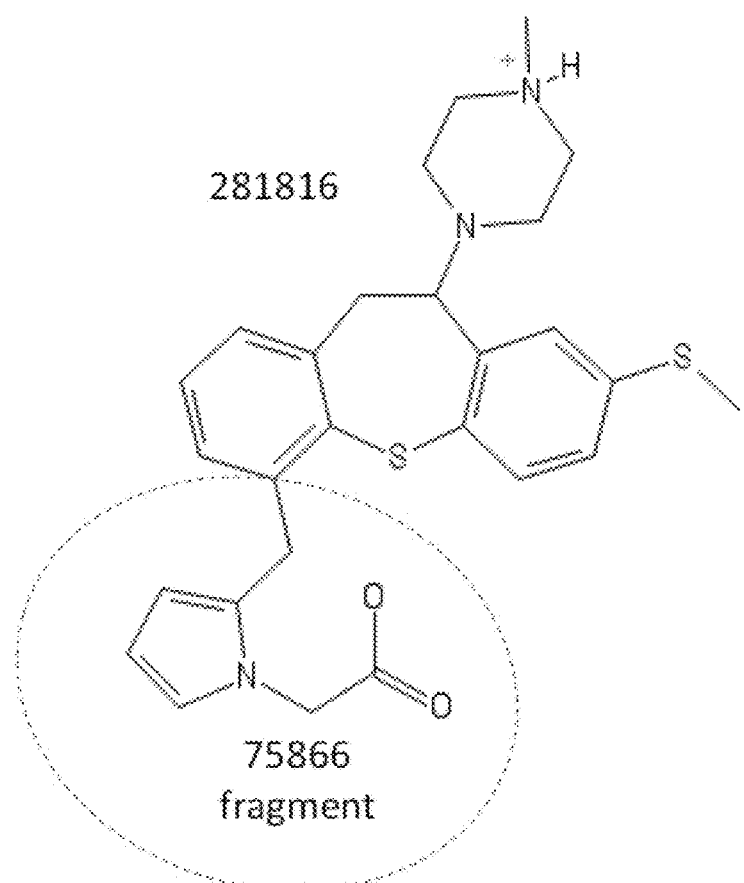

FIG. 11J
7962 Plus 281816 Fragment A
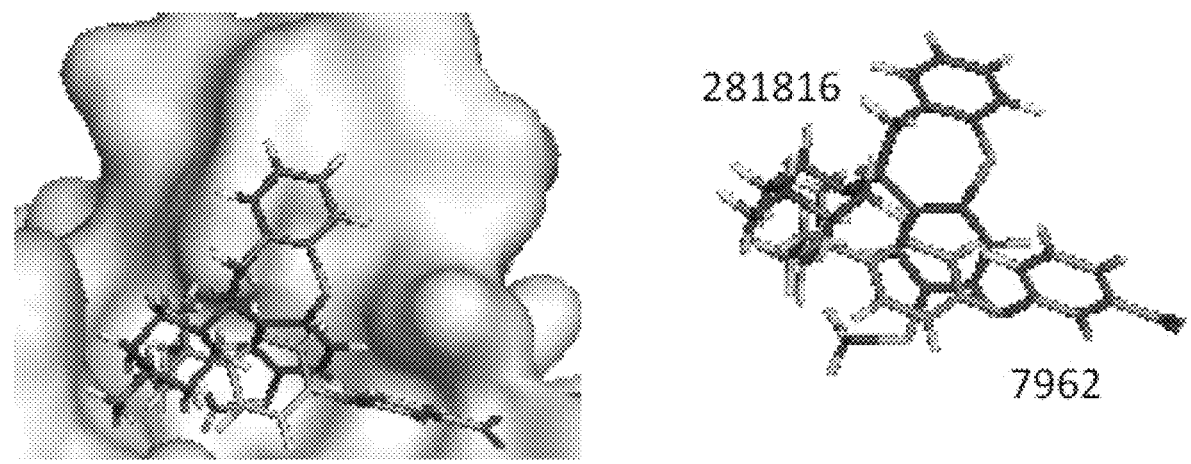
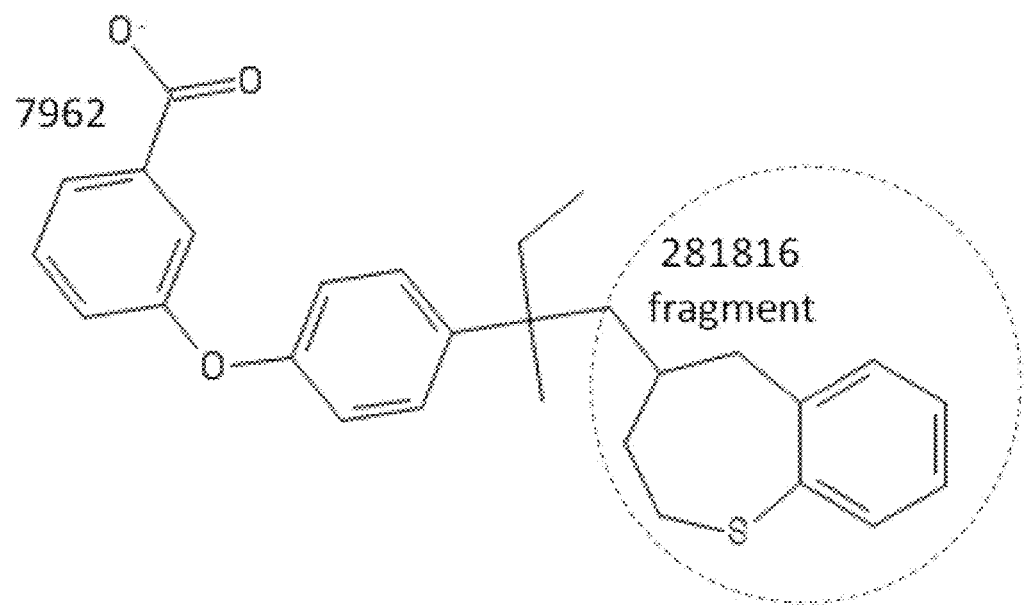

7962 Plus 281816 Fragment B

73735 Plus 7962 Fragment

73735 Plus 40614 Fragment

FIG. 11N
7962 plus 90444 Fragment
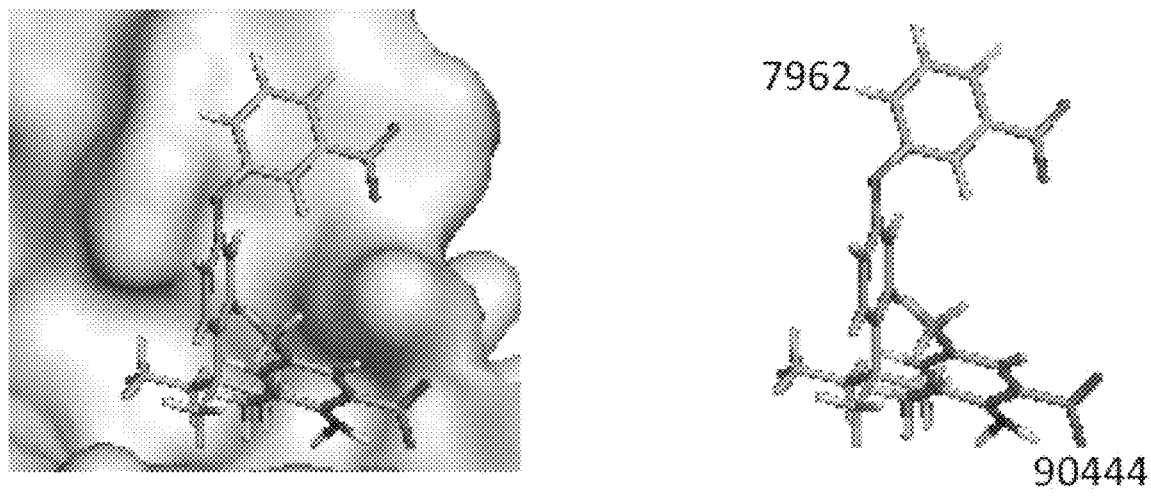
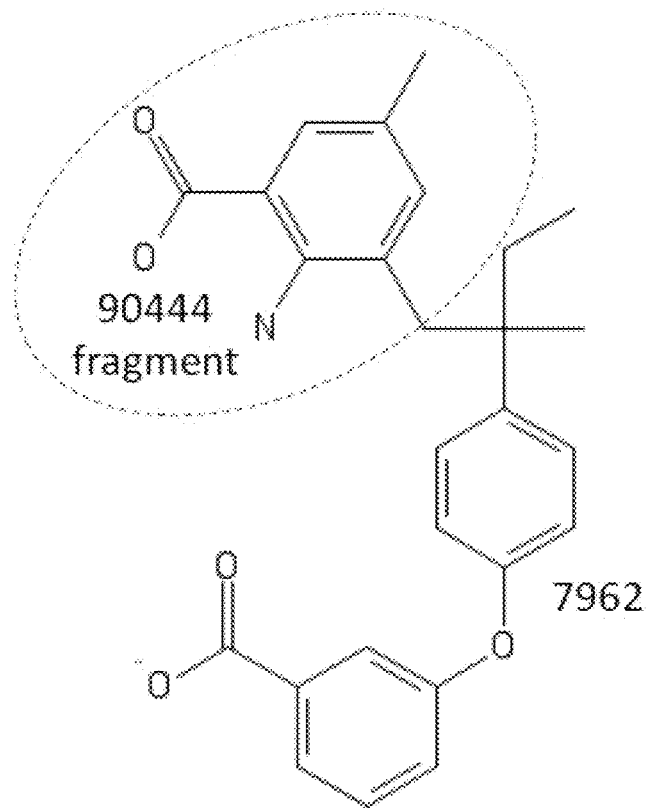

FIG. 11O
281816 plus 90444 Fragment
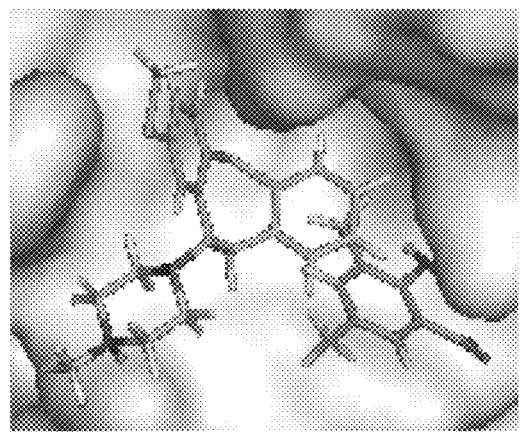
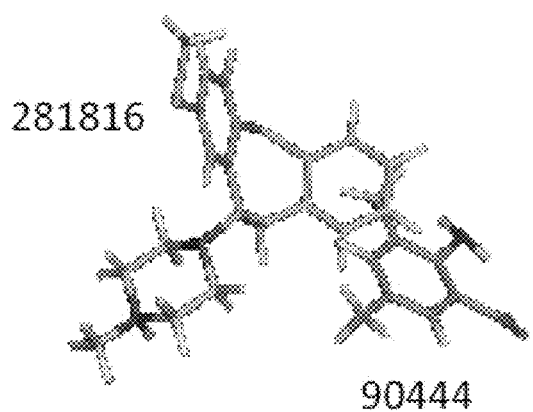
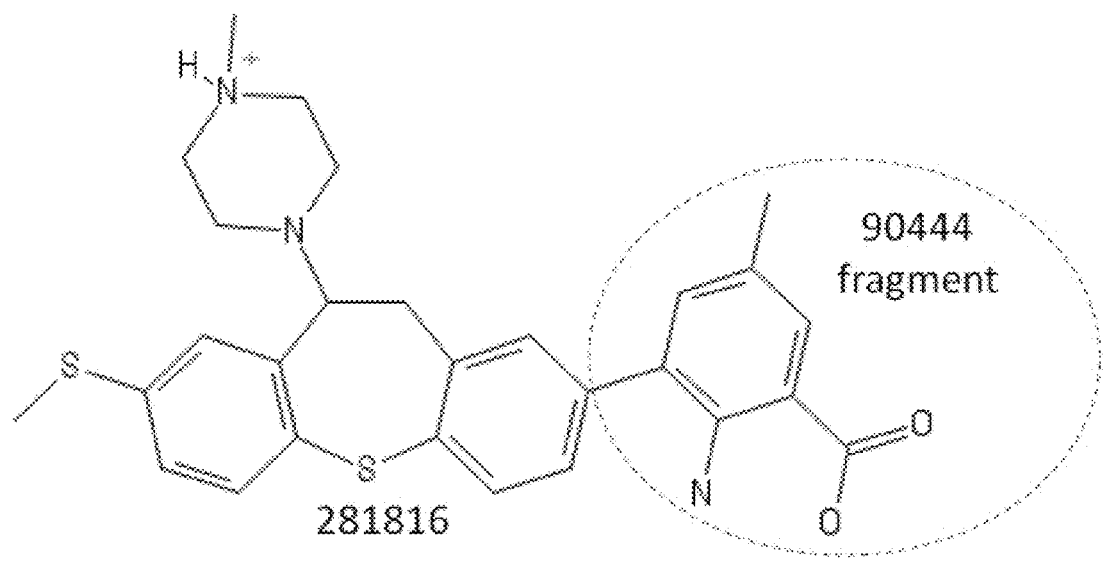

FIG. 13
| \multicolumn{5}{c}{Example Fragment Table} |
|---|---|---|---|---|
| 1 | 2 | 3 | 4 | 5 |
|  | 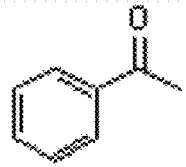 |  |  |  |
| No (0) | Yes (1) | No (0) | Yes (1) | No (0) |
| 6 | 7 | 8 | 9 | 10 |
|  |  | 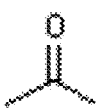 |  |  |
| Yes (1) | Yes (1) | Yes (1) | Yes (1) | Yes (1) |

LIGANDS THAT TARGET *PLASMODIUM* SPOROZOITE BINDING SITES ON CD81 AND THERAPEUTIC METHODS USING THEM

CROSS-REFERENCE TO RELATED APPLICATIONS

This application claims the benefit of U.S. Provisional Application No. 62/000,948, filed May 20, 2014. Cross-reference is also made to PCT/US2013/071056, filed Nov. 20, 2013 entitled "LIGANDS THAT TARGET HCV-E2 BIDING SITES ON CD81 AND THERAPEUTIC METHODS USING THEM". Both of the applications above are incorporated by reference in their entireties.

BACKGROUND OF THE INVENTION

Field of the Invention

Small molecule ligands that bind to sites on the large extracellular loop of human CD81 were identified using structure-based methods. Ligands that block or interfere with attachment, invasion and infection of cells by *Plasmodium* parasites were produced and identified. Conjugates of these ligands were made by linking together two or more of these ligands or their CD81-binding moieties. Such conjugates can bind to different sites on CD81 and exhibit a greater specificity and a higher affinity for CD81 that can the individual ligands. These ligands and ligand conjugates can inhibit the binding of *Plasmodium* or inhibit the interaction of *Plasmodium* with host cells expressing CD81, such as human hepatocytes.

Description of the Related Art

Malaria, a disease transmitted by the *Anopheles* mosquito vector, has been a subject of research interest since the 1880's and remains one of the most important global diseases. Malaria caused by *Plasmodium falciparum* has existed for 50,000-100,000 years but the incidence of human malaria infection likely increased about 10,000 years ago with the adoption of agricultural methods associated with pooled water where mosquitos breed (1). Malaria antigen has been detected in skin and lung samples of Egyptian mummies in 3200 and 1340 BC (5, 6). The causative agent of malaria was discovered by a scientist called Laveran who discovered it in 1884 after examining the blood smears from infected patients (2, 3). In 1898, Scottish physician Sir Ronald Ross revealed the complete life cycle of malaria and proved its vector was a mosquito. In 1902 he was awarded the Nobel Prize based on his work (4).

Malaria is caused by protozoan parasites belonging to the genus *Plasmodium*. Human malaria infection is commonly caused by four different species which are *Plasmodium malariae, Plasmodium ovale, Plasmodium vivax* and *Plasmodium falciparum*, with *P. falciparum* and *P. vivax* being the predominant global species causing malaria (7).

Malaria infection is initiated by the introduction of the parasite into a human by mosquito bites and subsequent invasion of the sporozoite stage of the parasite into the hepatocytes (liver stage) which release the merozoite state of the parasite which invades red blood cells (blood stage), Hepatocytes express CD81 a determinant used by the malaria parasite to invade them. In order for *Plasmodium* parasites to propagate in the host and establish an infection, they are internalized into the hepatocytes (8). The mechanism of interaction of *Plasmodium* sporozoites with hepatocytes is still not clear however, human CD81 was found to be one of the significant surface proteins on the hepatocytes required by the sporozoites to invade the liver cells (9-11).

CD81 belongs to the tetraspanin family. It possesses or confers functions such as cell adhesion, migration, cell fusion, co-stimulation, signal transduction, and differentiation (12). CD81 silencing by anti-CD81 antibodies substantially inhibits the infection of hepatocytes by *Plasmodium falciparum* sporozoites. Additionally, it was found that *Plasmodium yoelii* sporozoites do not have the ability to infect CD81-deficient mouse hepatocytes both in vitro and in vivo (9-11).

Yalaoui et al. (13) identified specific amino acid residues in CD81 that are important for *Plasmodium* infection by conducting mutational studies. They found a stretch of 21 amino acid residues were required for invasion (135-VVDDDANNAKAVVKTFHETLD-155) (FIG. 1) (13) (SEQ ID NO: 5). Despite many prior advances there remains a profound need for new ways to prevent and treat malaria.

BRIEF SUMMARY OF THE INVENTION

The inventors have identified several small organic molecules that inhibit the attachment of *Plasmodium* parasites to CD81, a cellular determinant on the host cells infected by *Plasmodium* parasites. Several different methods were employed to identify and characterize these small organic molecule ligands for CD81 and to test their ability to inhibit *Plasmodium* attachment or interaction with CD81 and CD81-bearing cells. The inventors further characterized these small molecules by determining their binding affinities for CD81 or to cells expressing CD81 or their ability to block the attachment of other ligands to CD81 in vitro or in vivo are described herein. Compositions suitable for administering these small molecule ligands to subjects exposed to malaria parasites or at risk of exposure, or those infected with malaria parasites are disclosed as are methods for prophylaxis and treatment of malaria infection.

Using computational docking and virtual screening methods, the inventors have identified a group of small organic molecules—ligands for CD81 —that bind to different sites on CD81 and which inhibit the attachment or interaction of *Plasmodium* parasites with CD81 or CD81-bearing cells. These small molecules bind to different parts of the CD81 molecule and one aspect of the invention is the identification of ligands that bind to these different sites, including Sites 1-10 described by FIG. 9.

The inventors have identified small molecule ligands that inhibit or block *Plasmodium* binding to CD81 in vitro and disclose assays that validate small molecule ability to inhibit the binding of *Plasmodium* and other pathogens, such as HCV. An aspect of the invention is the use of small molecule ligands, structural analogs of the ligands, and ligand conjugates, to inhibit the binding of *Plasmodium* and other microbial pathogens to CD81 or to modulate CD81 interaction with other ligands or receptors. Such assays may be used to select small molecule ligands that bind to CD81 to inhibit the attachment of a particular species or kind of malaria parasite to a host cell. A particular small molecule can be customized or selected to treat infection by a particular kind of *Plasmodium* parasite or other microbial pathogen, for example, by selecting one that preferentially inhibits that strain so that the effective dosage administered to a subject is reduced and the subject experiences reduced side-effects or drug toxicity. Alternatively, to provide a broader activity spectrum, cocktails of different small molecule inhibitors can be produced that include small molecule inhibitors that modulate or block binding of a variety of

*Plasmodium* or other microbial pathogens; especially those endemic in a particular geographical area or population segment.

The inventors also disclose ligand conjugates of a small molecular ligand or a fragment of it that binds to CD81 and other CD81 ligands. This often produces a molecular conjugate having a higher affinity for CD81 that either of the individual ligands. More complex ligand conjugates that bind to three, four or more sites on CD81 may be constructed. These conjugates are used to more effectively inhibit the binding of *Plasmodium* parasites and other pathogens to CD81. They may also be used to modulate CD81 interaction with natural CD81 ligands or receptors that bind to or interact with CD81. For example, a ligand conjugate may be engineered to block a site on CD81 to which *Plasmodium* parasites bind as well as other sites on CD81 to which HCV binds [16-20].

The small molecule ligands and their CD81-binding fragments disclosed herein find many applications including as anti-*Plasmodium* compounds that modulate or interfere with *Plasmodium* parasite binding to cells expressing CD81, as competitive inhibitors of parasite binding in vivo, in vitro, or in antimicrobial or antiparasite compositions, such as disinfectants or microbe-neutralizing compositions; or as reagents or tools for identifying new ligands that bind to CD81 or the CD81 sites described above. For example, the ligands described herein can be used in a competitive inhibition assay to identify other molecules having a higher or lower ability to bind to CD81 or to inhibit the attachment of a particular ligand to CD81.

Chemical derivatives of the CD81 ligands are also described, including ligands or CD81-binding fragments of ligands that are chemically derivatized to remove undesirable physical or biological properties or to modulate absorption, distribution, or localization of the derivatized ligand. Prodrugs of the CD81-binding ligands and their fragments disclosed, which lack biological activity until transformed in vivo or in vitro into a ligand as described herein, are also contemplated.

Specific, non-limiting embodiments of the invention include the following:

1. A molecule comprising a first small molecule ligand for CD81 that is covalently-linked via a linker moiety to a second small molecule ligand for CD81, wherein the first small molecule ligand is selected from the group consisting of Ligand 7962, 87504, 40614, 30930, 98026, 75866, 93033, 90444, 73735, and 281816 (NCI diversity set ligand numbers) or a CD81-binding fragment thereof. CD81-binding fragments of the ligands enumerated above are described by FIG. 11. A ligand may be bound to a linker or directly to another ligand through a covalent chemical linkage to one, two, three, four or more of its atoms.
2. The molecule of embodiment 1, wherein the second small molecule ligand binds to a site on CD81 that inhibits the attachment to or interaction of a microorganism that is *Plasmodium* with CD81.
3. The molecule of embodiment 1, wherein the second small molecule ligand binds to a site on CD81 that inhibits HCV attachment to or interaction with CD81.
4. The molecule of embodiment 1, wherein the second small molecule ligand is selected from the group consisting of Ligand 73735, 87504, 40614, 7962, 30930, 98026, 75866, 93033, 90444 and 281816 or CD81-binding fragments thereof.
5. The molecule of embodiment 1 that comprises Ligand 7962 and Ligand 73735; or Ligand 7962 and 281816; or CD81-binding fragments thereof.
6. The molecule of embodiment 1, further comprising at least one, two, three, four, five, six, seven, eight, nine, ten, or more covalently-linked small molecule ligand(s) that binds to CD81.
7. The molecule of embodiment 1, wherein said first or second small molecule ligand, or both, binds to at least one of Sites 1-10 on CD81. Sites 1-10 are described by FIG. 9 and binding may constitute binding near all of the amino acid residues denoted in black in each panel of FIG. 9.
8. The molecule of embodiment 1, wherein said linker comprises a chemical linker selected from the group consisting of a chemical bond, a bivalent hydrocarbon radical, a multivalent hydrocarbon radical, a bivalent hydrocarbon radical containing at least one heteroatom, bivalent glycine residue(s), miniPEGs, a multivalent hydrocarbon radical containing at least one heteroatom, a multivalent radical containing oxygen, nitrogen or sulfur, a functionalized polyethylene glycol, diamino- or triamino-alkanes, or dicarboxy- or tricarboxy-alkanes.
9. The molecule of embodiment 1 that comprises a chemical linker that is a peptide or peptide analog, amino acid, a carbohydrate or carbohydrate analog, a sugar or sugar analog, nucleic acid or nucleic acid analog, or a dendrimer.
10. The molecule of embodiment 1 that is covalently attached to an effector molecule selected from the group consisting of a dendrimer, nanoparticle, liposome, biotin, avidin, avidin analog, antibody, and other effector.
11. The molecule of embodiment 1 that is non-covalently associated with an effector molecule selected from the group consisting of a dendrimer, nanoparticle, liposome, biotin, avidin, avidin analog, antibody, and other effector.
12. A composition comprising at least one molecule according to embodiment 1 and a pharmaceutically acceptable carrier or excipient.
13. A method for modulating a biological activity of CD81 or an activity mediated by or through CD81. comprising contacting CD81 or a cell having CD81 with at least one molecule of embodiment 1.
14. A method for treating a subject exposed to a *Plasmodium* parasite comprising administering the molecule of embodiment 1.
15. The method of embodiment 14, wherein said *Plasmodium* parasite is *Plasmodium falciparum, Plasmodium vivax, Plasmodium malariae, Plasmodium ovale, Plasmodium knowlesi*, or other *Plasmodium* species that infects humans.
16. A composition comprising at least one molecule selected from the group consisting of Ligand 7962, 87504, 40614, 30930, 98026, 75866, 93033, 90444, 73735, and 281816 (NCI diversity set ligand numbers); or a CD81-binding fragment thereof.
17. The composition of embodiment 16 that comprises at least two, three, four, five, six, seven, eight, nine or ten different molecules selected from the group of Ligand 7962, 87504, 40614, 30930, 98026, 75866, 93033, 90444, 73735, and 281816 (NCI diversity set ligand numbers) and a pharmaceutically acceptable carrier or excipient.

18. A method for modulating a biological activity of CD81 or an activity mediated by or through CD81 comprising contacting CD81 or a cell having CD81 with the composition of embodiment 16.
19. A method for treating a subject exposed to a *Plasmodium* parasite comprising administering the composition of embodiment 16 to said subject.
20. The method of embodiment 19, wherein said *Plasmodium* parasite is *Plasmodium falciparum, Plasmodium vivax, Plasmodium malariae, Plasmodium ovale, Plasmodium knowlesi*, or other *Plasmodium* parasite that infects humans.
21. A method for propylactically protecting a high risk subject against malaria comprising administering the molecule of embodiment 1 or at least one molecule comprising a CD81-binding fragment of Ligand 7962, 87504, 40614, 30930, 98026, 75866, 93033, 90444, 73735, and 281816, as a prophylactic agent. The identified ligands and ligand conjugates containing them interfere with the ability of *Plasmodium* to infect liver cells. This differs from a conventional anti-malarial drug that kills *Plasmodium*. The ligands and conjugates according to the invention can be used as prophylactic agents to protect high risk individuals against malaria infection. The duration of protection window will depend on the plasma half-life and toxicity of the developed drug candidates.
22. A method for treating coinfection with malaria and HCV comprising administering a mixture of molecule of embodiment 1 or at least one molecule comprising a CD81-binding fragment of Ligand 7962, 87504, 40614, 30930, 98026, 75866, 93033, 90444, 73735, and 281816; and at least one molecule which interferes with HCV binding to CD81 such as those described by PCT/US2013/071056. The increasing prevalence of HCV infection in countries where malaria is endemic and the predicted alteration in the patterns and spread of malaria due to climate change, support the possibility of occurrence of coinfection. Because *Plasmodium* and HCV use common host entry actors to infect hepatocytes including CD81, a mixture of antimalarial drag leads and anti-HCV drug leads which interfere with the ability of the two pathogens to CD81 may be used to treat patients coinfected with them.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 3B shows SPR data for all 10 malaria ligands that bind to CD81.

FIG. 4A. Inhibition of *P. yoelii* Infection of HepG2 Cells. Ligand 7962 was found to have the strongest inhibitory effect followed by ligand 73735, 75866 and 90444. Ligand 40614 was found to enhance the infection with *P. yoelii* in HepG2-CD81.

FIG. 4B. The gliding Assay was used to confirm the ligands were not toxic to the cells.

FIGS. 5A and 5B, respectively, show inhibition of *P. yoelii* and *P. berghei*

FIGS. 6A and 6B compare inhibition of *P. yoelii* and *P. falciparum* infection of HepG2 cells.

FIGS. 7A, 7B, 7C, 7D, and 7E, depict different binding modes of ligand 7962 to CD81. A number of ligand 7962 conformations interacted with the 21 amino acid sequence and Asp137 that were identified as important for malaria infection. The black dots in FIGS. 7A and 7B show the atom locations of all the different bound conformers identified. The conformers that bind with the highest affinity are shown in FIGS. 7C, 7D and 7E.

FIGS. 8A, 8B, 8C, 8D, 8E and 8F depict different binding modes of ligand 73735 to CD81. A number of ligand 73735 conformations interacted with the 21 amino acid sequence and Asp137 that were identified as important for malaria infection. The black dots in the first two structures show the atom locations of all the different bound conformers identified. Specific bound ligand conformers are shown in the other structures.

FIGS. 9A, 9B, 9C, 9D, 9E, 9F, 9G, 9H, 9I, and 9J, respectively, depict Sites 1, 2, 3, 4, 5, 6, 7, 8,9 and 10 on CD81 to which small molecule ligands that inhibit the binding of *Plasmodium* bind.

FIGS. 10A, 10B and 10C illustrate Fragment-based Drug Design based on ligands 689002 and 21034.

FIGS. 11A, 11B, 11C, 11D, 11E, 11F, 11G, 11H, 11I, 11J, 11K, 11L, 11M, 11N and 11O exemplify some CD81-binding ligand conjugates containing fragments of CD81-binding ligands. These figures describe particular CD81-binding fragments (circled) as well as conjugates comprising CD81-binding ligand fragments. Atoms intersected by a circle or atoms in ring structures that are not entirely within a circle may optionally be included as part of the CD81-binding fragment.

FIG. 12. Use of model ligand fragments to determine the Tanimoto coefficient.

FIG. 13. Example of small set of pharmaceutically relevant fragments used to compare to fragments of drug candidate ligands and calculate a Tanimoto coefficient.

DETAILED DESCRIPTION OF THE INVENTION

The invention pertains to small molecule ligands and ligand conjugates that bind to CD81 and which inhibit or interfere with the interaction of the malaria parasite with CD81 and host cells expressing CD81.

Definitions

The terms used to describe the ligands and ligand binding sites are described below.

The term "CD81" is given its ordinary meaning in the art (Cluster of Differentiation-81). Human CD81 has been sequenced and its crystal structure determined, which is incorporated by reference to Protein Data Bank Entry 1G8Q.

Figure 1A:
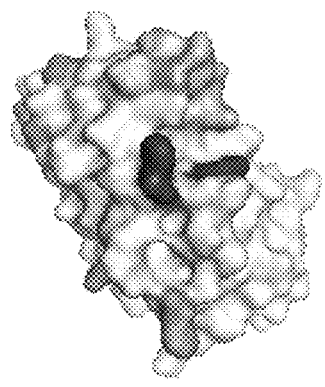
FIGS. 1A and 1B depict a stretch of 21 amino acid residues involved in *Plasmodium* sporozoites: CD81-LEL interaction. Red, Green, Blue: amino acids surrounding three main ligand binding sites. Light orange: V135-D155 - Dark orange: D137.

CD81 analogs from non-human animals are known. As used herein, the term CD81 refers to both natural or artificial variants of CD81, such as molecules having at least 80%, 85%, 87.5%, 90%, 92.5%, 95%, 97.5%, 98%, 99% amino acid sequence similarity or identity to SEQ ID NOS: 1-3 or to the amino acid sequence of PDB 1G8Q.

The term "*Plasmodium*" is given its customary taxonomical meaning. An alternative term used herein is *Plasmodium* parasite or just *Plasmodium* to refer to a microorganism within this genus. Examples of *Plasmodium* species include *Plasmodium falciparum, Plasmodium vivax, Plasmodium malariae, Plasmodium ovale*, and *Plasmodium knowlesi.*

The term "HCV" refers to Hepatitis C virus. The E2 protein of HCV is a protein ligand for CD81.

A "variant" or "analog" of a polypeptide may differ in primary, secondary or tertiary structure from a polypeptide described herein. This term includes post-translationally or chemically modified polypeptides as well as polymorphs of a polypeptide such as a CD81 polymorph. A variant, analog or modified form of a CD81 polypeptide or a *Plasmodium* polypeptide can be characterized by a degree of amino acid similarity or identity of 80%, 85%, 87.5%, 90%, 92,5%, 95%, 97,5%, 98%, 99% to a known polypeptide sequence.

BLASTP may be used to identify an amino acid sequence having at least 80%, 85%, 87.5%, 90%, 92.5%, 95%, 97.5%, 98%, 99% sequence similarity or identity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure.

A "small organic molecule" includes low molecular weight organic compounds such as compounds approximately 800 daltons in mass. Derivatives or conjugates of small organic molecules may contain amino acid residues, short peptide linkers or other moieties. Small organic molecules according to the invention will bind to or interact with CD81. These small molecules may bind to a particular site on CD81, such as the ten sites show by FIG. 9 discovered by the inventors. They may also bind to more than one site. Moreover, portions or fragments of these small molecule ligands that bind to CD81 have been identified and may be used to form portions of larger molecules that bind to CD81.

Ligands binding to CD81 may have a greater or lesser affinity for CD81 than a natural ligand from CD81, such as the natural HCV E2 ligand or *Plasmodium* polypeptides that bind or interact with CD81. The binding of a small molecule ligand to CD81 may passively block binding of other ligands to CD81 such as determinants on *Plasmodium* or HCV involved in attachment and invasion of CD81-bearing host cells. Ligand binding to CD81 may also allosterically affect CD81 or molecules associated with CD81 in the host cell or otherwise trigger or transduce a signal thus modifying the capacity of a host cell to be recognized or invaded by *Plasmodium* parasites or other pathogens that interact with the host cell via CD81.

The binding affinity and efficacy of a CD81 ligand molecule can be determined by methods known in the art. Different ligands will exhibit different binding affinities for CD81, for example, binding affinity can range from 1 nM to 10,000 nM and all intermediate values and subranges within this range, such as 1 nM, 10 nM, 100 nM, 1,000 nM, 5,000 nM and 10,000 nM. The inventors have found that ligands that bind to at least two different sites identified on CD81 can bind more strongly to CD81 than the individual ligands for each site.

The invention contemplates small molecules that bind to CD81 per se, as well as larger conjugates or hybrid molecules containing one or more small molecules that interact with CD81. The larger conjugates or hybrid molecules may comprise more than one determinant that binds to CD81, more than one copy of a particular CD81-binding determinant, or determinants that bind to different sites on CD81. Other effector or functional determinants which need not contribute to the ability to bind to CD81 may be attached to a small molecule ligand or to a CD81-binding fragment of the ligand.

Small organic molecules that may be screened for their ability to interact with CD81 are publicly available, for example, as described in the ZINC database or by NCI Diversity Set 1, 2 or 3 (http://dtp.nci.nih.gov/branches/dscb/diversity_explanation.html; https://zinc.docking.org/catalogs/ncidiv; and https://zinc.docking.org/db/byvendor/ncidiv/ ncidiv.in; each last accessed Jun. 2, 2014 and each of which is incorporated by reference). ZINC is a free database of commercially-available compounds for virtual screening. ZINC contains over 21 million purchasable compounds in ready-to-dock, 3D formats. ZINC is provided by the Shoichet Laboratory in the Department of Pharmaceutical Chemistry at the University of California, San Francisco (UCSF), see: Irwin, Sterling, Mysinger, Bolstad and Coleman, *J. Chem. Inf. Model.* 2012 DOI: 10.1021/ci3001277. The original publication is Irwin and Shoichet, *J. Chem. Inf. Model.* 2005;45(1): 177-82. The compounds described in the ZINC database as of Jun. 2, 2014 are incorporated by reference to the Zinc and NCI links and publications above.

Functional variants or chemical derivatives of the small organic molecules of the invention are also contemplated. Like the unmodified small organic molecule, these variants will bind to CD81 but may have one or more substitutions to the chemical structure of the unmodified small organic molecule ligand. Other substitutions to the core structure of a small organic molecule ligand described herein include other functional groups that improve i) binding to CD81, ii) confer specific properties such as those related to solubility, stability, pharmacokinetics, biodistribution, absorption, tissue uptake, residence time in tissue, or ones that minimize toxicity, excretion or metabolism, iii) enable the small molecule ligand to be conjugated to other molecules, and/or iv) facilitate the diagnostic use of the small molecule ligand.

Examples include the addition or substitution of other atoms such as halogens (chlorine, fluorine, iodine, bromine), metals or radioisotopes (to enable detection or visualization), tags such as fluorescent dyes or molecules, biotin, digoxigenin, peptides amino acids (to improve uptake, delivery and biodistribution), or functional groups such as carboxylic, amino, amine, amide, azo, ester, thiol, sulfonyl, nitro, alkoxy, acetyl, acetoxy, hydroxyl or other alcohol, aldehyde, carbonyl, alkyl, alkene or alkene groups or chains, ether, epoxide, hydrazone, imide, imine, isocyanate, isonitrile, isothiocyanate, ketone, nitrile, nitrene, nitro, nitroso, organophosphorus, oxime, phosphonic or phosphonous acid, sulfone, sulfonic acid, sulfoxide, thiocyanate, thioester, thioether, thioketone, urea, pyridine groups or other aromatic rings.

Most small molecule ligands according to the invention are not polymers. However, conjugates of small molecule ligands may contain multiple units of one or more small organic molecule ligands, for example, as linked to each other or to a dendrimer. In addition to small organic molecules linked together with a chemical linker, these small organic molecule ligands may be conjugated to larger moieties such as antibodies and other proteins, nucleic acids and nucleic acid analogs, carbohydrate and sugar molecules, etc. The small molecule ligands, conjugates or hybrids may also be conjugated to detectable moieties such as avidin or streptavidin, biotin or other detectable tags. Hybrid molecules that comprise chemical moieties from two or more known small organic molecule ligands may be engineered by a process of fragment-based extension or by combining CD81-binding fragments of the ligands identified herein with other ligands or fragments of ligands.

In some embodiments of the invention the small molecule ligands are connected by other moieties such as by linkers or spacers. These linkers or spacers may be used to join small molecules that bind to different portions of CD81 and to space the small molecule moieties in a joined molecule so that they can bind to different parts of CD81. For example, a small molecule that binds to a site on CD81 may be spaced from 0 (e.g., where a carboxyl group on one small molecule ligand is coupled to an amine group on another) to about 30 Å (3 nm) apart from one that binds to another site using a linker of an appropriate length. In most cases, linkers would range from 2 or 3 to about 7-10 Å. Generally, small organic ligand molecules will be joined by linkage to a single position on each ligand to another ligand or to an intervening linker. However, linkage may also occur at 2 or more positions on a ligand molecule to another ligand molecule or linker. Linkers may have different chemical structures including straight-chain and branched chain structures, and structures including saturated or unsaturated bonds (e.g., alkyl, alkenyl or alkynyl), heteroatoms (e.g., nitrogen, oxygen or sulfur) or aromatic moieties. Bivalent and multivalent linkers may contain the same or different reactive chemical groups for linking two or more small molecule ligands for CD81. Linkers may range from 1, 2, 3, 4, 5, 6, 7, 8, 9, 10 or more atoms in length. Direct linkages between two or more small molecule ligands may also be used to form conjugates of CD81 ligands where each ligand has a chemical group that can react with a chemical group on another ligand.

Linkers suitable for use in the invention are known in the art and are incorporated by reference to Ducry, et al., *Bioconjugate Chem.* 21, 5-13, *Antibody-Drug Conjugates: Linking Cytotoxic Payloads to Monoclonal Antibodies* (2010); to Gordon, et al., *J. Chem. Technol. Biotechnol,* 74:835-851, *Solid phase synthesis—designer linkers for combinatorial chemistry: a review* (1999), and to Leitner, et al., Mol. Cell. Proteonom. 9:1634-1649 (2010), which are incorporated by reference, Exemplary linkers include lysine, diaminomethane, and polyethylene glycol (PEG) moieties.

A "composition" or "pharmaceutical or therapeutic composition" according to the invention refers to a combination of carrier, excipient, or solution with a small molecule, ligand conjugate or hybrid molecule. The term "pharmaceutically acceptable carrier" includes any and all carriers and excipients such as diluents, solvents, dispersing agents, emulsions, lipid bilayers, liposomes, coatings, preservatives including antibacterial or antifungal agents, isotonic agents, pH buffers, and absorption modulating agents, and the like, compatible with the molecules of the present invention and suitable for pharmaceutical administration, The use of such carriers, disintegrants, excipients and agents for administration of pharmaceutically active substances is well known in the art, see the *Handbook of Pharmaceutical Excipients,* $3^{rd}$ edition, Am. Pharm. Assoc. (2000) which is incorporated by reference. The pharmaceutical compositions of the invention are generally formulated for compatibility with an intended route of administration, such as for parenteral, oral, or topical administration.

The therapeutic compositions of the invention include at least one molecule according to the invention in a pharmaceutically acceptable carrier. A "pharmaceutically acceptable carrier" will be at least one component conventionally admixed with, and used for, the administration of an active ingredient, biological product, or drug. A therapeutic composition may be sterile or in a form suitable for administration to a human or non-human subject. A carrier may contain any pharmaceutical excipient used in the art and any form of vehicle for administration. The compositions may be, for example, injectable solutions, aqueous suspensions or solutions, non-aqueous suspensions or solutions, sprays, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like. A suitable dosage form may be selected by one of skill in the art from forms such as those described by and incorporated by reference to "Dosage Form"; NCI Thesaurus OID: 2.16.840.1.113883.3.26.1.1 NCI concept code for pharmaceutical dosage form: C42636; accessible at:

http://www.fda.gov/ForIndustry/DataStandards/StructuredProductLabeling/ucm162038.htm
(last accessed May 16, 2014).

Orally administered compositions include a solid carrier or excipient or may be formulated as liquid or gel preparations and may include an edible or inert carrier and may be enclosed in capsules, compressed into tablets, or formulated as a troche. Orally administered compositions may be prepared in a time-release or encapsulated form to prevent degradation in the stomach and optimize uptake of a molecule.

Injectable compositions may be formulated by methods well known in the art and may encompass sterile solutions or dispersions of therapeutic molecules. Such will usually include a sterile diluent, such as water, normal saline, or other buffer compatible with the molecules of the invention. Injectable compositions may be prepared in unit dosages or in unit dose containers, such as vials, ampules, or syringes.

Conventional buffers and isotonic agents may be used and pH may be adjusted using well known agents, such as HCl or NaOH or buffers. Antimicrobial or bacteriostatic agents, chelating agents, such as EDTA or EGTA, and antioxidants and preservatives may be present.

The therapeutic compositions of the invention may be administered by any acceptable route of administration including topically, on to a mucous membrane, orally or enterically or parenterally. These routes include, but not limited to topical, transmucosal, orally (including buccal, sublingual), mucosally (conjunctiva, nasal, sinal, urethral, vaginal, intestinal, rectal), enteric, transdermal, intradermal, subcutaneous (s.c.), intramuscular, intraperitoneal, intravenous (i.v.) intracardiac, into a joint or bone, into an organ (brain, spinal chord, eye, ear, liver, spleen, kidney, gall bladder, bladder), into bone, cartilage, or joint tissue, by inhalation (e.g., intranasal, intratracheal, intrapulmonary, or intrabroncial), oral, subuccal. Routes may be selected by those of skill in the art from (and are incorporated by reference to) those listed in the U.S. FDA, CDER, Data Standards Manual "Routes of Administration"; FDA Data Element Number. None. CDER Data Element Number. C-DRG-00301; Data Element Name. Route of Administration; Data Element OID: 2.16.840.1.113883.3.26.1.1.1 Data Element NCI Concept ID: C38114; Version Number 004 accessible at http://www.fda.gov/Drugs/DevelopmentApprovalProcess/FormsSubmissionRequirements /ElectronicSubmissions/DataStandardsManualmonographs/ucm071667.htm; (last accessed May 16, 2014).

The term "subject" refers to an individual susceptible to *Plasmodium* infection especially, but not limited to, human subjects. A high-risk human subject may include a) a immuno-compromised patient traveling to malaria endemic regions, b) medical/other staff visiting malaria endemic regions and c) other risk groups such as pregnant women, adults over 65 years, or children under 5 years of age may or may not benefit from such drugs pending their toxicity assessment.

Characterization of Small Molecules that Bind to CD81

The inventors identified ten small molecule ligands that bind next to key amino acids on CD81-LEL that should inhibit or affect *Plasmodium* interaction with CD81. These are Ligands 7962, 87504, 40614, 30930, 98026, 75866, 93033, 90444, 73735, and 281816.

| NCI-ID | SMILE | Chemical Name | CAS # |
|---|---|---|---|
| 73735 | COc1cc(ccc1Nc2ccccc2C(=O)[O—])c3ccc(c(c3)OC)Nc4ccccc4C(=O)[O—] | 2-{[4'-(2-carboxyanilino)-3,3'-dimethoxy[1,1'-biphenyl]-4-yl]amino} benzoic<br>IUPAC Name: 2-[4-[4-(2-carboxylatoanilino)-3-methoxyphenyl]-2-methoxyanilino]benzoate | 52962-95-5 |
| 90444 | Cc1cc(c(c(c1)C(=O)[O—])N)C | 2-Amino-3,5-dimethylbenzoic acid or 2-Amino-3,5-dimethyl benzoic acid<br>IUPAC Name: 2-amino-3,5-dimethylbenzoate | 14438-32-5, 306935-99-9 |
| 7962 | CCC(C)(C)c1ccc(cc1)Oc2cccc(c2)C(=O)[O—] | 3-(4-tert-pentylphenoxy)benzoic acid<br>IUPAC Name: 3-[4-(2-methylbutan-2-yl)phenoxy]benzoate | 74525-53-4 |

-continued

| NCI-ID | SMILE | Chemical Name | CAS # | |
|---|---|---|---|---|
| 75866 | c1ccc2c(c1)ccn2CC(=O)[O—] | Indol-1-yl-acetic acid or 1-INDOLEACETIC ACID<br>IUPAC Name: 2-indol-1-ylacetate | 193544-62-6, 24297-59-4 | |
| 93033 | O=c1n(ccc([nH]1)=O)CC(Nc1cc(c(cc1)C(=O)O)O)=O | 4-[2-(2,4-dioxo-1,2,3,4-tetrahydropyrimidin-1-yl)acetamido]-2-hydroxybenzoic acid<br>IUPAC Name: 4-[[2-(2,4-dioxopyrimidin-1-yl)acetyl]amino]-2-hydroxybenzoate | 4116-42-1 | |
| 87504 | C1=CN=CC(=C1)[C@H]2CCCC[N+]2 | 3-[(2R)-piperidin-1-ium-2-yl]pyridine<br>IUPAC Name: 3-[(2S)-piperidin-2-yl]pyridine | 13078-04-1, 13078-04-1 | |
| 40614 | c1ccccc1/C=C(\c1ccccc1)C(=O)O | (E)-2,3-diphenylprop-2-enoate<br>IUPAC Name: 2,3-diphenylprop-2-enoate | 3368-16-9, 91-48-5 | |
| 30930 | [nH]1c2ccc(cc2c1C(=O)O)OCc1ccccc1 | 5-(benzyloxy)-1H-indole-2-carboxylic acid<br>IUPAC Name: 5-phenylmethoxy-1H-indole-2-carboxylic acid | 6640-09-1 | |

| NCI-ID | SMILE | Chemical Name | CAS # |
|---|---|---|---|
| 98026 | O=C1C(=C(OCC(=O)O)C(=O)c2c1cccc2)C/C=C(\C)C | 2-{[3-(3-methylbut-2-en-1-yl)-1,4-dioxo-1,4-dihydronaphthalen-2-yl]oxy}acetic acid IUPAC Name: 2-[3-(3-methylbut-2-enyl)-1,4-dioxonaphthalen-2-yl]oxyacetate | CAS |
| 281816 | C[NH+]1CCN(CC1)C2CC3=CC=CC=C3SC4=C2C=C(C=C4)SC | 1-methyl-4-[(5S)-3-methylsulfanyl-5,6-dihydrobenzo[b][1]benzothiepin-5-yl]piperazin-1-ium IUPAC Name: 1-methyl-4-(3-methylsulfanyl-5,6-dihydrobenzo[b][1]benzothiepin-5-yl)piperazine | 19728-88-2, 20229-30-5 |

In addition to the ten ligand structures shown above, CD81-Binding Fragments of these ligands may be used to design CD81-binding molecules as illustrated in FIG. 11.

Core Structures of Small Molecules that Bind to CD81

The following four core structures define genuses of small molecule ligands which can bind to CD81 and inhibit the attachment of *Plasmodium* to CD81 or CD81-bearing cells.

Core Structure 1:

wherein:
X=C, S, N, O, or —S=O
R1-R6, R8=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, C(I)$_x$, C(Cl)$_x$ or —CH$_3$
R7=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, —C(I)$_x$, C(Cl)$_x$, —CH$_3$, —C(CH$_3$)$_3$, —C(CH(CH$_3$)$_2$CH$_2$CH$_3$, or —C(CH(CH$_3$)$_2$CH$_2$CO$_2$H Core Structure 2:

wherein:
X or Y=C, S, N, O, or —S=O
Z=C, N, O
R1-R1$_2$=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, C(I)$_x$, —CH$_3$, or —(CH$_2$)$_x$OCH$_3$ Core Structure 3:

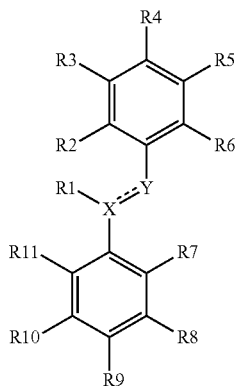

wherein:
X, Y=C, S, N, or)
Z=C, N, O
R1-R11=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, —C(I)$_x$, C(Cl)$_x$, —CH$_3$, or —(CH$_2$)$_x$OCH$_3$

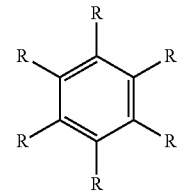

Core Structure 4:
wherein:
X=C, N, or O
R1-4, R6-7=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, —C(I)$_x$, C(Cl)$_x$, —CH$_3$, or —(CH$_2$)$_x$OCH$_3$.
R5=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, —C(I)$_x$, C(Cl)$_x$, —CH$_3$, —(CH$_2$)$_x$OCH$_3$ or —OCH$_2$Phenyl
Core Structure 5:

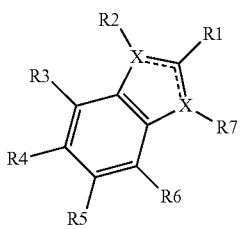

X=N, S, O
R=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, —C(I)$_x$, C(Cl)$_x$ or —CH$_3$

Core Structure 6:

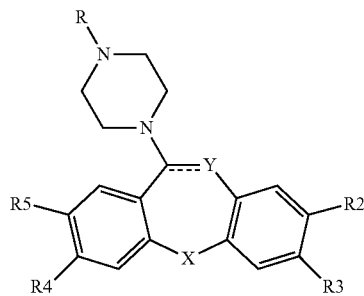

R=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH$_2$, —(CH$_2$)$_x$NH$_2$, —CH(OH)$_2$, —(CH$_2$)$_x$OH, —SO$_2$H, —(CH$_2$)$_x$NO$_2$, —NO$_2$, —C(F)$_x$, —C(Br)$_x$, —C(I)$_x$, C(Cl)$_x$ or —CH$_3$

Core Structure 7:

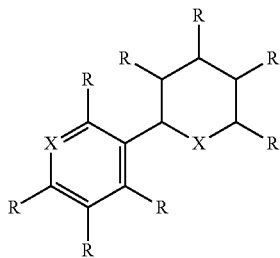

wherein:
X=C, S, N, O, —S=O, CH$_2$SO$_2$H, or CH$_2$SO$_2$CH$_3$
Y=C, S, N, or O
R=—H, —CH$_2$CH$_2$OH, —CH$_2$CH$_2$OCH$_2$CH$_2$OH, —CH=O, —(CH$_2$)$_x$NH$_2$, —(CH$_2$)$_x$CO$_2$H, —((CH$_2$)$_2$O)$_x$NH$_2$, —((CH$_2$)$_2$O)$_x$CO$_2$H, —CH$_3$, or —CH$_2$CH$_3$
R$_2$=H, Cl, F, Br, I, —HC=O, —CO$_2$H, —OH, =O, —NH$_2$, —RC=O, —CH(CH$_3$)$_2$, —CH$_3$S=O, —CH$_3$SO$_2$, —CH=O, —CF$_3$, —CH$_3$, —CBr$_3$, —CI$_3$, CCl$_3$, —SO$_2$H, —SO$_2$CH$_3$, —SCH$_3$, or —CH$_2$CH$_3$
R$_3$=H, Cl, F, Br, I, —HC=O, —CO$_2$H, —OH, =O, —NH$_2$, —RC=O, —CH(CH$_3$)$_2$, —CH(CH$_3$)$_2$, —CH$_3$S=O, —CH$_3$SO$_2$, —CH=O, —CF$_3$, —CH$_3$, —CBr$_3$, —CI$_3$, CCl$_3$, —SO$_2$H, —SO$_2$CH$_3$, —SCH$_3$, or —CH$_2$CH$_3$
R4=H, Cl, F, Br, I, —HC=O, —CO$_2$H, —OH, =O, —NH$_2$, —RC=O, —CH(CH$_3$)$_2$, —CH$_3$S=O, —CH$_3$SO$_2$, —CH=O, —CF$_3$, CH$_3$, —CBr$_3$, —CI$_3$, CCl$_3$, —SO$_2$H, —SO$_2$CH$_3$, —SCH$_3$, or —CH$_2$CH$_3$
R5=H, Cl, F, Br, I, —HC=O, —CO$_2$H, —OH, =O, —NH$_2$, —RC=O, —CH(CH(CH$_3$)$_2$, —CH$_3$S=O, or —CH$_3$SO$_2$ Core Structure 8:

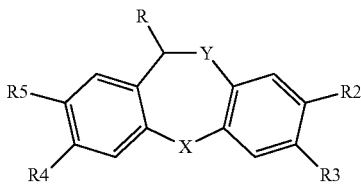

wherein
X=C, S, N, O, S=O, CSO₂H, or CSO₂CH₃;
Y=C, S, N, or O;
R=—CH₂CH₂OH, —CH₂CH₂OCH₂CH₂OH, —CH=O, —(CH₂)$_x$NH₂, —(CH₂)$_x$CO₂H, —((CH₂)₂O)$_x$NH₂, —((CH₂)₂O)$_x$CO₂H, —NH(CH₂)$_x$NH₂, —NH₂, —NH(CH₂)$_x$OH, —NH(CH₂)$_x$CO₂H, —CH₃, or —CH₂CH₃;
R₂=H, Cl, F, Br, I, —HC=O, —CO₂H, —OH, =O, —NH₂, —RC=O, —CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃;
R₃=H, Cl, F, Br, I, —HC=O, —CO₂H, —OH, =O, —NH₂, —RC=O, —CH(CH₃)₂, —CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃;
R₄=H, Cl, F, Br, I, —HC=O, —CO₂H, —OH, =O, —NH₂, —RC=O, —CH(CH₃)₂, —CH₃S=O, —CH₃SO₂, —CH=O, —CF₃, —CBr₃, —CI₃, CCl₃, —SO₂H, —SO₂CH₃, —SCH₃, or —CH₂CH₃;
R₅=H, Cl, F, Br, I, —HC=O, —CO₂H, —OH, =O, —NH₂, —RC=O, —CH(CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃.

Core Structure 9:

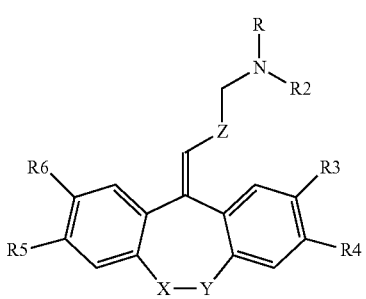

wherein
X=C, S, N, O, or S=O;
Y=C, S, N, O, or S=O;
R=—H, Cl, F, Br, I, —HC=O, —CO₂H, —OH, =O, —NH₂, —RC=O, —(CH₂)$_x$OH, —(CH₂)$_x$NH₂, —(CH₂)$_x$CO₂H, —((CH₂)$_x$O)$_x$ NH₂, —((CH₂)$_x$O)$_x$CO₂H, —((CH₂)$_x$O)$_x$OH, —CHOCH₃, —SO₂H, —SO₂CH₃, —CH₂SO₂H, —CH₂SO₂CH₃, —CH₃, or —CH₂CH₃;
R₂=H, Cl, F, Br, I, —HC=O, —CO₂H, —OH, =O, —NH₂, —RC=O, —(CH₂)$_x$OH, —(CH₂)$_x$NH₂, —(CH₂)$_x$CO₂H, —((CH₂)$_x$O)$_x$NH₂, —((CH₂)$_x$O)$_x$CO₂H, —((CH₂)$_x$O)$_x$OH, —CHOCH₃, —SO₂H, —SO₂CH₃, —CH₂SO₂H, —CH₂SO₂CH₃, —CH₃, or —CH₂CH₃;
R₃=H, Cl, F, Br, I, —HC=O, —CO₂H, —OH, =O, —NH₂, —RC=O, —SO₂H, —SCH₃, —CH₃, —CH₂CH₃;
R₄=H, Cl, F, Br, I, —HC=O, —CO₂H, —OH, =O, —NH₂, —RC=O, —CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃;
R₅=H, Cl, F, Br, I, —HC=O, —CO₂H, —OH, =O, —NH₂, —RC=O, —CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃;
R₆=H, Cl, F, Br, I, —HC=O, —CO₂H, —OH, =O, —NH₂, —RC=O, —SO₂H, —SCH₃, —CH₃, or —CH₂CH₃.

Core Structure 10:

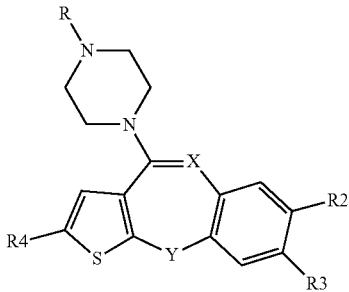

wherein
X=C, S, N, or O;
Y=C, S, N, O, —S=O, —SO₂H, or —SO₂CH₃;
R=—H, —CH₂CH₂OH, —CH₂CH₂OCH₂CH₂OH, —CH=O, —(CH₂)$_x$NH₂, —(CH₂)$_x$CO₂H, —((CH₂)₂O)$_x$NH₂, —((CH₂)₂O)$_x$CO₂H, —NH(CH₂)$_x$NH₂, —CH₃, or —CH₂CH₃;
R₂=H, Cl, F, Br, I, —HC=O, —CO₂H, —OH, =O, —NH₂, —RC=O, —CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃;
R₃=H, Cl, F, Br, I, —HC=O, —CO₂H, —OH, =O, —NH₂, —RC=O, —CH(CH₃)₂, —CH₃S=O, —CH₃SO₂, —CH=O, —CF₃, —CH₃, —CBr₃, —CI₃, CCl₃, —SO₂H, —SO₂CH₃, —SCH₃, or —CH₂CH₃;
R₄=H, Cl, F, Br, I, —HC=O, —CO₂H, —OH, =O, —NH₂, —RC=O, —CH(CH₃)₂, —CH₃S=O, or —CH₃SO₂, —CH=O, —CF₃, —CBr₃, —CI₃, CCl₃, —SO₂H, —SO₂CH₃, —SCH₃, or —CH₂CH₃

Core Structure 11:

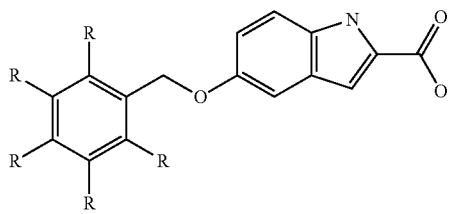

R=H, Cl, F, Br, I, —OH, =O, —CH=O, —S=O, —(CH$_2$)$_x$SO, —(CH$_2$)$_x$SO$_2$, —CO$_2$H, —(CH$_2$)$_x$CO$_2$H, —NH2, —(CH$_2$)$_x$NH$_2$, —CH(OH)$_2$, —(CH2)$_x$OH, —SO$_2$H, —(CH2)$_x$NO$_2$, —NO$_2$, —C(F)$_x$, —C(Br)$_x$, —C(I)$_x$, C(Cl)$_x$ or —CH$_3$.

Ligand Conjugates that Bind to CD81

Two or more of the ten ligands that bind to CD81 may be formulated as a conjugate as shown below. In the conjugates depicted below "x" is a value selected from 0, 1, 2, 3, 4, 5, or 6:

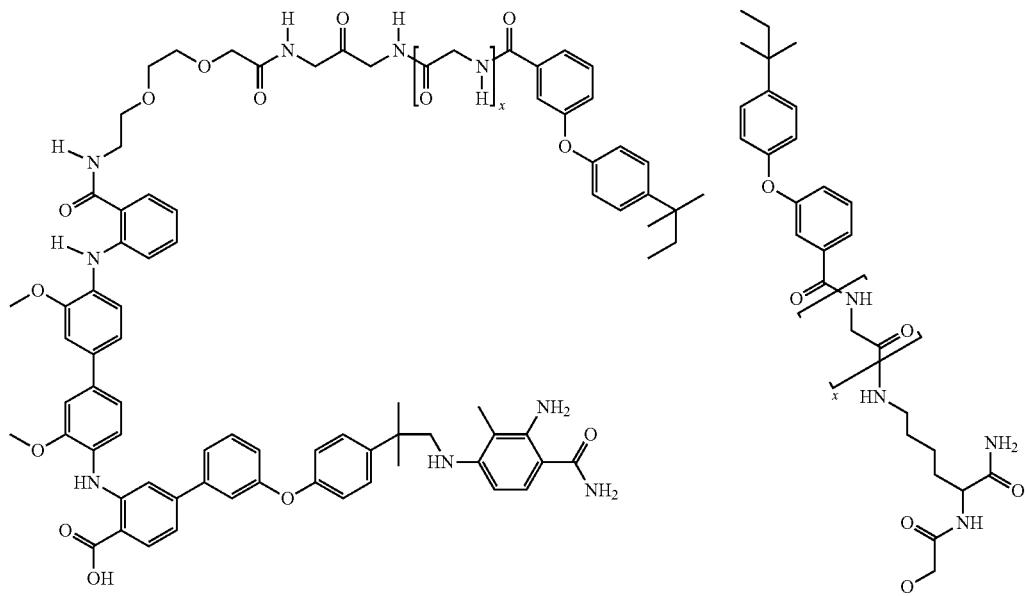

7962GP73735a7962a9044

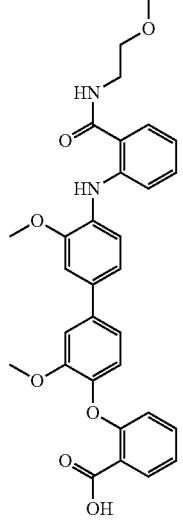

7962GLP73735

-continued
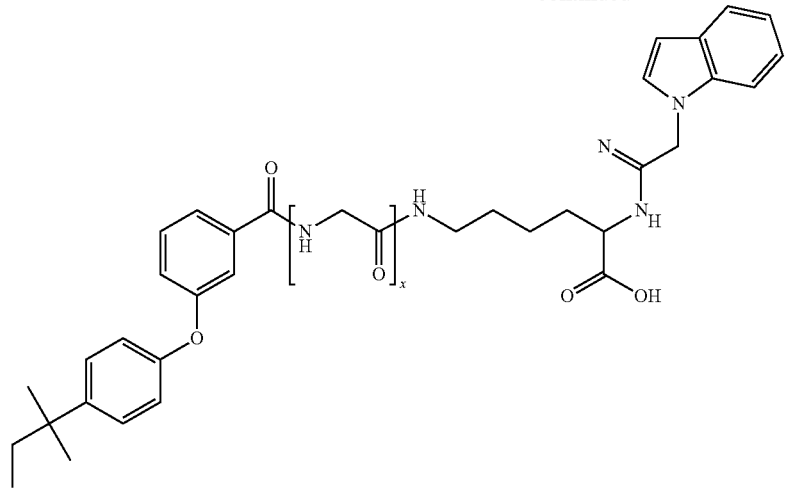
7962GL75866
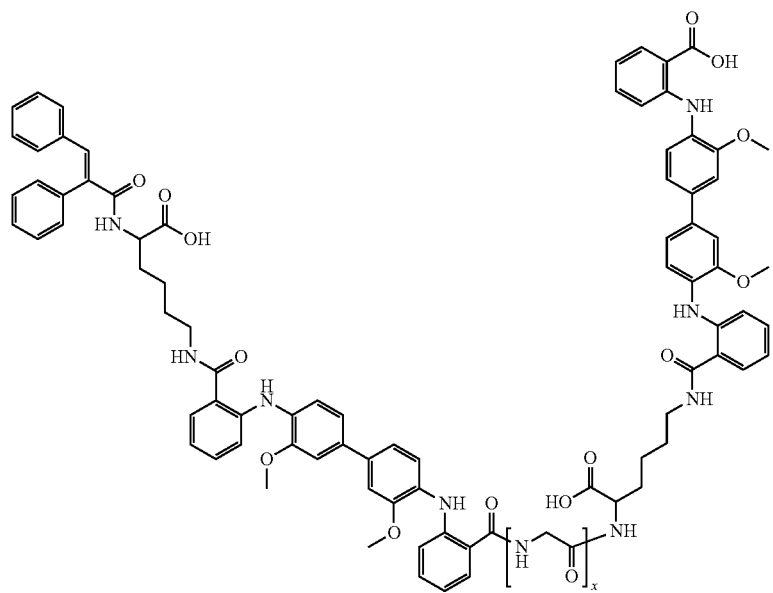
40614L73735GL73735

-continued
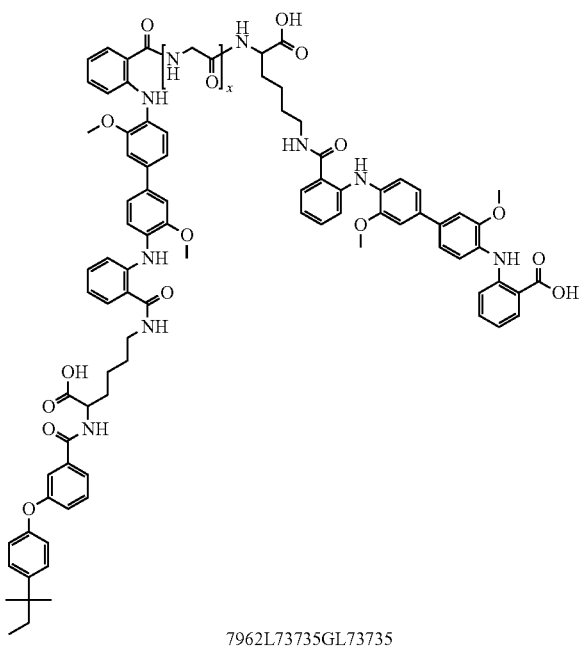
7962L73735GL73735
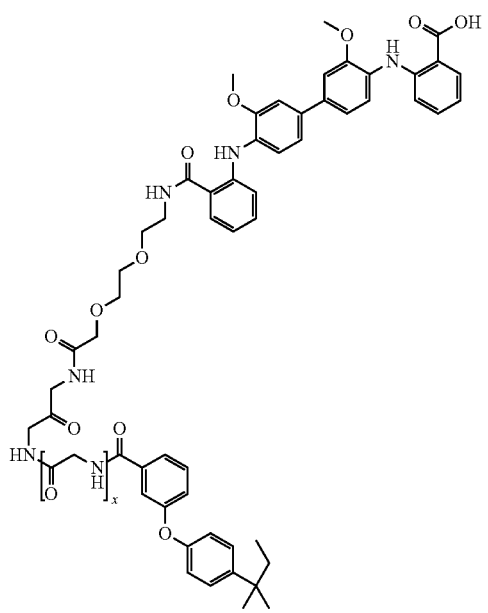
7962GP73735

-continued
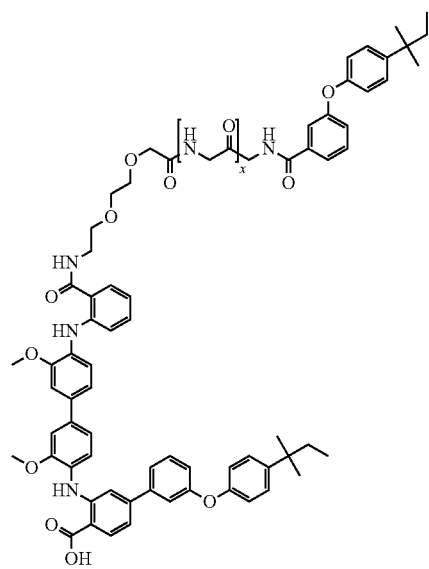
7962GP73735a7962
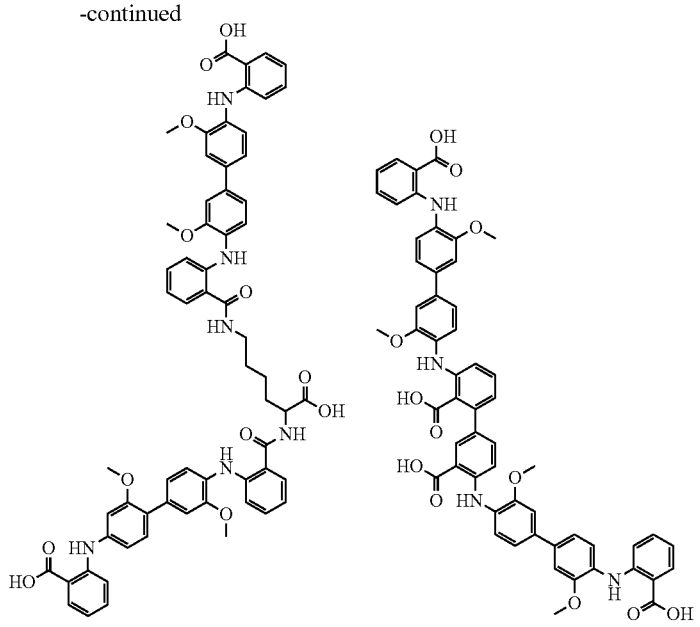
73735L73735
73735a73735
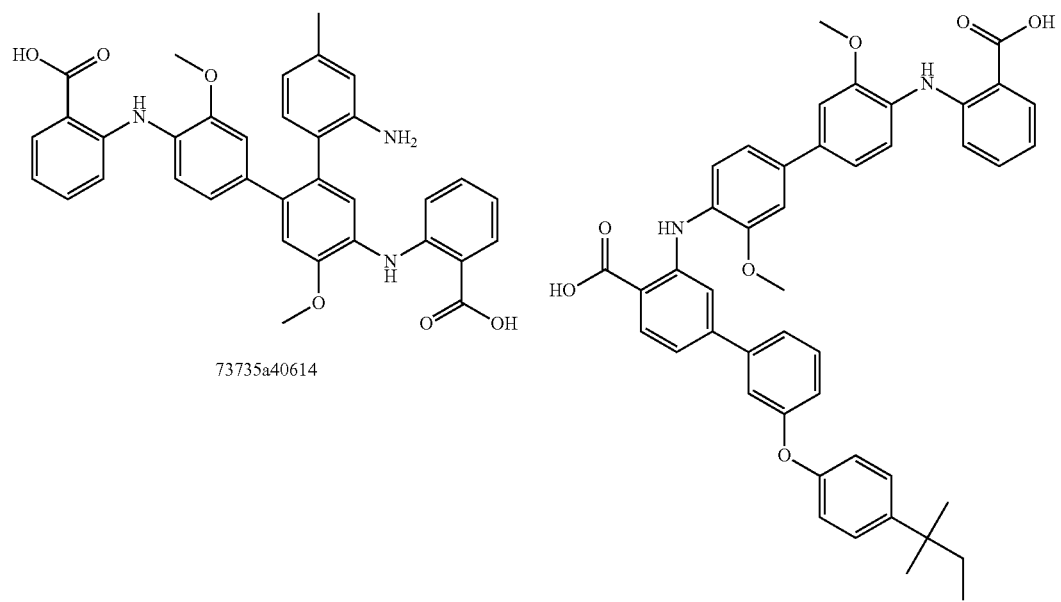
73735a40614
73735a7962

-continued
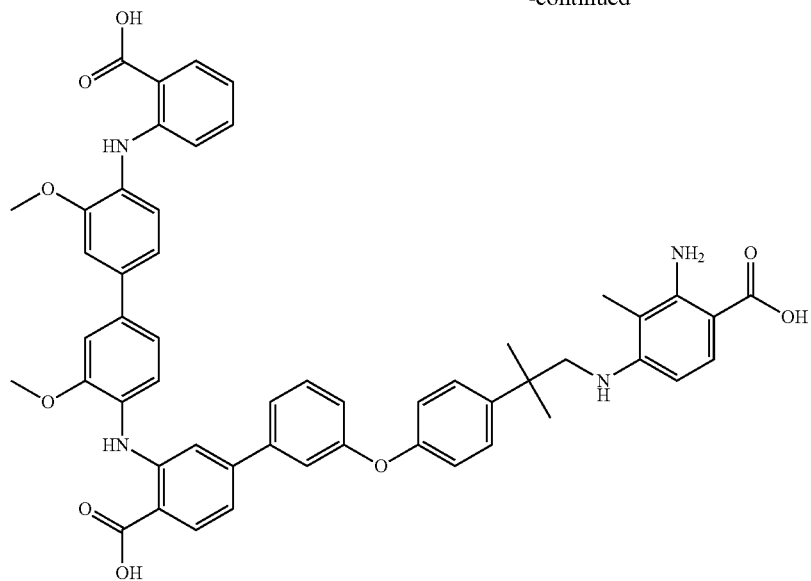
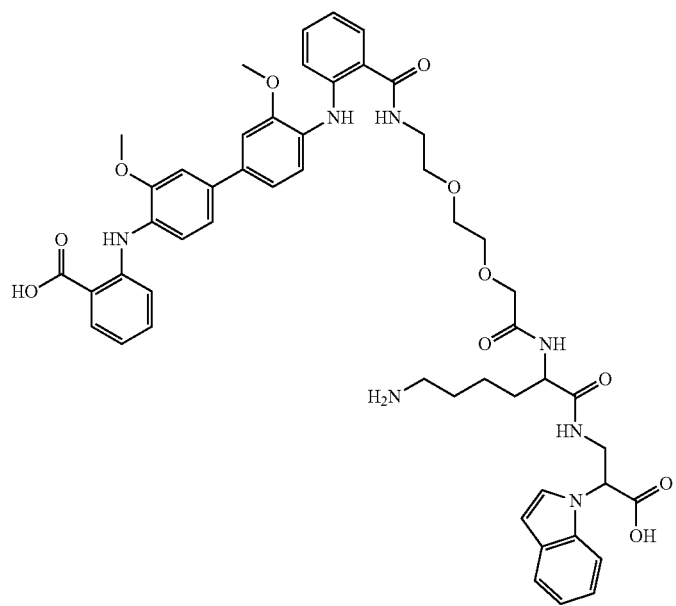

-continued
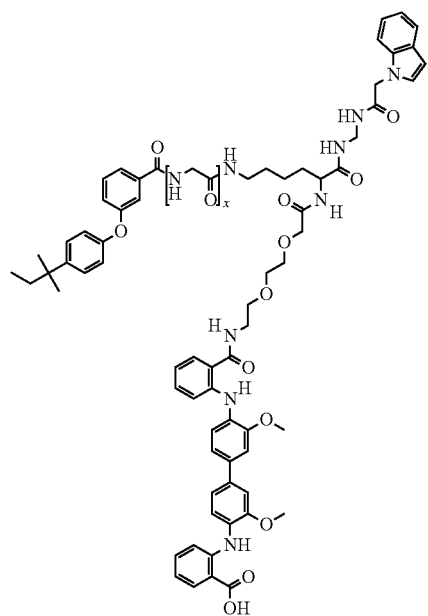
73735Pdam75866LG7962
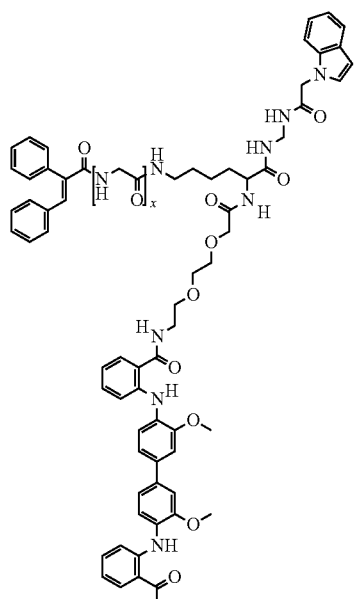
73735Pdam75866LG40614
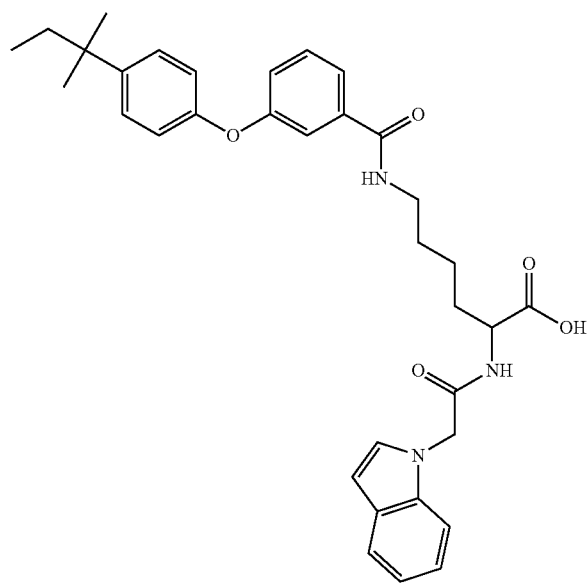
75866L7962

-continued
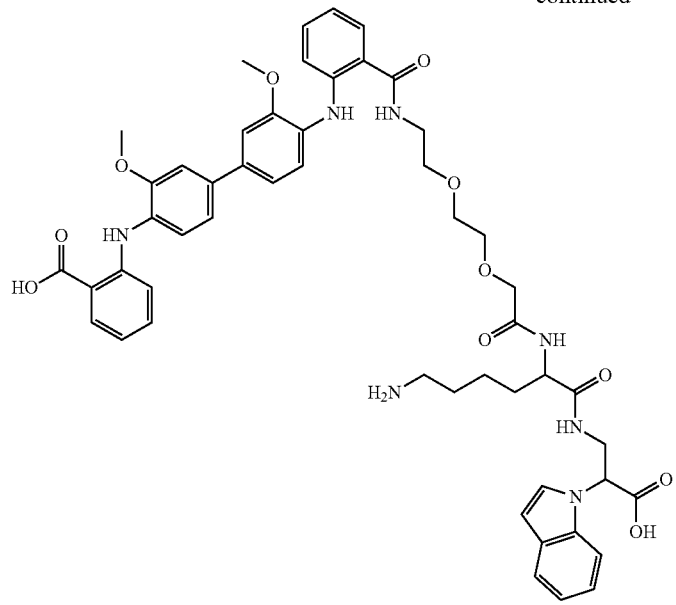
75866LP3735

Ligand Conjugates Binding to CD81 that Inhibit Interaction with *Plasmodium* and HCV The ten ligands described above and moieties or fragments thereof that bind to CD81 may be formulated into conjugates that can block attachment of *Plasmodium* parasites as well as HCV to CD81. Some exemplary conjugates are shown below, but conjugates may be designed that comprise one or more of the ten ligands described above that inhibit *Plasmodium* binding to CD81 or the CD81-binding fragments of these ligands (see FIG. 11) and one, two or more ligands that inhibit HCV binding to CD81.

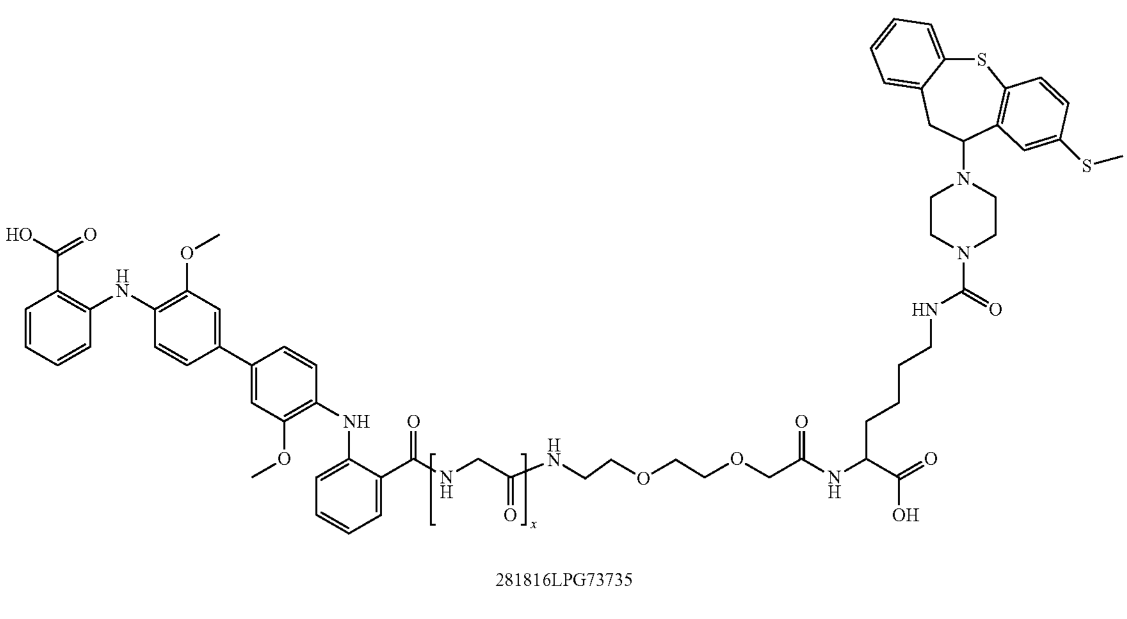

281816LPG73735

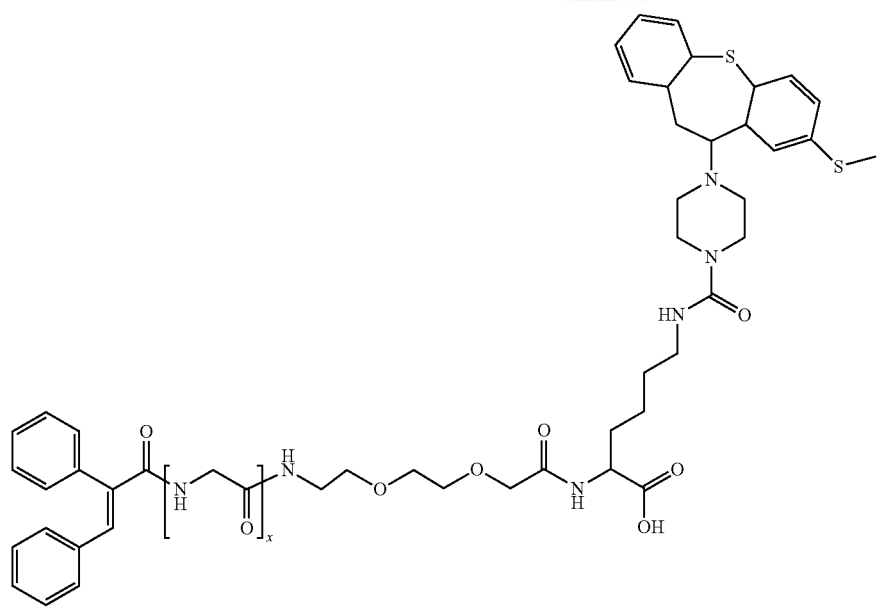
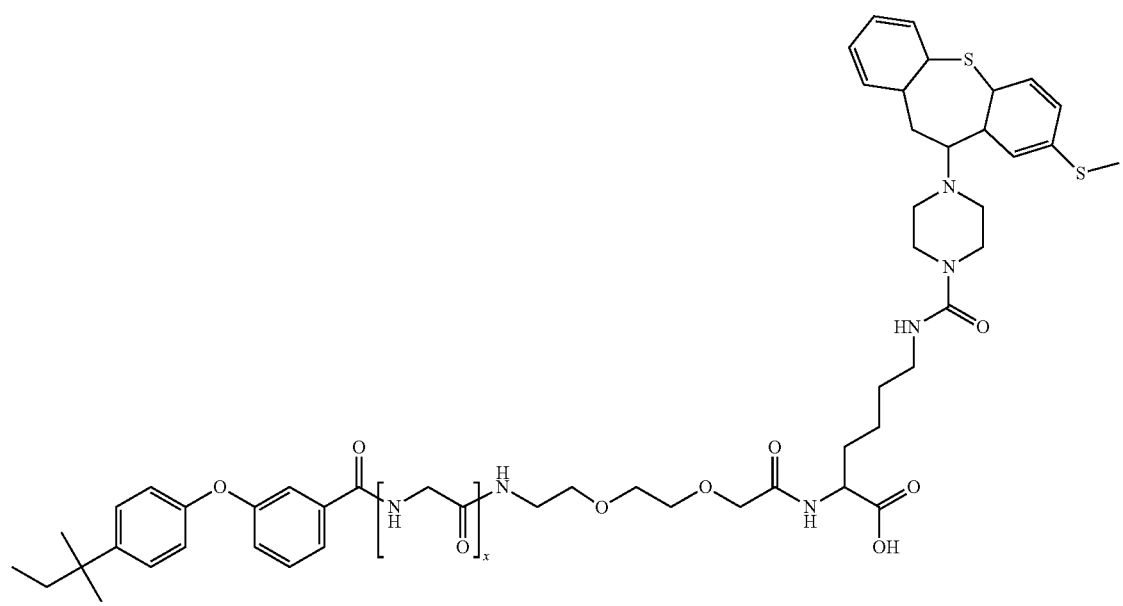

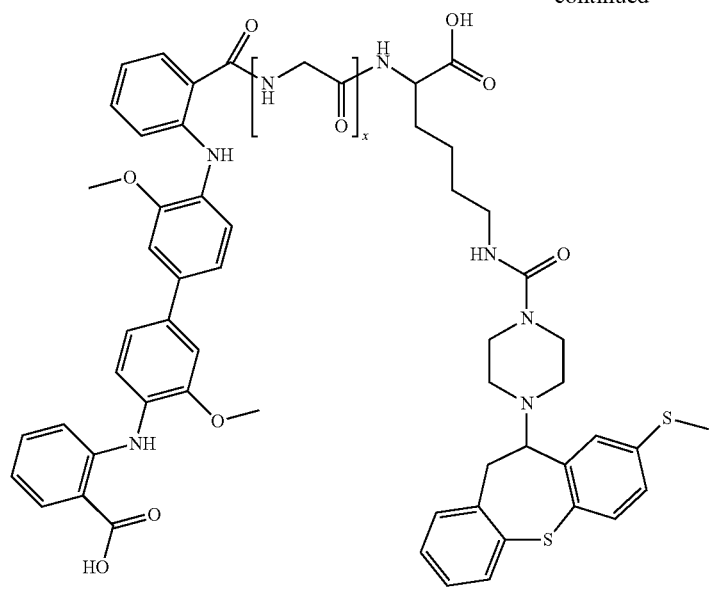
281816LG73735
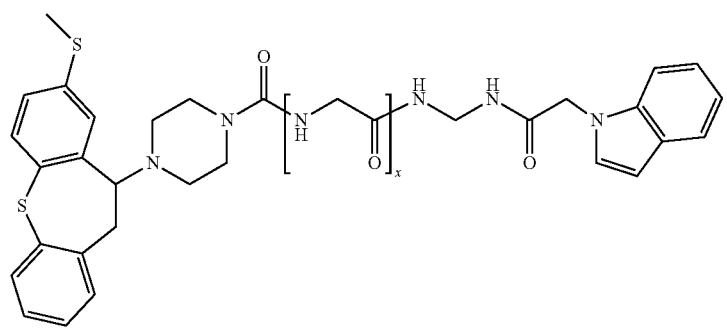
281816G75866
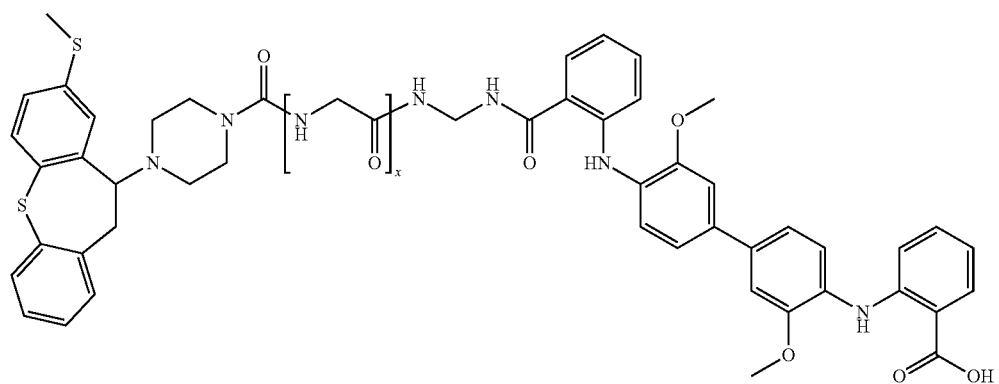
281816G73735

-continued
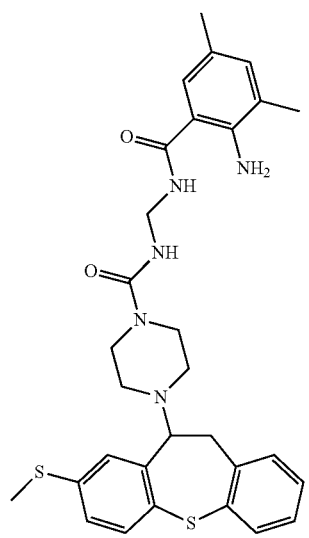
281816dam90444
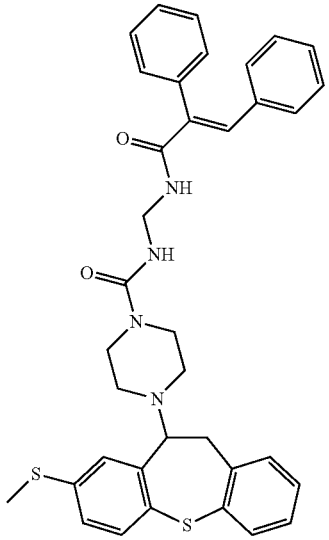
281816dam40614
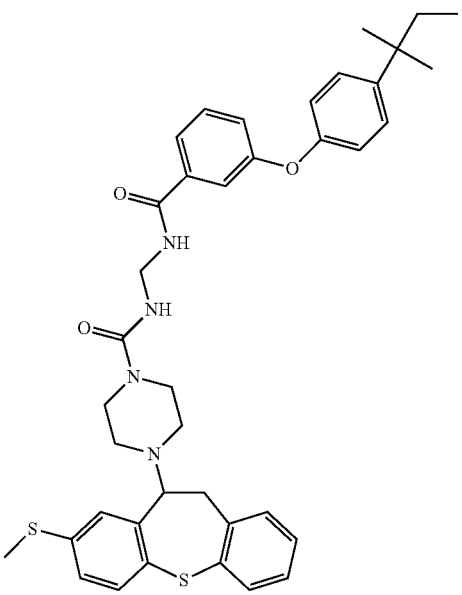
281816dam7962
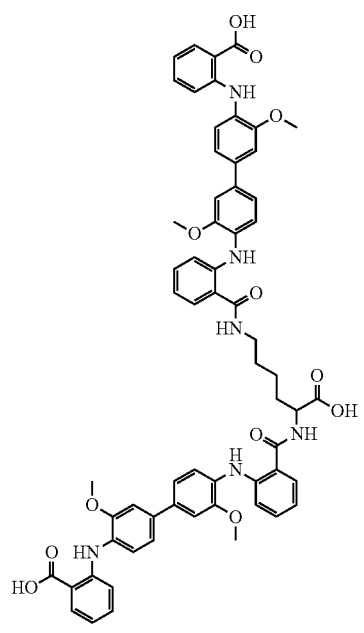
73735L73735

Conjugates of CD81 Ligands containing ligands that inhibit HCV binding to CD81 described by PCT/US2013/071056. Hybrid conjugates comprising one or more small molecule ligands that inhibit *Plasmodium* attachment to CD81 or otherwise interfere with *Plasmodium* pathogenesis as described herein, may further comprise small molecule ligands that inhibit HCV attachment to CD81 or that bind to other parts of CD81 or cellular determinants proximal to CD81.

Small molecule ligands that inhibit the HCV E2 protein binding to CD81 and would be expected to block HCV attachment when conjugated to ligands that block *Plasmodium* attachment to CD81 are incorporated by reference to PCT/US2013/071056 and include the following:

Small molecule ligands that bind to five sites on CD81 (identified by NCI diversity set ligand number). Sites 1-5 below refer to sites on CD81 described by PCT/US2013/071056.

| Site 1 | Site 2 | Site 3 | Site 4 | Site 5 |
|--------|--------|--------|--------|--------|
| 165665 | 38743  | 93033  | 16631  | 68982  |
| 164965 | 156957 | 80807  | 68971  | 75866  |
| 689002 | 127947 | 25368  | 78623  | 90444  |
| 30930  | 73735  | 16162  | 81750  | 148832 |
| 5069   | 55573  | 25678  | 401077 | 601359 |
| 7436   | 41066  | 60239  | 408734 | 142446 |
| 21034  | 11891  | 75866  | 303800 |        |
| 98026  | 63865  | 87504  | 75846  |        |
| 123115 | 408860 | 89720  | 638134 |        |
| 7962   | 362639 | 215276 | 70980  |        |

-continued

Small molecule ligands that bind to five sites on CD81 (identified by NCI diversity set ligand number). Sites 1-5 below refer to sites on CD81 described by PCT/US2013/071056.

| Site 1 | Site 2 | Site 3 | Site 4 | Site 5 |
|---|---|---|---|---|
| 16646 | 36914 | 331931 | 90444 | |
| 106863 | 20586 | 20586 | 89720 | |
| 117922 | 23895 | 403374 | 25678 | |
| 120631 | 252359 | 8481 | 215276 | |
| 7962 | 403374 | 5856 | 16162 | |
| 117922 | | | 60239 | |
| 106863 | | | | |
| 23895 | | | | |
| 120631 | | | | |
| 16646 | | | | |
| 252359 | | | | |
| 134137 | | | | |
| 97538 | | | | |
| 94914 | | | | |
| 31712 | | | | |
| 73170 | | | | |
| 144958 | | | | |
| 153172 | | | | |

Fragment-Based Drug Design

Figure 10A:
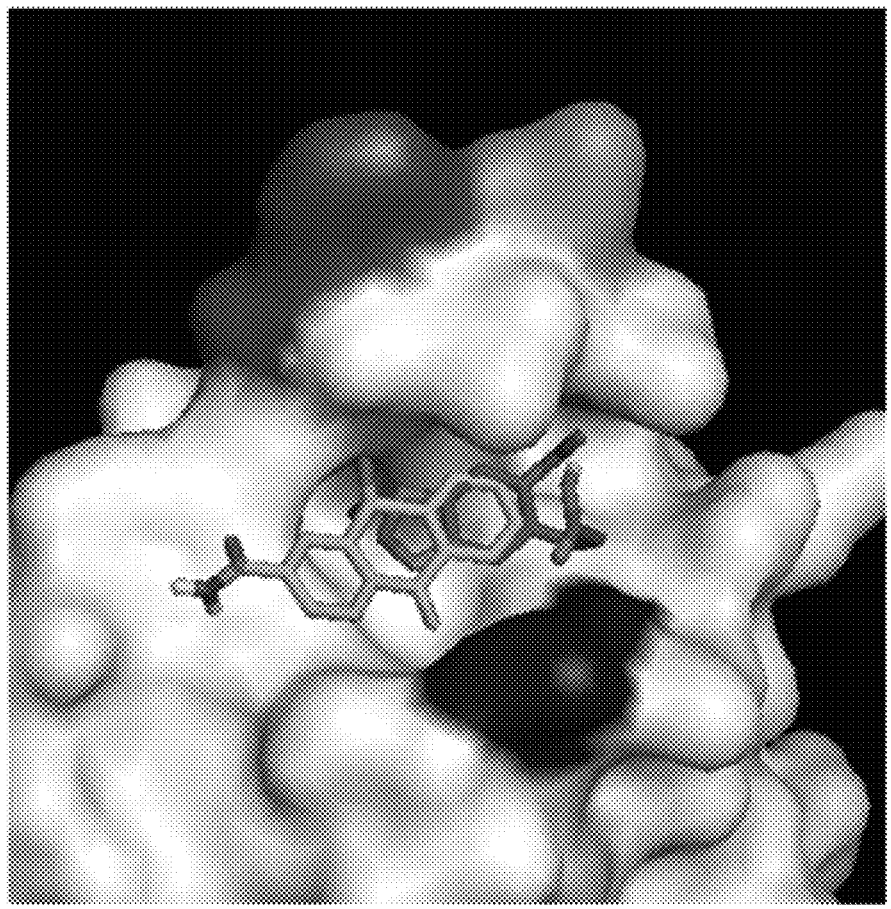
Figure 10B:
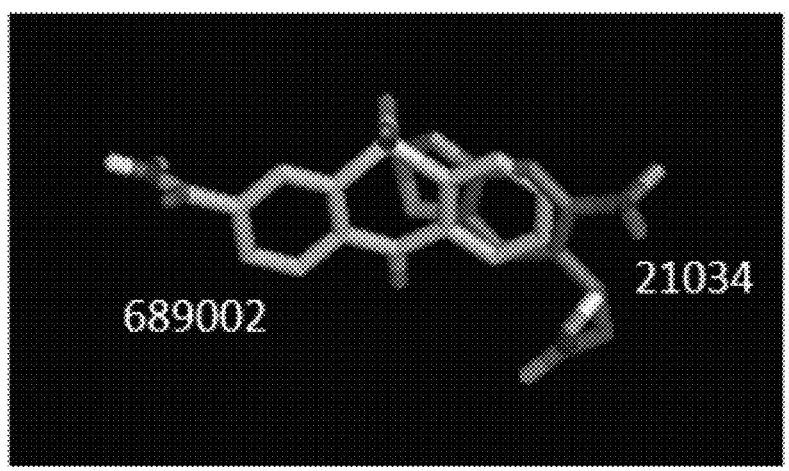
Figure 10C:
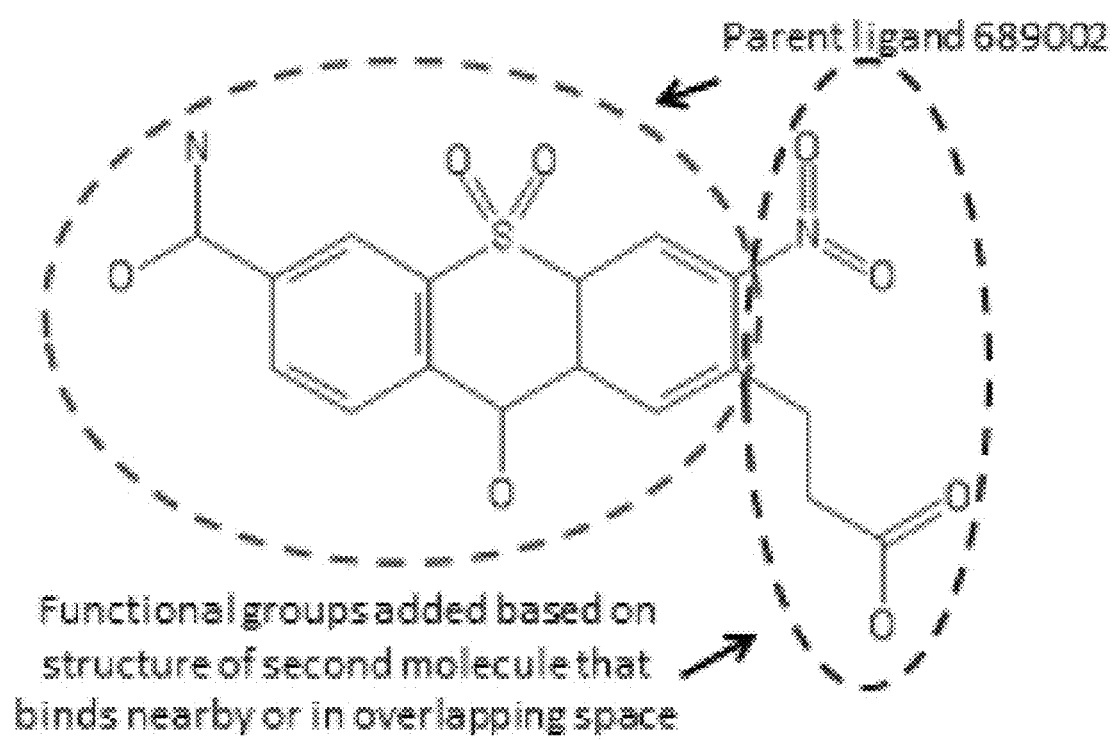
Figure 11A:
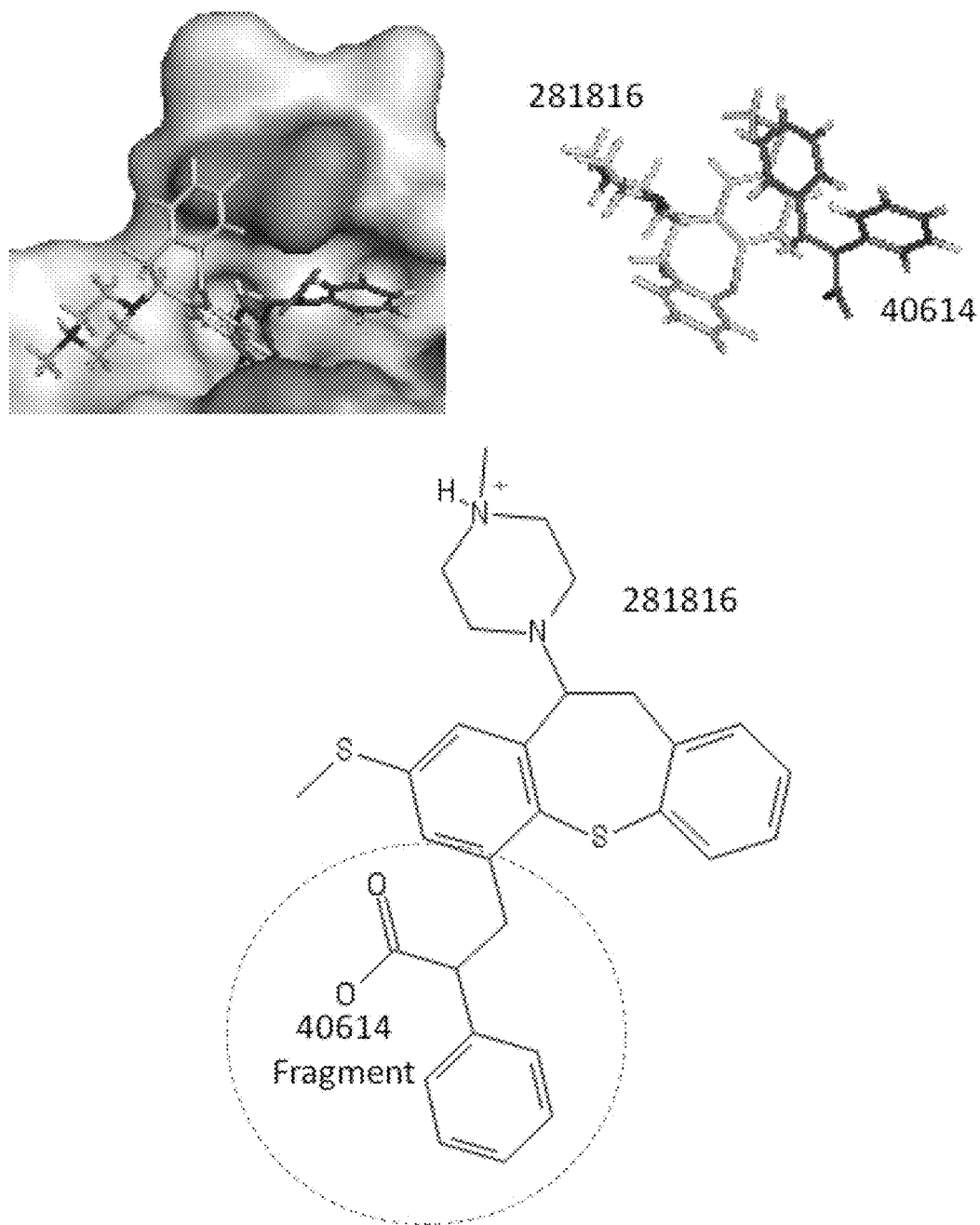
Figure 11B:
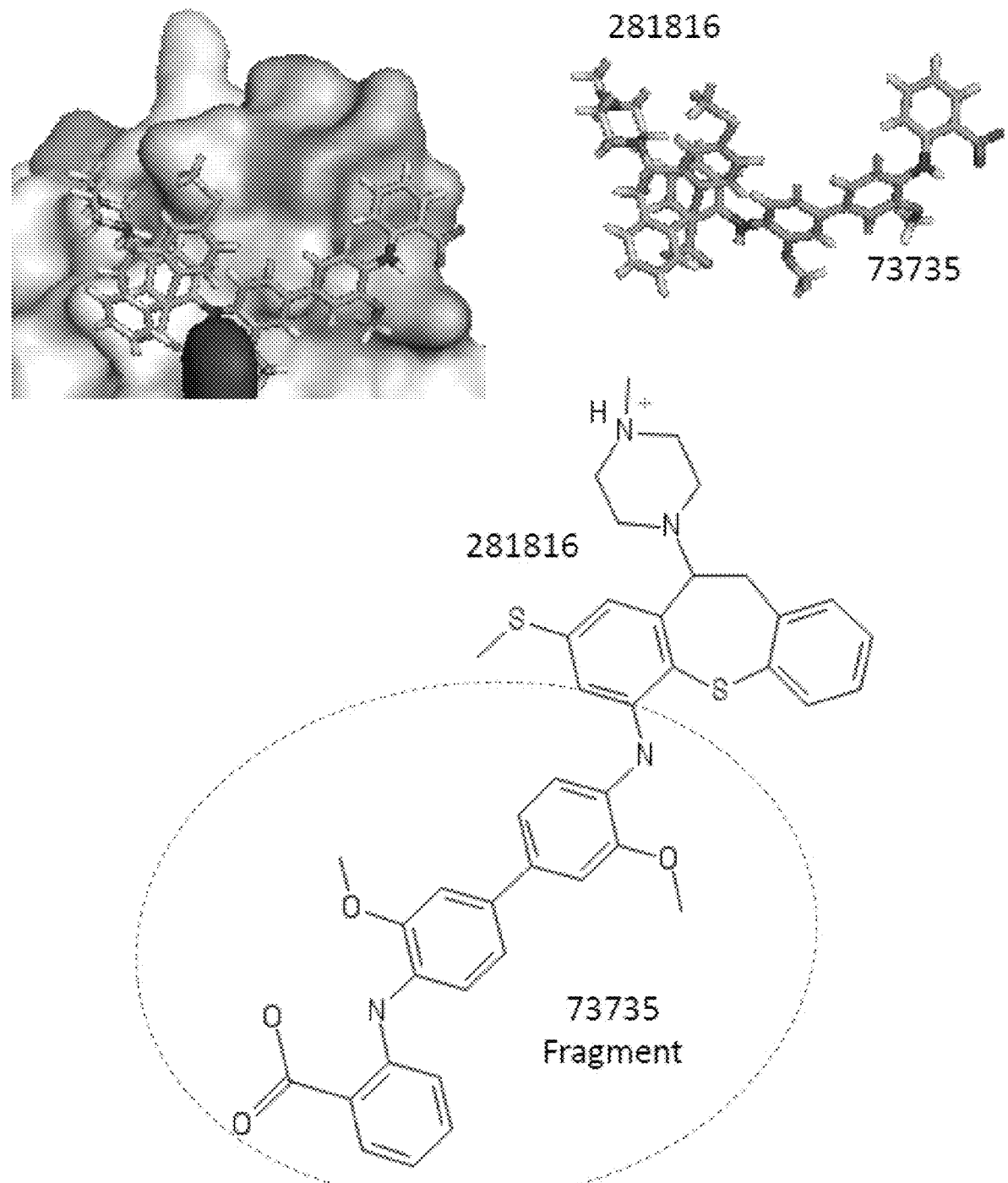
Figure 11C:
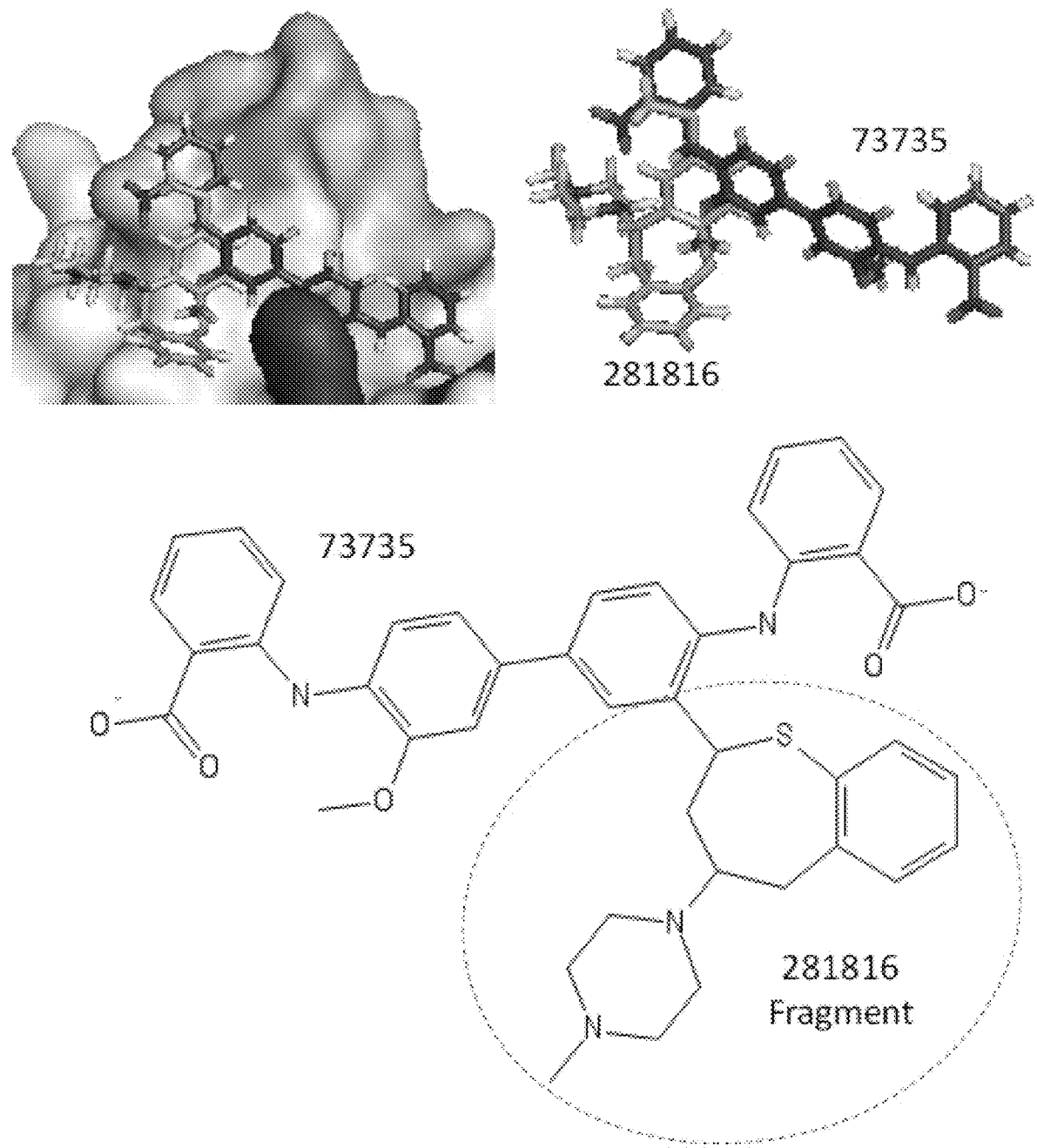
Figure 11E:
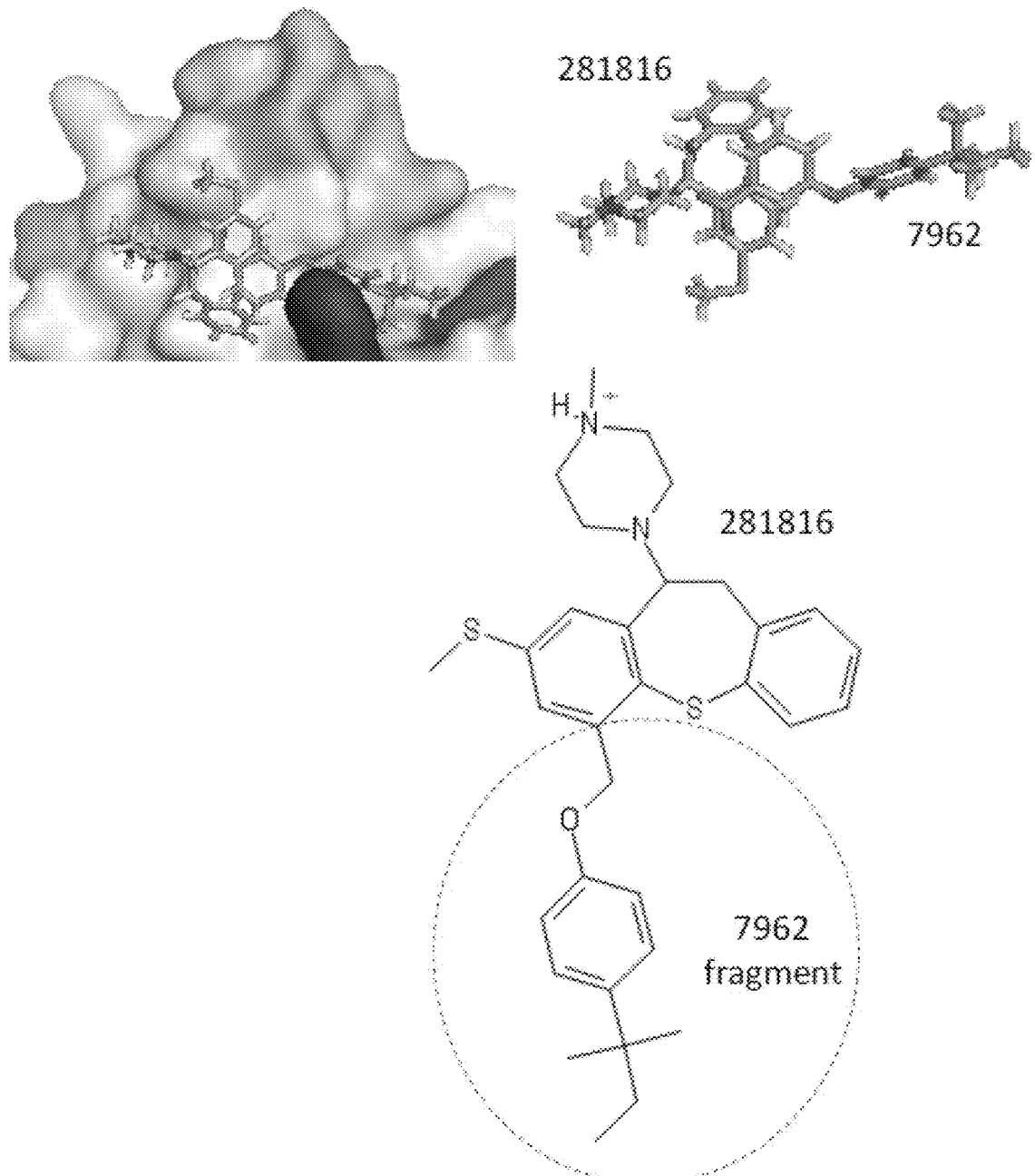
Figure 11F:
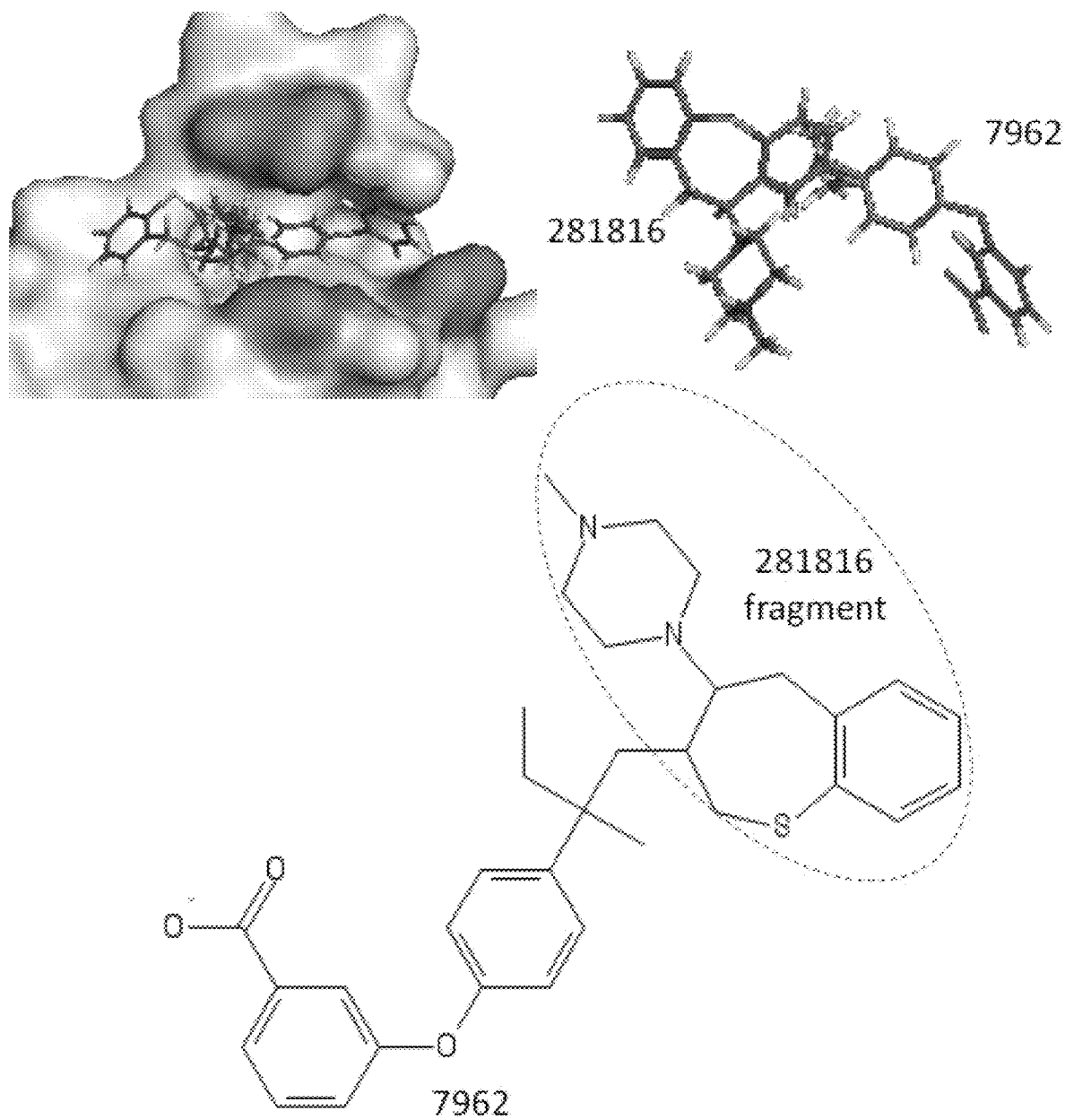
Figure 11K:
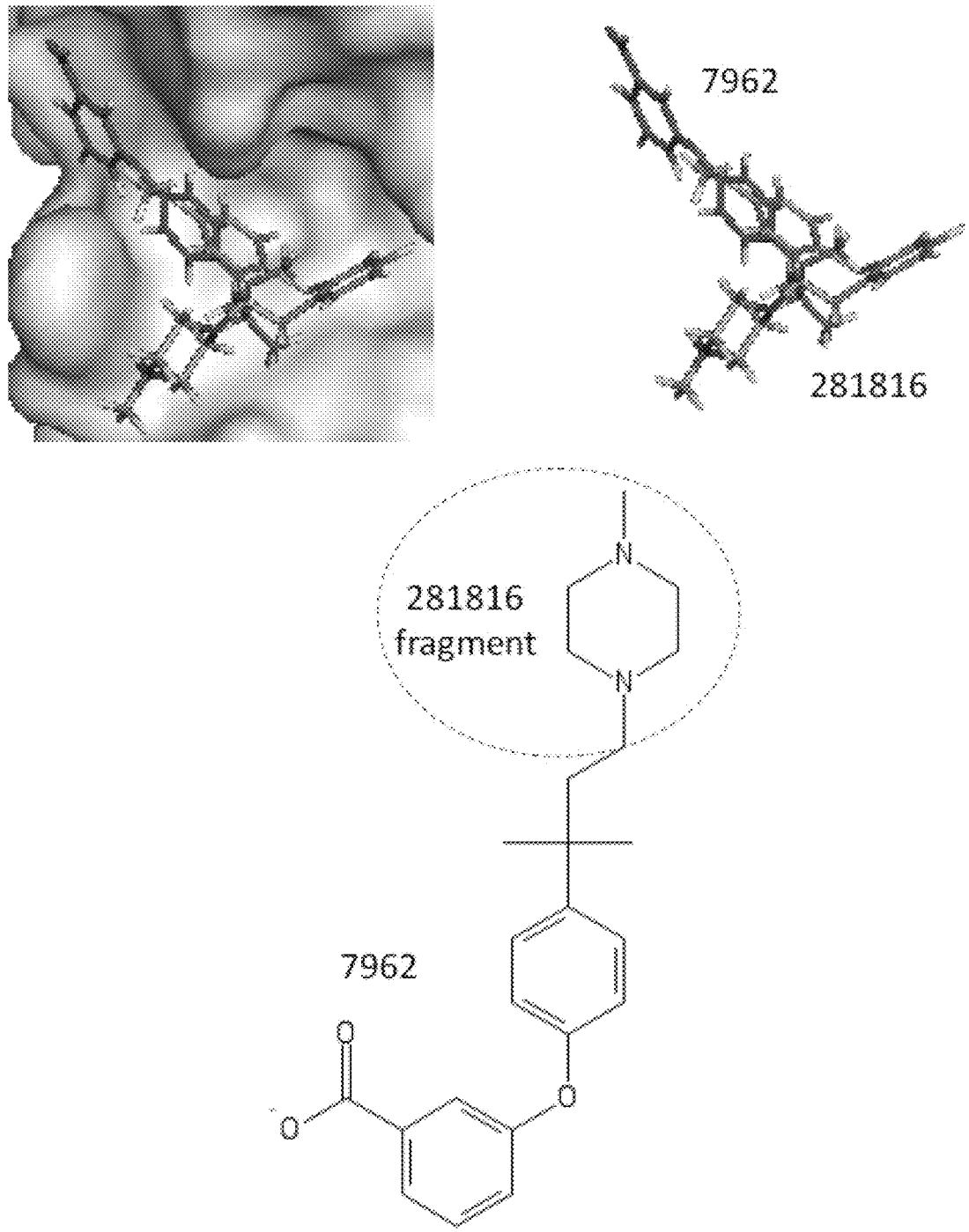
Figure 11L:
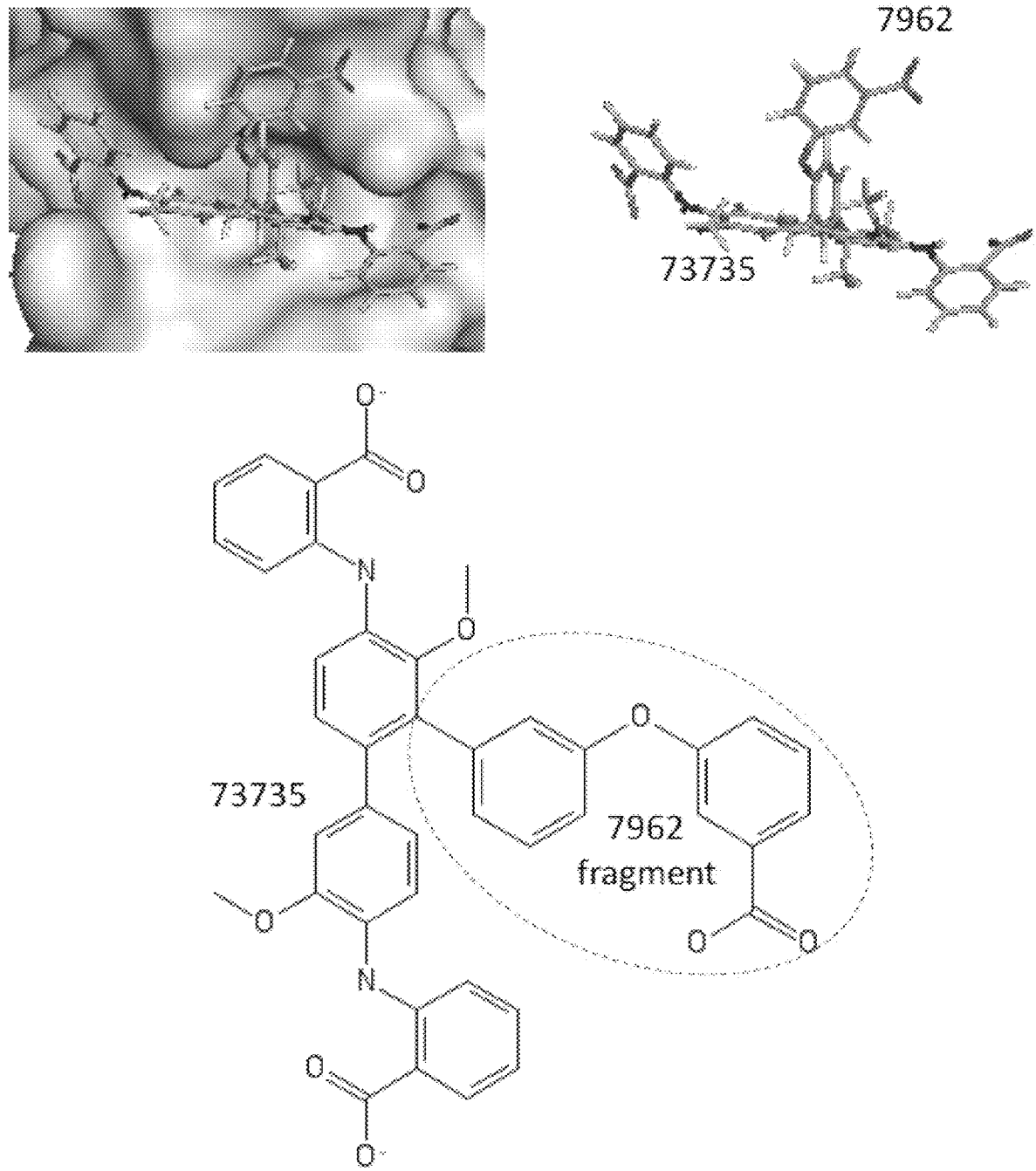
Figure 11M:
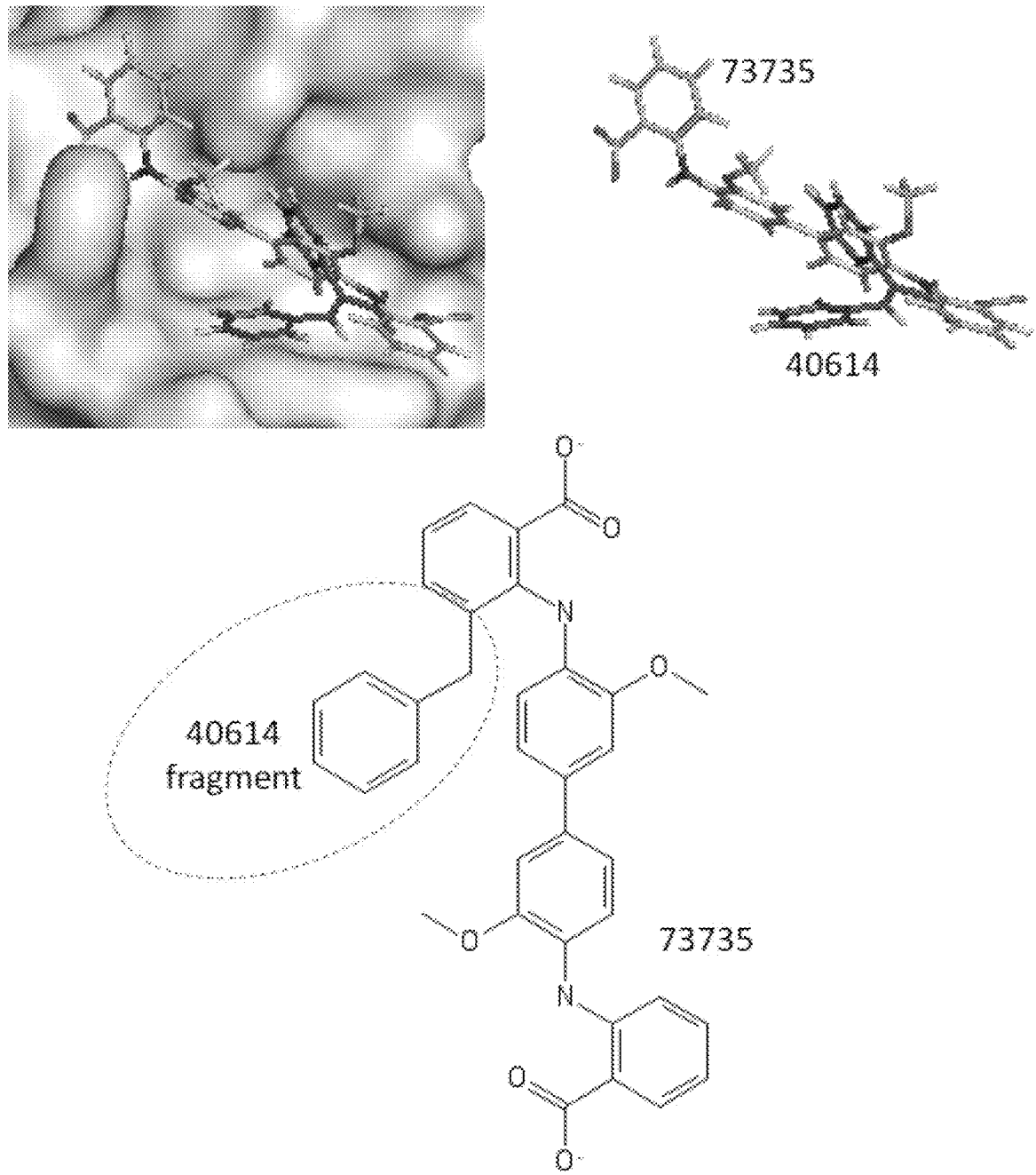

An example of the fragment based design approach used to discover new CD81 ligand analogs and ligand conjugates that bind more tightly to the same sites on CD81 is shown in FIG. 10. Once a set of ligands is confirmed to bind to CD81 using SPR or another experimental method, sets of bound conformers for each ligand generated by docking are examined to identify the ligand conformations that bind to CD81 with the lowest free energy (ΔG) of binding. In those cases where conformers of two different ligands are identified to bind to the same site on the protein, the overlap in binding of conformers of two ligands (in the example shown in FIG. 10, 689002 and 21034) is examined to identify functional groups or molecular fragments that can be added to the end of one ligand (689002 shown here) to provide additional bonding (electrostatic, hydrophobic, van der Waals) to the protein surface and increase both its affinity and selectivity for the target. In the example shown, the parent ligand was chosen to be 689002. Two functional groups on the overlapping bound conformer of 21034, —$NO_2$ and —$CH_2CH_2CO_2H$, bind to amino acid residues adjacent to 689002. Using this information, an analog of the 689002 ligand is created by adding a —$NO_2$ and —CH2CH2CO2H to the phenyl ring of 689002 that overlaps with 21034. When the resulting analog binds to CD81, it would be expected to bind to CD81 using the contacts provided by the parent ligand 689002 as well as the interactions provided by the —$NO_2$ and —$CH_2CO_2H$ groups of 21034.

FIG. 11 provides examples of conjugates produced using CD81-binding fragments of the ten CD81 binding ligands described herein. In each case, pairs of the bound ligands are shown bound to the same binding site on CD81 (left panel). The overlapping structures of the ligands (right panel) are examined to identify functional groups that can be added to one of the two ligands (e.g. 281816 in FIG. 11A) to provide additional contacts and improve binding to the protein. These fragments are circled in graphic formulas (bottom panel) described in FIG. 11. The fragments added can be simple functional groups, such as the benzyl group of 40614 added to ligand 73735 in FIG. 11M, or they can comprise the majority of the structure of another ligand, such as the addition of the 73735 ligand to 281816 in FIG. 11B.

In other configurations 1-10 additional linking atoms may appear between the fragment and the moiety to which it is bound. In the example shown in FIGS. 11I, only part of the overlapping phenyl ring (a —$CH_2$- group) is used to link the fragment of 281816 to ligand 75866. This gives the fragment additional rotational mobility to optimize the added fragment's binding to the protein. Alternatively, 1 or 2 terminal linking atoms in the linkages shown in FIG. 11 may be omitted. In the example analog shown in FIG. 11F, when the 281816 fragment is added to ligand 7962, the terminal methyl group on 7962 is omitted to enable the 281816 fragment to be linked to end of the 7962 ligand.

Figure 9G:
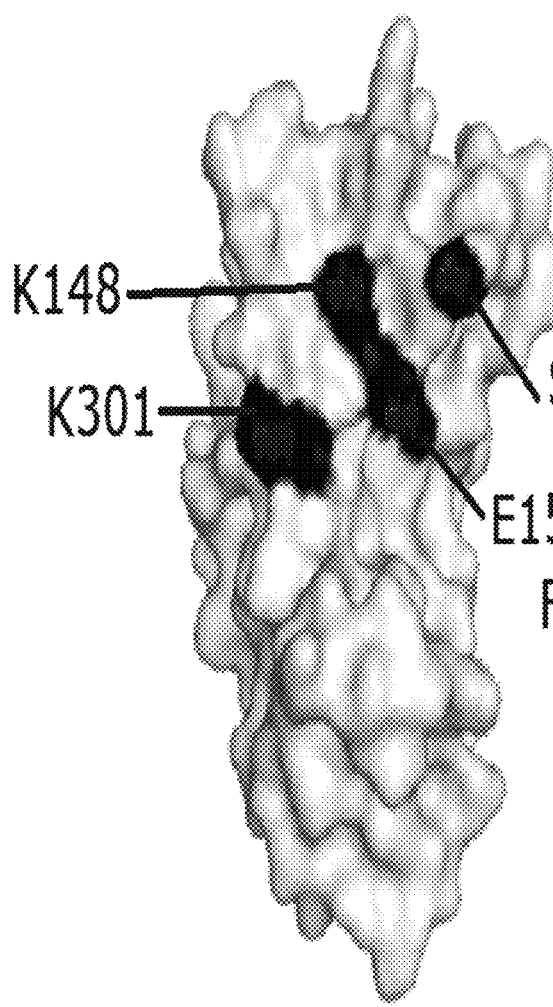
Figure 9H:
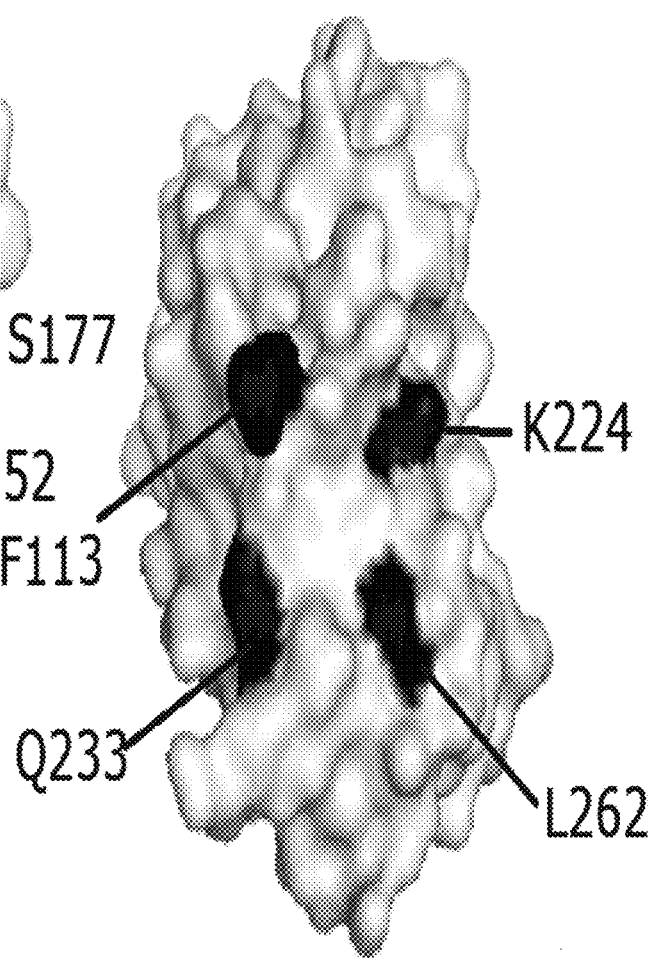

Binding sites on CD81. The inventors have identified ligands that bind to 10 different sites on CD81 shown in the table below. These ligands identify CD81 binding sites to which they bind and can be used to identify other molecules that recognize these sites, for example, CD81 by a competitive binding assay. The CD81 binding sites are described by the ligands identified below which bind to them, by the amino acids surrounding each binding site as shown by FIG. 9.

Small molecule ligand (NCI diversity set ligand numbers)

| | | | | | |
|---|---|---|---|---|---|
| Site 1: | 7962 | 40614 | 73735 | 75866 | 90444 |
| Site 2: | 7962 | 40614 | 73735 | 75866 | 90444 |
| Site 3: | 7962 | 40614 | 73735 | 75866 | 90444 |
| Site 4: | | | 73735 | | |
| Site 5: | | | | | 90444 |
| Site 6: | | | 73735 | | |
| Site 7: | | | | | 90444 |
| Site 8: | | | | 75866 | |
| Site 9: | | | | 75866 | |
| Site 10: | | | | 75866 | |

EXAMPLES

The following non-limiting examples describe experimental procedures and other aspects of the invention.

Preparation of CD81-LEL Structure and Calculation of Binding Sites

The AutoDock suite of programs, developed by Dr. Arthur Olson's molecular graphics laboratory at the Scripps Research Institute, was used to analyze the large extracellular domain of our target protein CD81, prepare surface grid maps, and dock a library of small molecules to CD81. The AutoDock scoring function employs a subset of the AMBER force field, implementing the united-atom model [25]. AutoGrid, a second program included in the AutoDock suite, pre-calculates these grids.

The coordinates for the crystal structure of the open conformation of CD81-LEL (PDB ID: 1G8Q) were obtained from the Protein Data Bank (PDB), AutoDock Tools (ADT) 1.5,6 [25-28] was used to delete water molecules, add polar hydrogens, assign Gasteiger charges, and create grid bounding boxes with a 1 Å spacing for use with AutoLigand and a 0.375 Å spacing for use with AutoDock 4.2. AutoGrid 4.2 was used to pre-calculate grid maps of interaction energies for various atom types and create the map files that were used by AutoLigand to find the CD81-LEL binding sites and by AutoDock for docking. The affinity at each grid point was calculated in AutoGrid by using pair-wise energetic terms with all surrounding atoms which include evaluations for dispersion/repulsion, hydrogen bonding, electrostatics, and desolvation:

$$V = W_{vdw} \sum_{i,j} \left( \frac{A_{ij}}{r_{ij}^{12}} - \frac{B_{ij}}{r_{ij}^{6}} \right) + W_{hbond} \sum_{i,j} E(t) \left( \frac{C_{ij}}{r_{ij}^{12}} - \frac{D_{ij}}{r_{ij}^{10}} \right) +$$

$$W_{elec} \sum_{i,j} \frac{q_i q_j}{\varepsilon(r_{ij})r_{ij}} + W_{sol} \sum_{i,j} (S_i V_j + S_j V_i) e^{(-r_{ij}^2/2\sigma^2)}$$

The weighting constants W have been optimized to calibrate the empirical free energy based on a set of experimentally determined binding constants [28, 29]. The first term, $W_{vdw}$, is a typical 6/12 Lennard-Jones potential for dispersion/repulsion interactions. The parameters are based on the AMBER force field. The second term, $W_{hbond}$, is a directional H-bond term based on a 10/12 Lennard-Jones potential. The parameters C and D are assigned to give a maximal well depth of 5 kcal/mol at 1.9 Å for hydrogen bonds with oxygen and nitrogen, and a well depth of 1 kcal/mol at 2.5 Å for hydrogen bonds with sulfur. The function E(t) provides directionality based on the angle t from ideal hydrogen-bonding geometry. The third term, $W_{elec}$, is a screened Coulomb potential for electrostatics. $W_{sol}$ is a desolvation potential based on the volume of atoms (V) that surround a given atom and shelter it from solvent, weighted by a solvation parameter (S) and an exponential term with distance-weighting factor σ=3.5 Å. A and B are constants that describe the magnitude of the repulsive and attractive terms i and j are the iteration numbers of the atoms being examined. So when i=3 and j=147, all of the forces between atom 3 and atom 147 are being calculated. r is the distance between atom i and j, q is the charge and epsilon is the dielectric constant. σ is the distance weighting factor that is set to: s=3.5 Å [25-27].

Figure 2A:
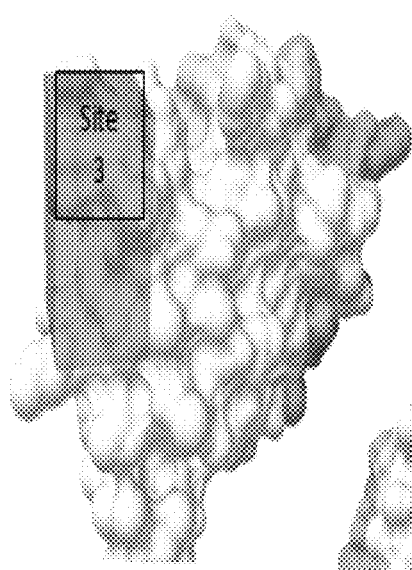
FIGS. 2A, 2B and 2C, respectively depict Sites 3, 2 and 1 which are the initial 3 sites chosen on CD81-LEL to undergo virtual screening runs. Those sites were based on the stretch of 21 amino acids where the site containing those residues was fragmented into 3 subsites and each of them included other residues.
Figure 2B:
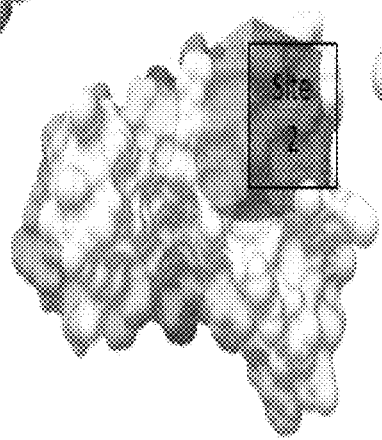
Figure 2C:
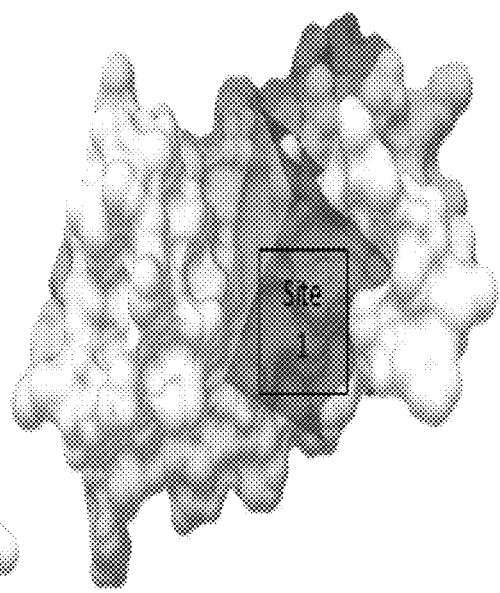
Figure 3A:
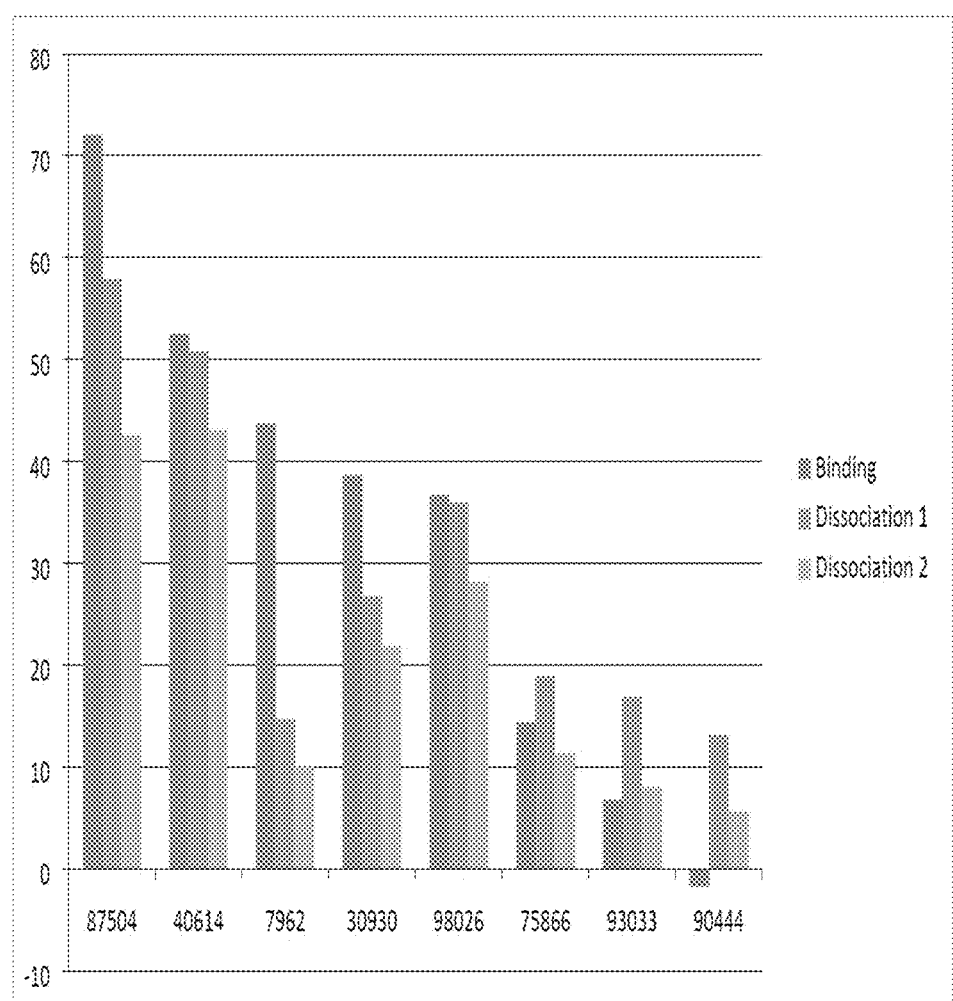
FIG. 3A is a bar chart representing the change in response units of the ligands that were found to bind to CD81-LEL using surface plasmon resonance. The chart shows that 87504 had the best binding-dissociation behavior with CD81-LEL whereas 90444 had the least desirable binding-dissociation behavior.

Three different grid boxes (3 regions) were selected to encapsulate the region of CD81 that collectively contained all 21 of the amino acid residues (135-VVDDDANNAKAV-VKTFHETLD-155) (SEQ ID NO: 5) determined by Yalaoui et al [13] using mutational studies to be required for malaria infection of liver cells. A total of 1597 ligands from the NCI Diversity III Set library were docked against each of these grid boxes in the crystal structure of hCD81 (PDB ID: 1G8Q). The inventors targeted those amino acid residues and cavities on the protein's surface surrounding the amino acids using the 3 grid parameter files (FIG. 2) to guide the virtual screening/docking runs. The top 500 of the lowest energy docked ligands were examined, and we selected the top 31 ligands for experimental testing in vitro using surface plasmon resonance and antibody neutralizing assays to validate ligand binding to CD81.

Virtual Screening

The parameters were set at 100 for the number of genetic algorithm (GA) runs, 150 as the population size, and a maximum number of generations of 25,000. The Lamarckian genetic algorithm in AutoDock was used to perform the docking experiments [30]. Docking results were sorted by the lowest binding energy in addition to specific ligand selection criteria that would facilitate the design and synthesis of the best ligand conjugates. The virtual screening runs were performed using the National Biomedical Computation Resources (NBCR) computer cluster [31]. Vision [32] was used to construct the computational workflows that were used for virtual screening to identify small molecule ligands calculated to bind to cavities on the CD81 protein's surface nearby the key *Plasmodium* contact residues. Clusters of the top 10 ligands were identified to bind to one or more of 10 cavities shown in FIG. 9. The list of small molecules calculated to bind to the sites were ranked according to their calculated free energy of binding, and those with the lowest free energies were further screened manually to identify the best ligand candidates for experimental testing.

Ligand Evaluation

Preference was given to ligands that were calculated to form multiple contacts with atoms or amino acid residues in or around the perimeter of the targeted amino acids. Ligands containing two or more free amino or carboxyl groups were only considered. for use in creating ligand conjugates that might need additional charge to increase their solubility or provide conjugation points when connecting three or more molecules together. Molecules that were highly hydrophobic, highly charged, known to be highly toxic, exist in more than one form (such as enol-keto forms), or contained disulfide bonds were avoided. The calculated binding energy was used to identify the top hits.

Surface Plasmon Resonance

SPR analysis was performed using a Biacore T200 workstation (GE Healthcare, NJ, USA). A recombinant form of the CD81-LEL protein with a GST tag (generously provided by Dr. Shoshana Levy, Stanford University) was used to confirm, using an established experimental technique, the binding of several ligands to the protein. Briefly, 10 μM CD81-LEL-GST diluted into 10 mM Na-Acetate buffer pH 4.5 was immobilized for 15 min at a flow speed of 5 μl/min onto a CM5 sensor chip using amine-coupling (EDC-NHS), Approximately 20,000 RU of protein were immobilized on the chip. The ligands were prepared as 600 μM solutions in PBS-0.05% Tween-80 (the running buffer) and they were introduced to the protein using a pre-programmed 3 minute association and 1 minute dissociation interval.

The binding affinity of the most tightly bound ligand in the group selected for ligand conjugate design (Ligand 1) was estimated using data collected from a series of SPR binding experiments conducted at different ligand concentrations. To obtain the kinetic and affinity data needed to estimate the Kd, the original ligand was diluted serially with running buffer to produce seven different ligand concentrations: 1024 μM, 516 μM, 256 μM, 128 μM, 64 μM, 32 μM and 0 μM. Data were fitted using a monovalent binding model.

Dual Polarization Interferometry Analysis

DPI analyses were performed using an AnaLight 4D workstation (Farfield Group, Manchester UK). The recombinant CD81-LEL was immobilized onto a Thiol AnaChip using Sulfo-GMBS as a cross-linker in PBS running buffer. Non-specific sites were blocked with digested casein. TRIS was used to cap the cross-linker, blocking any additional amines from covalently binding to the cross-linker on the chip surface. Ligands were prepared as a 20 mM stock solutions in DMSO. Each ligand was diluted to a final concentration of 500 μM in PBS just prior to injection (final DMSO concentration was 2.5%), PBS and DMSO mixed in the same ratio were used as a blank. Data collection and analysis were performed using the AnaLight Resolver.

In Silico Design of Conjugated Ligands

Combinations of ligands used to design the ligand conjugates were selected using three criteria: 1) their calculated free energy of binding to CD81-LEL, 2) their orientation when bound on the protein's surface (as assessed by docking), and 3) their binding nearby another ligand to which it could be linked. Using the structure of the bound ligand-CD81-LEL complexes calculated by AutoDock, the distance between the carboxyl or amino groups on neighboring ligands was estimated and a linker of suitable length was designed using a combination of lysine, dimethylaminomethane and miniPEG molecules. The linker spacing was optimized by incorporating PEG moieties between the ligands to adjust the length of the linker, by inserting lysine residues at key points to enable linker branching [23, 24], and by incorporating diaminoalkanes or dicarboxylic acids when needed to link two ligands by their carboxyl or amino groups.

Figure 1B:
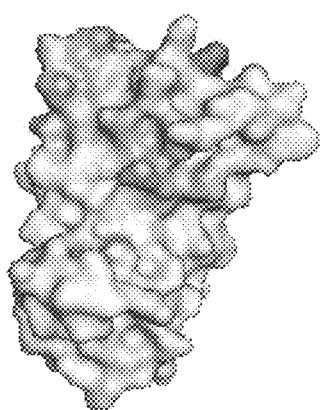

Thirty-one ligands from the virtual screening runs were selected to be the first set for conducting experimental validation using surface plasmon resonance. Ten of the virtual screening hits were found to bind to CD81 using surface plasmon resonance, Ligand 87504, one of the ligands showing the best binding and dissociation, was predicted by AutoDock and subsequent docking runs conducted with SwissDock to bind to several residues in the stretch of 21 amino acid residues identified by Yalouli et al (13) to be involved. in the *Plasmodium*: CD81-LEL interaction (FIG. 1).

These eight ligands, and two additional ligands 73735 and 281816 identified in subsequent docking and binding studies, were further tested using antibody neutralizing assays and were found to inhibit anti-CD81 binding to CD81-LEL in a dose dependent manner where the 400 uM concentration gave better inhibitory effect compared to the 100 uM concentration, inhibition of the CD81 antibody binding to CD81 by the ligands ranged from 17% to ~30%. Nine of these ligands have been tested to date to determine if they would block the infection of liver cells by *Plasmodium*. Four of the ligands were found to be effective in blocking *Plasmodium* infection of liver cells.

There are three features of 7962 and 73735 (the two most effective ligands that block sporozoite infection) that docking experiments suggest distinguish them from 90444 and 75866 (ligands that block but are less effective): (i) 7962 and 73735 conformers, in general, bind more strongly to CD81 (1-3 kcal/mole). (ii) The strongest binding 7962 and 73735 conformers bind to the red site A (FIG. 7, FIG. 8). (iii) The higher number of 7962 and 73735 conformers are predicted to bind to or nearby Asp137; where none of the 90444 or 75866 conformers were predicted to bind near or to Asp137 which was shown to be essential for infection.

Collectively, these data identify ligand 7962 as a lead drug compound for treating disease caused by several species of malaria parasite.

Experimental Procedures

In Silico Analysis

To perform in silico analysis, the inventors used three different grid boxes (3 regions) to encapsulate the region of CD81 that has the amino acid. residues involved in malaria infection of liver cells. A total of 1597 ligands from the NCI Library were docked against each of these grid boxes in the crystal structure of hCD81 (PDB ID: 1G8Q). This was followed by analyzing the results (filtering, visually inspecting and determining virtual screening hits. Thirty one hits were chosen to be tested in vitro.

Surface Plasmon Resonance

SPR analysis was performed using a Biacore T100 workstation (GE Healthcare, NJ, USA). A recombinant form of the CD81-LEL protein with a GST-tag (Shoshana Levy Lab-Stanford) was used to determine the binding affinities of the 31 ligands, 10 uM CD81-LEL-His diluted into 10 mM sodium acetate buffer pH 4.5 was immobilized for 15 min at a flow speed of 5 ul/min onto a CMS sensor chip using amine coupling (EDC-NHS). Approximately 20,000 RU of protein were immobilized on the chip. The ligands were prepared as 200 uM solutions in PBS-1% DMSO (the running buffer) and they were introduced to the protein using a pre-programmed 3 min association and 1 min dissociation interval.

Antibody Neutralizing Assays

For antibody neutralization assay Raji cells were used, a human B cell line that expressed high amounts of CD81 on the surface (data not shown), Cells were grown in RPMI medium (10% FCS, 1% penicillin/streptomycin, 1% L-glutamine, 1% non-essential amino acids, 1% sodium pyruvate, pH 7.4, at 37° C. with 5% $CO_2$). $2\times10^5$ cells were incubated with or without different concentrations (50 μM, 100 μM, 400 μM and 1 mM) of indicated inhibitor for 20 min at room temperature, subsequently 1 ul (16 ng/μl) of FITC-labeled anti CD81 antibody (BD Pharmingen, 551108) was added to the cells and incubated for 20 min (antibody titration was performed to obtain a working dilution range, data not shown). Cells were washed and analyzed by FACS (BD FACSCalibur, software: Cell Quest Pro). Mean Fluorescence Intensity MFI was calculated using Flowjo software (TreesStar, www.flowjo.com).

Mosquito Infection.

*Anopheles stephensi* mosquitoes were fed on mice infected with *Plasmodium yoelii* 17XNL parasites. On day 14 post bloodmeal, salivary glands were harvested, homogenized, sporozoite number was determined using a hemocytometer and the indicated number of sporozoites was added to cell monolayers, *Plasmodium falciparum* sporozoites were generated by membrane feeding *An. stephensi* mosquitoes using gametocyte cultures generated in vitro.

Cells and Antibodies

HepG2-CD81 (14) cells were maintained in DMEM supplemented with 10% fetal calf serum and 1 mM glutamine (DMEM/FCS), mAb 2E6 was used for development assays and is directed against *Plasmodium* Hsp 70 (15) and mAb 2A10 is directed against the repeat region of *P. falciparum* CSP and was used for invasion assays.

Invasion and Development Assays $5\times10^5$ HepG2-CD81 cells were plated on collagen coated Lab-Tek wells and allowed to adhere overnight. The following day, cells were preincubated with 400 uM of compound for 30 minutes at 37° C. Controls were pre-incubated with DMSO at the same concentration in which it was found in the compound solutions. $10^5$ sporozoites were added to each well and in the case of *P. falciparum*, incubated for 1.5 hours and scored for invasion whereas in the case of *P. yoelii*, incubated for 44 hours and scored for exoerythrocytic stages.

Results

Eight out of 31 ligands were found to bind to CD81 using surface plasmon resonance based assays (Table 1—FIG. 3A). Two additional ligands that were found in earlier experiments to bind to CD81-LEL using SPR (FIG. 3B), 73735 and 281816, were also found to bind near the 21 residue peptide sequence required for *Plasmodium* infection in a second round of ligand docking experiments using SwissDock.

TABLE I

Surface Plasmon Resonance Experiment. This table shows the change in response units in relation to binding and dissociation of the 8 ligands that were tested.

| Ligand ID | Binding | Dissociation 1 | Dissociation 2 |
|---|---|---|---|
| 87504 | 72 | 57.9 | 42.6 |
| 40614 | 52.5 | 50.8 | 43 |

TABLE I-continued Surface Plasmon Resonance Experiment. This table shows the
change in response units in relation to binding and dissociation
of the 8 ligands that were tested.

| Ligand ID | Binding | Dissociation 1 | Dissociation 2 |
|---|---|---|---|
| 7962 | 43.6 | 14.7 | 10.1 |
| 30930 | 38.6 | 26.8 | 21.8 |
| 98026 | 36.6 | 35.9 | 28.1 |
| 75866 | 14.3 | 18.9 | 11.3 |
| 93033 | 6.7 | 16.8 | 7.9 |
| 90444 | −1.7 | 13.1 | 5.6 |

Ligand 87504 was found to be the one with the most desirable binding-dissociation behavior (highest binding RU and slowest rate of dissociation). Ligand 90444 and 93033 are considered of comparable binding and dissociation.

In addition, four of the ten ligands had an inhibitory effect on the CD81: antibody interaction (Table 2). As shown, they were found to have a better inhibitory effect at concentration of 400 uM when compared to that of 100 uM.

TABLE 2

Inhibition of JS-81 antibody binding to native CD81 on Raji
cells by ligands identified by SPR to bind to CD81.Ligand
Inhibition of JS-81 Binding (%)

| Ligand | 50 µM | 100 µM | 400 µM |
|---|---|---|---|
|  | 0 | 1 | 31 |
| 23895 | 0 | 0 | 17 |
| 73735 | 0 | 0 | 24 |
| 7962 | 0 | 0 | 19 |
| 87504 | 0 | 6 | 20 |
| 90444 | 0 | 0 | 24 |
| 25678 | 0 | 4 | 19 |
| 40614 | 0 | 8 | 26 |
| 98026 | 0 | 0 | 21 |
| 134137 | 0 | 6 | 26 |
| 7436 | 0 | 12 | 11 |
| 30930 | 0 | 0 | 14 |
| 127947 | 0 | 0 | 24 |
| 106863 | 0 | 0 | 19 |
| 117922 | 0 | 12 | 26 |
| 144958 | 0 | 54 | 12 |
| 68982 | 0 | 13 | 15 |
| 75846 | 0 | 0 | 52 |
| 698002 | 0 | 0 | 14 |
| 93033 | 0 | 0 | 16 |

Figure 4A:
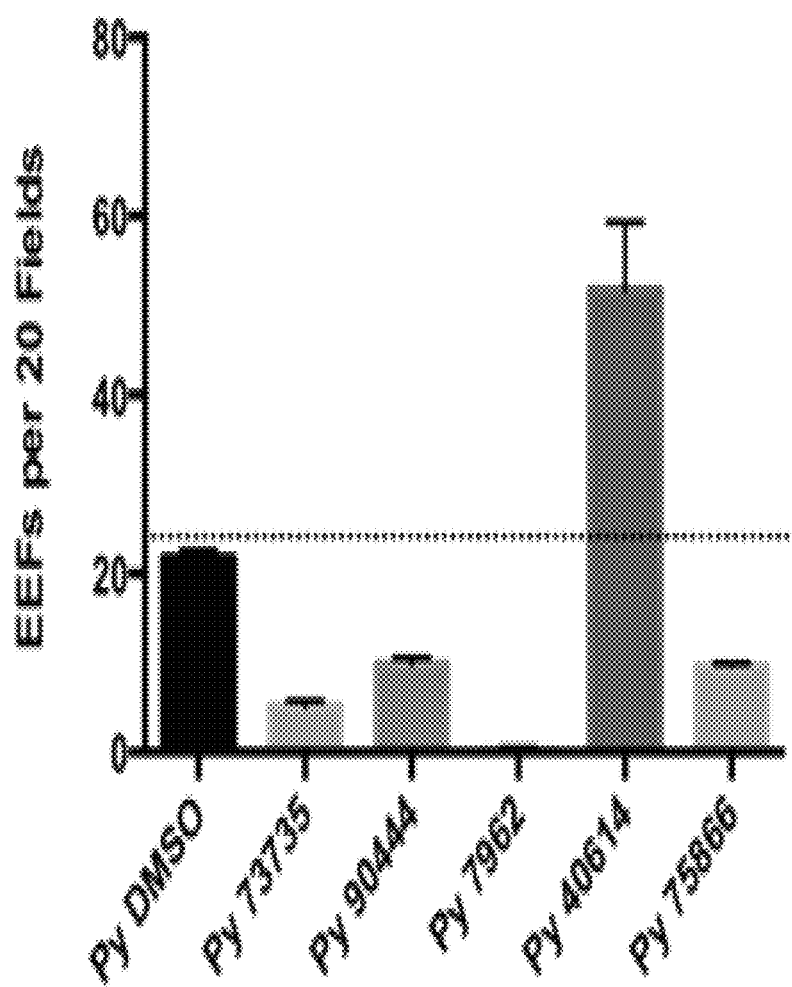
Figure 4B:
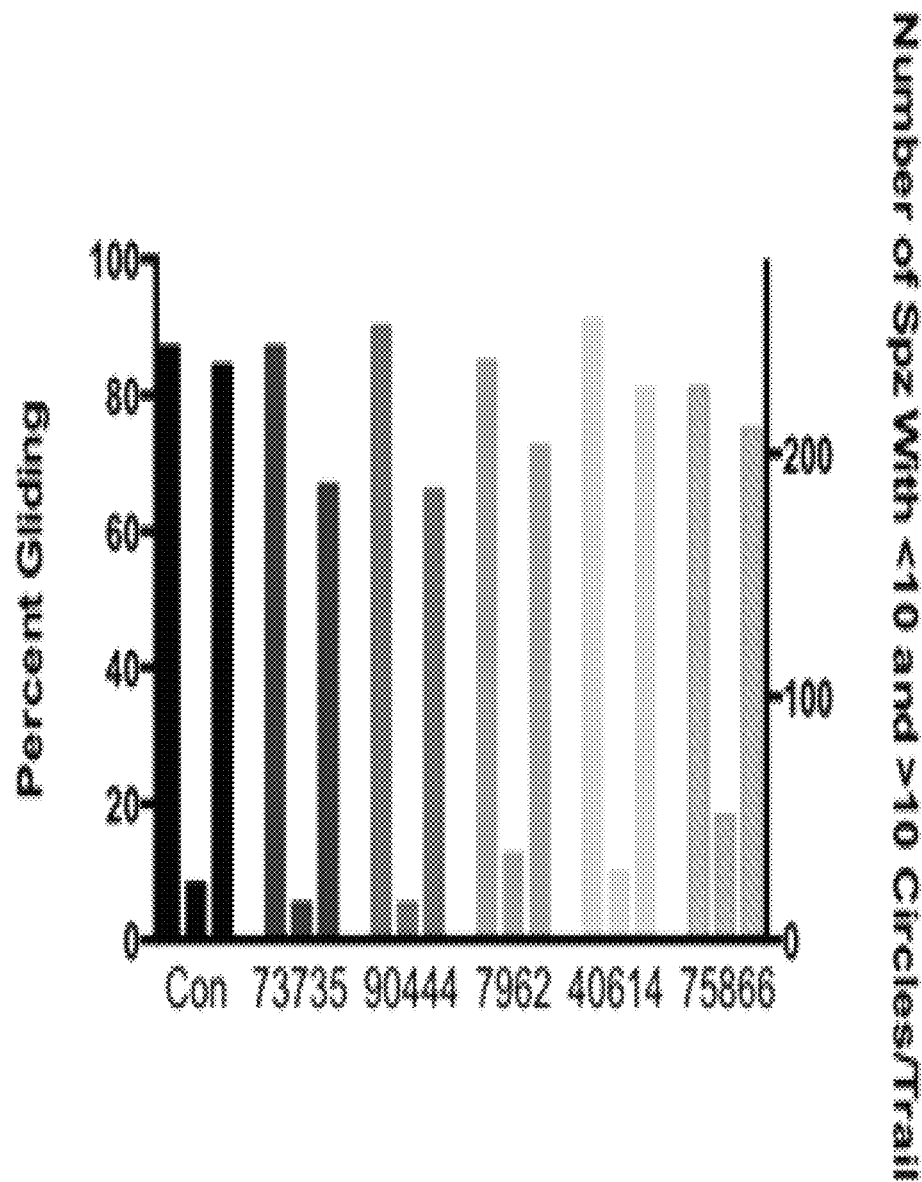
Figure 6A:
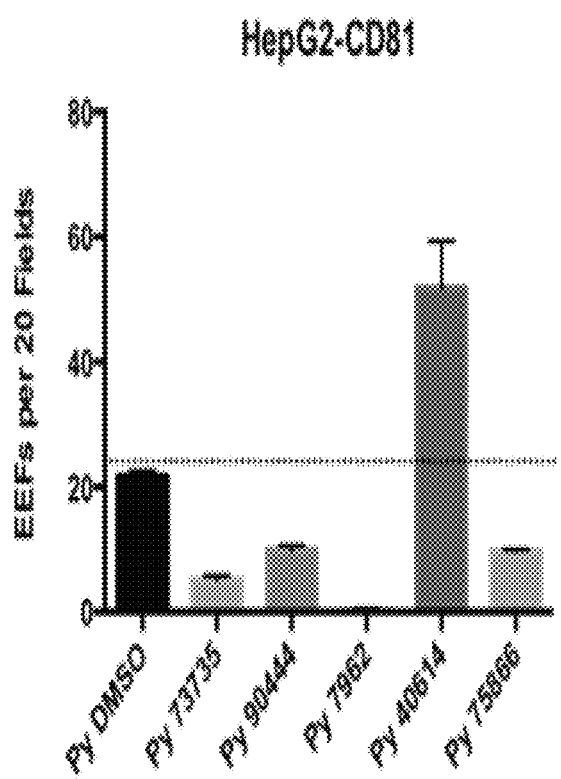
Figure 6B:
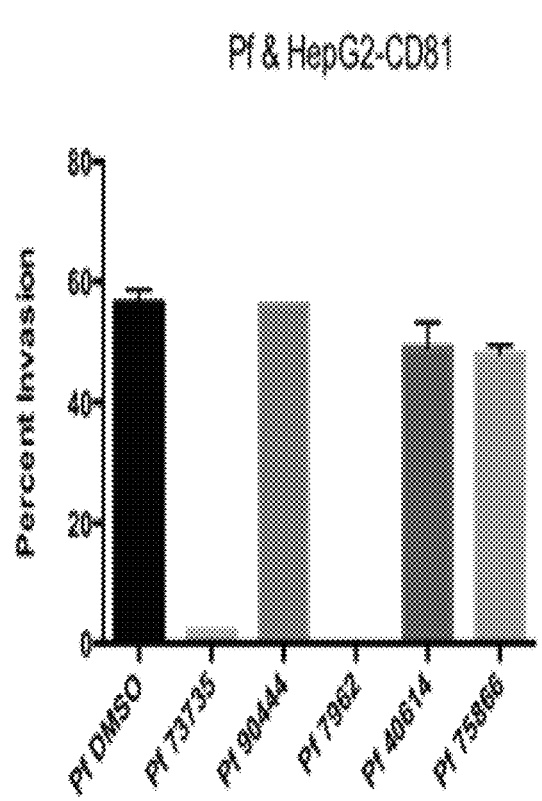
Figure 7A:
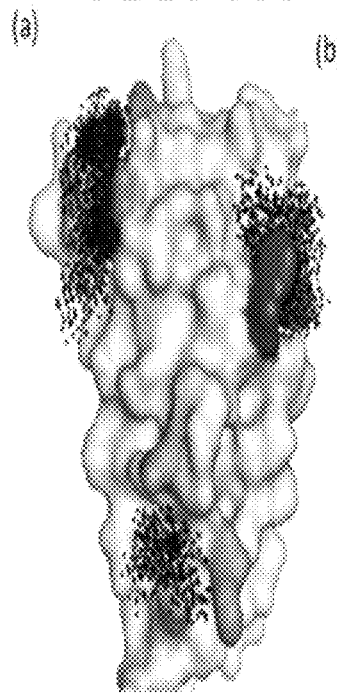
Figure 7B:
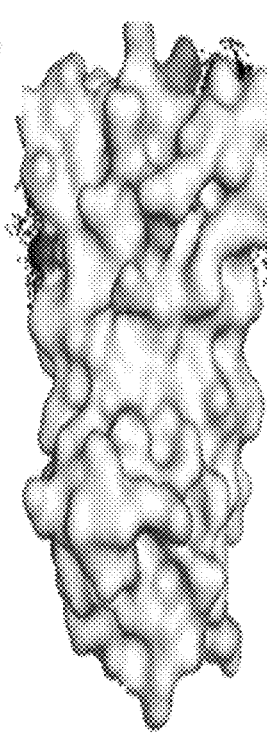
Figure 7C:
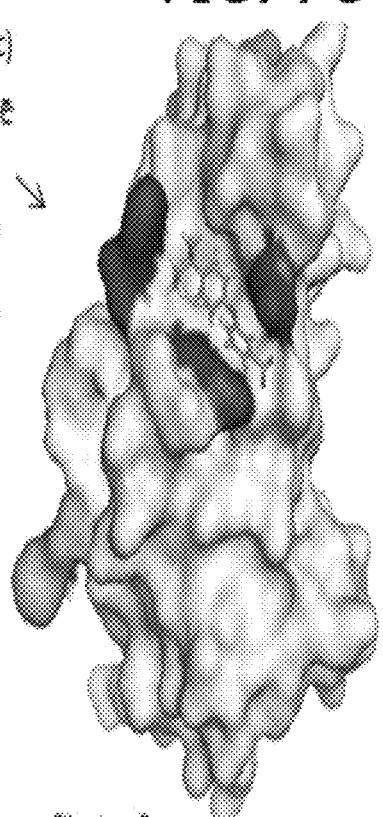
Figure 7D:
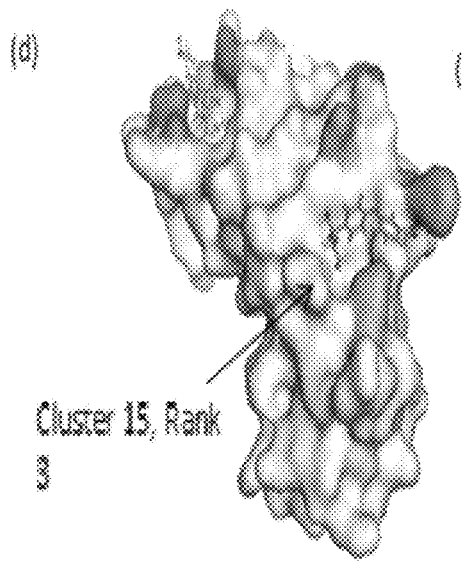
Figure 7E:
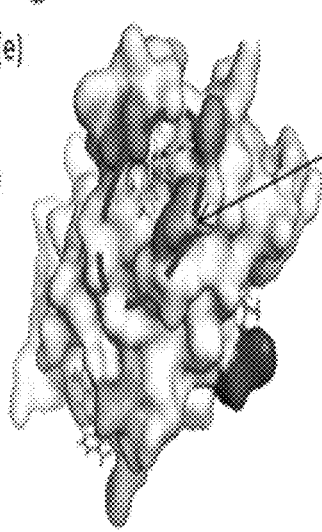
Figure 8A:
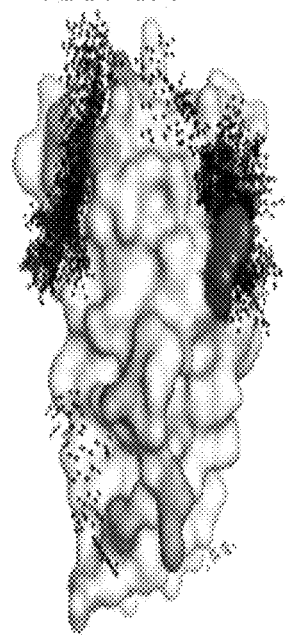
Figure 8B:
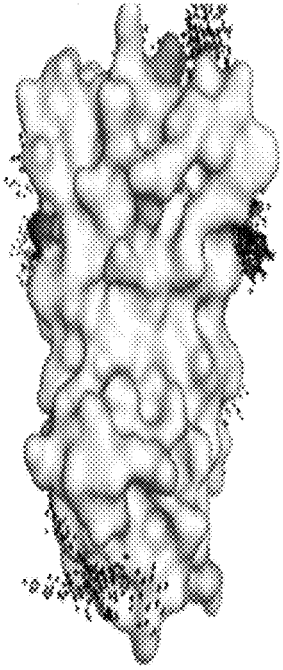
Figure 8C:
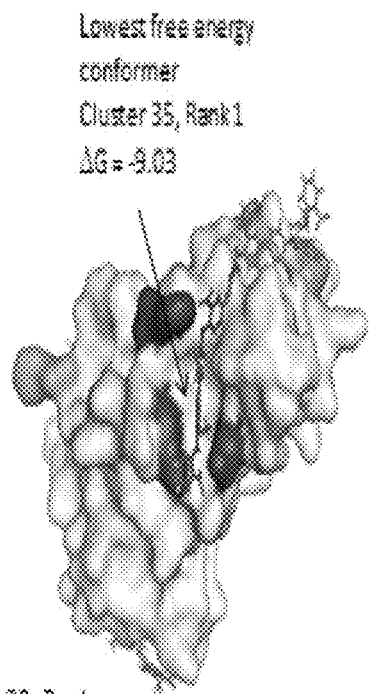
Figure 8D:
Figure 8E:
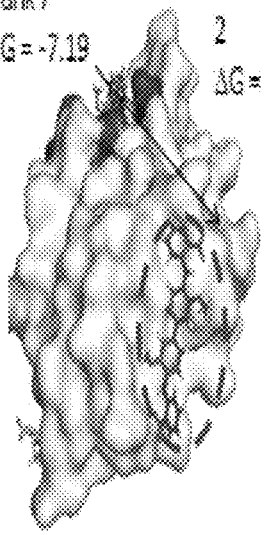
Figure 8F:

When sporozoite infection assays were conducted with the ligands, four ligands were found to inhibit *P. yoelii* (7962, 73735, 90444 and 75866) whereas ligand 40614 exhibited an interesting action where it enhanced the infection with *P. yoelii* (FIG. 4). Inhibition of *P. berghei* by both ligands 7962 and 73735 was detected when using Hep1-6 hepatoma cells whereas 90444 and 75866 didn't inhibit *P. yoelii* or *P. berghei* in Hep1-6 cells. Ligand 40614 was found to be consistent in enhancing development in both *P. yoelii* and *P. berghei* in both Hep1-6 and Hep2G cells (FIG. 5). As for the infection by *P. falciparum*, 7962 and 73735 were found to inhibit the infection with this species. On the other hand, 40614 wasn't found to enhance infection with *P. falciparum* (FIG. 6).

During in silica analysis of the binding modes of 7962 (the most promising drug lead among the five tested compounds), it was found that there are a number of 7962 conformations that interacted with the 21 amino acid sequence and Asp137 that were known to be important for malaria infection (FIG. 7).

As for 73735, some conformations interacted with the peptide sequence and others bound near Asp137 (FIG. 8).

The majority of 40614 ligand conformers did not interact with the peptide sequence or near Asp 137.

Only two 90444 ligand conformers were found to bind (weakly) nearby the peptide but not close to Asp137.

As for 75866, only a few 75866 ligand conformers were found to bind nearby the peptide sequence but none were found to bind near to Asp137.

Upon calculating the percentage of infection inhibition of the three *Plasmodium* species by the five ligands, 7962 was found to exhibit a 100% inhibition of all 3 species whereas 73735 was found to possess an inhibitory percentage of 96.8%, 77%, 61.7% and 82.3% of infection with *P. falciparum, P. yoelli* and *P. berghei* respectively.

TABLE 3

Percent Infection

| | Percent Infection | | | |
|---|---|---|---|---|
| | HepG2-CD81 | | Hepa1-6 Cells | |
| Ligand | Plasmodium falciparum | Plasmodium yoelii | Plasmodium yoelii | Plasmodium berghei |
| 73735 | 3.2 | 23 | 38.3 | 17.7 |
| 90444 | 98.7 | 44.3 | 222 | 95.6 |
| 7962 | 0 | 0 | 0 | 0 |
| 75866 | 84.2 | 42.6 | 122 | 135 |

Other Methods of Use. The ligands herein may be used as model ligands, prototypes, targets or starting points for designing additional ligands for CD81, The ligands described herein and their analogs or conjugates can also be used to obtain information that can be used. to design other ligands or ligand derivatives that bind to CD81 and are even better drug candidates. This can be accomplished by analyzing the compounds using a suite of computational methods and our medicinal chemistry insight.

One approach to analyze the compounds and find others that should bind to the same site and, potentially, have the same or better activities is called chemical similarity searching. In chemical similarity searching, each of the ligands, ligand analogs, and conjugates that block *Plasmodium* infection are broken down into its fragments (see example in FIG. 12) using a computer program, and each fragment is compared to a table of known pharmaceutically relevant molecular fragments (FIG. 13). This information is stored in the computer as a series of bits (0=No, 1=yes) that defines a chemical fingerprint for each ligand, ligand analog and conjugate. For the fragments shown in FIG. 13, the chemical fingerprint would be 0101011111.

This fingerprint is then compared to a large database of other chemical structures whose fingerprints have been defined to identify other structures in the database that have similar fingerprints. Two fingerprints are most commonly compared by determining the Tanimoto coefficient (SimT) where $SimT = C/(A+B-C)$ and:

C is the count of the identical bits set (ones) in both fingerprints. This is a count of the fragments common to both the query and comparison structure.

A is count of total bits set (ones) in fingerprint #1. This is a count of the fragments detected in the query.

B is count of bits set (ones) in fingerprint #2. This is a count of the fragments detected in the comparison structure.

Figure 12:
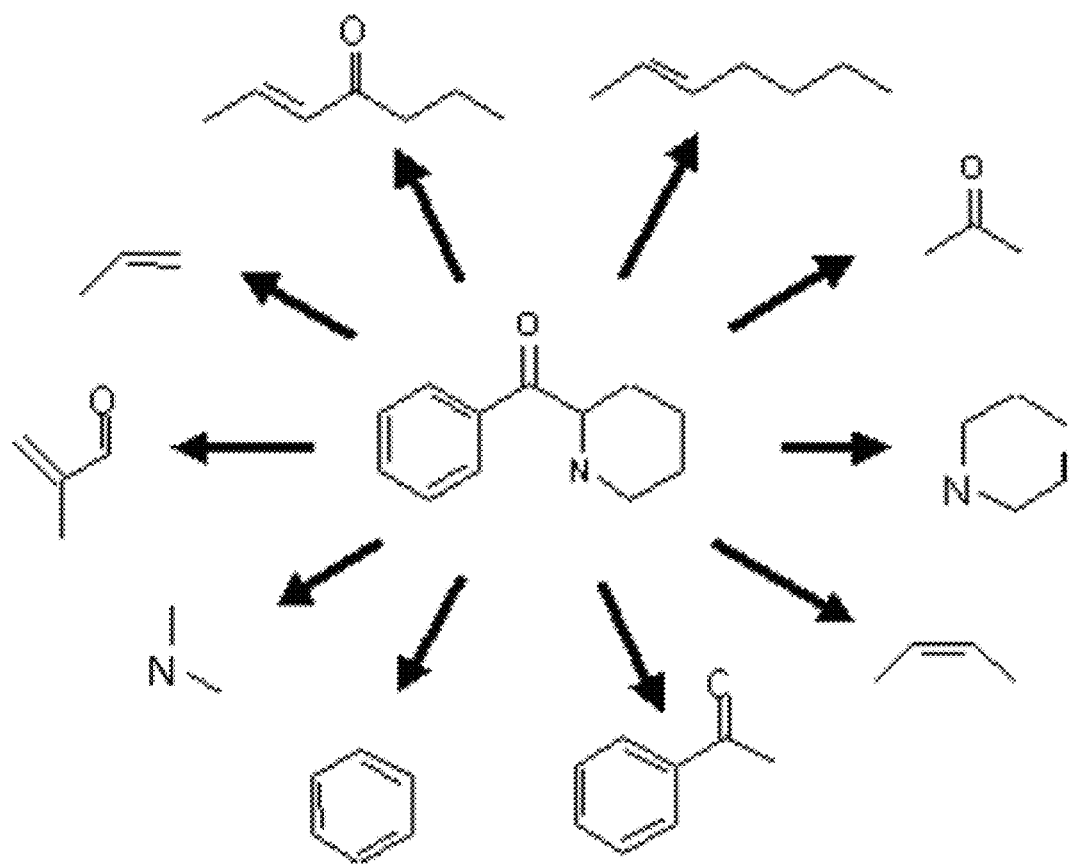

The Tanimoto coefficient will vary from one to zero. A value of zero indicates that no fragments were found to be common to both structures. A value of 1 (reported typically as 100% similarity) indicates that all bits set to one (all fragments detected) were also detected in the second structure and they are identical. A Tanimoto coefficient approaching 1 means two chemical structures are very similar. The lower the Tanimoto coefficient the more dissimilar two molecules are. FIG. 12 describes the use of model ligand fragments to determine this coefficient. FIG. 13 describes an example of small set of pharmaceutically relevant fragments used to compare to fragments of drug candidate ligand to calculate Tanimoto coefficient.

A second approach is to use the interactions of the ligand, its analogs and derivatives docked to CD81 along with a pharmacophore model to develop interaction based filters that are used to screen a database of molecules. Typical pharmacophore features include hydrophobic centroids, aromatic rings, hydrogen bond acceptors or donors, cations, and anions. The locations of the cationic, anionic and hydrophobic regions of a molecule can be calculated and displayed as an electrostatic potential. These pharmacophoric points may be located on the ligand itself or may be projected points presumed to be located in the receptor.

The features need to match different chemical groups with similar properties in order to identify novel ligands that are not simple analogs of the existing structure, Ligand-receptor interactions are typically "polar positive", "polar negative" or "hydrophobic". A well-defined pharmacophore model includes both hydrophobic volumes and hydrogen bond vectors.

The set of molecules that have the biological activity (e.g. inhibit *Plasmodium* infection) and a set of molecules that have been tested and shown to have no activity are used to generate the pharmacophore model. Conformational analyses are performed on the individual ligands and the lowest energy conformer is selected to be the bioactive conformation for each (unless x-ray diffraction or NMR data indicated otherwise). All the bioactive conformers of the different active ligands are superimposed and similar functional groups (phenyl rings, carboxyl or amino groups) or electrostatic potential are overlaid. The overlapped structures are used to generate an abstract representation of the molecule set in which pharmacophore elements like aromatic rings, hydrogen bond donors/acceptors, etc are designated. Once this pharmacophore model is developed (using those molecules that don't have bioactivity to rule out elements that are not relevant), it can be used to search new databases of molecules to identify new leads that have the same arrangement of pharmacophore elements.

Once a set of new compounds have been identified, these compounds are then evaluated to determine the feasibility of their synthesis by assessing their synthetic accessibility. This process involves the use of computational methods such as those described by Podolyan, et al. [21] or Ertl and Schuffenhauer [22]. Those compounds having the highest scores for synthetic accessibility are then synthesized and tested.

REFERENCES

1. Harper K, Annelagos G (2011). "The changing diseasescape in the third epidemiological transition". International Journal of Environmental Research and Public Health 7 (2): 675-97
2. Jarcho S. Malaria and murder (Joseph Jones, 1878). Bull N Y Acad Med 1968; 44: 759-60.
3. Jarcho S. Some observations on disease in prehistoric North America. Bull Hist Med 1964; 38:1-19.
4. "The Nobel Prize in Physiology or Medicine 1902: Ronald Ross". The Nobel Foundation, Retrieved 2012 May 14
5. Hawass Z, Gad Y Z, Ismail S, Khairat R, Fathalla D, Hasan N, et al. Ancestry and pathology in King Tutankhamun's family. JAMA 2010; 303:638-47.
6. Miller R L, Ikram S, Armelagos G J, Walker R, Harer W B, Shiff C J, et al. Diagnosis of *Plasmodium falciparum* infections in mummies using the rapid manual ParaSight-F test. Trans R Soc Trop Med Hyg 1994; 88:31-2.
7. Druilhe P, Daubersies P, Patarapotikul J, Gentil C, Chene L, Chongsuphajaisiddhi T, et al. A primary malarial infection is composed of a very wide range of genetically diverse but related parasites. J Clin Invest 1998;101:2008-16.
8. Prudencio M, Rodriguez A, Moat MM (2006) The silent path to thousands of merozoites: the *Plasmodium* liver stage. Nat Rev Microbiol 4: 849-856.
9. Silvie O, Rubinstein E, Franetich J F, Prenant M, Belnoue E, et al. (2003). Hepatocyte CD81 is required for *Plasmodium falciparum* and *Plasmodium yoelii* sporozoite infectivity. Nat Med 9: 93-96.
10. Silvie O, Greco C, Franetich J F, Dubart-Kupperschmitt A, Hannoun L, et al. (2006) Expression of human CD81 differently affects host cell susceptibility to malaria sporozoites depending on the *Plasmodium* species. Cell Microbiol 8:1134-1146.
11. Silvie O, Charrin S, Billard M, Franetich J F, Clark K L, et al. (2006) Cholesterol contributes to the organization of tetraspanin-enriched microdomains and to CD81-dependent infection by malaria sporozoites. J Cell Sci 119: 1992-2002.
12. Levy S, Shoham T (2005) The tetraspanin web modulates immune-signalling complexes. Nat Rev Immunol 5: 136-148.
13. Yalaoui S, Zougbédé S, Charrin S, Silvie O, Arduise C, et al, (2008) Hepatocyte Permissiveness to *Plasmodium* Infection Is Conveyed by a Short and Structurally. Conserved Region of the CD81 Large Extracellular Domain.PLoS Pathog 4(2).
14. Olivier Silvie, Céline Greco, Jean-François Franetich, Anne Dubart-Kupperschmitt, Laurent Hannoun, Geert-Jan van Gernert, Robert W. Sauerwein, Shoshana Levy, Claude Boucheix, Eric Rubinstein and Dominique Mazier. Expression of human CD81 differently affects host cell susceptibility to malaria sporozoites depending on the *Plasmodium* species, Cellular Microbiology 8:1134-46; 2006.
15. Tsuji M, Mattel D, Nussenzweig R S, Eichinger D and Zavala F. Demonstration of heat-shock protein 70 in the sporozoite stage of malaria parasites. Parasitol Res 80:16-21; 1994.
16. Levy, S.; Todd, S. C.; Maecker, H. T., CD81 (TAPA-1): a molecule involved in signal transduction and cell adhesion in the immune system. *Annu Rev immunol* 1998, 16, 89-109.
17. Petracca, R.; Falugi, F.; Galli, G.; Norais, N.; Rosa, D.; Campagnoli, S.; Burgio, V.; Di Stasio, E.; Giardina, B.; Houghton, M.; Abrignani, S.; Grandi, G., Structure-function analysis of hepatitis C virus envelope-CD81. binding. *J Virol* 2000, 74, (10), 4824-30.
18. Higginbottom, A.; Quinn, E R.; Kuo, C. C.; Flint, M.; Wilson, L. H.; Bianchi, E.; Nicosia, A.; Monk, P. N.; McKeating, J. A.; Levy, S., Identification of amino acid residues in CD81 critical for interaction with hepatitis C virus envelope glycoprotein E2. *J Viral* 2000, 74, (8), 3642-9.
19. Kitadokoro, K.; Bordo, D.; Galli, G.; Petracca, R.; Falugi, F.; Abrignani, S.; Grandi, G.; Bolognesi, M., CD81 extracellular domain 3D structure: insight into the tetraspanin superfamily structural motifs. *Embo J* 2001, 20, (1-2), 12-8.
20. Kitadokoro, K.; Galli, G.; Petracca, R.; Falugi, F.; Grandi, G.; Bolognesi, M., Crystallization and preliminary crystallographic studies on the large extracellular domain of human CD81, a tetraspanin receptor for hepatitis C virus. *Acta Crystallogr D Biol Crystallogr* 2001, 57, (Pt 1), 156-8.
21. Podolyan et al (Y. Podolyan, M. Walters, G. Karypis, J Chem Inform Modeling 50:979-991 [2010]
22. P. Ertl, A. Schuffenhauer, J Cheminformatics 1: 8 [2009] doi:10.1186/1758-2946-1-8.
23. Balhorn, R.; Hok, S.; Burke, P. A.; Lightstone, F. C.; Cosman, M.; Zemla, A.; Mirick, G.; Perkins, J.; Natarajan, A.; Corzett, M.; DeNardo, S. J.; Albrecht, H.; Gregg, J. P.; DeNardo, G. L., Selective high-affinity ligand antibody mimics for cancer diagnosis and therapy: initial application to lymphoma/leukemia. *Clin Cancer Res* 2007, 13, (18 Pt 2), 5621s-5628s.
24. DeNardo, G. L.; Hok, S.; Van Natarajan, A.; Cosman, M.; DeNardo, S. J.; Lightstone, F. C.; Mirick, G. R.; Yuan, A.; Perkins, J.; Sysko, V. V.; Lehmann, J.; Balhom, R. L., Characteristics of dimeric (bis) bidentate selective high affinity ligands as HLA-DR10 beta antibody mimics targeting non-Hodgkin's lymphoma. *Int J Oncol* 2007, 31, (4), 729-40.
25. AutoDock website: http://autodock.scripps.edu
26. Morris, G. M.; Goodsell D. S.; Halliday R. S.; Huey R.; Hart W. E.; Belew R. K.; Olson A. K., Automated docking using a Lamarckian genetic algorithm and an empirical binding free energy function *J. Comput. Chem,* 1998, 19, 1639-1662.
27. Huey, R.; Morris, G. M.; Olson, A. J.; Goodsell, D, S., A semiempirical free energy force field with charge-based desolvation, J Comput Chem 2007, 28, (6), 1145-52.
28. Huey R.; Goodsell D. S.; Morris G. M.; Olson A. J., Grid-based hydrogen bond potentials with improved directionality. *Letters in Drug Design and Discovery* 2004, 1, 178-183.
29. Harris, R; Olson, A. J.; Goodsell, D. S., Automated prediction of ligand-binding sites in proteins. *Proteins* 2008, 70, (4), 1506-17.
30. Morris, G. M., Huey, R., Olson, A., Using AutoDock for Ligand-Receptor Docking. *Current Protocols in Bioinformatics Chapter* 8 2008, Unit 8.14.
31. NBCR website: https://www.nbcr.net/pub/wiki/index.php?title=CADD Pipeline
32. Sanner, M. F., Python: a programming language for software integration and development. *J Mol Graph Model* 1999, 17, (1), 57-61.
33. Holzer, M.; Ziegler, S.; Neugebauer, A.; Kronenberger, B.; Klein, C, D.; Hartmann, R. W., Structural modifications of salicylates: inhibitors of human CD81-receptor HCV-E2 interaction. *Arch Pharm* (*Weinheim*) 2008, 341, (8), 478-84.

The invention claimed is:

1. A method for treating a subject exposed to, or at risk of exposure to, a *Plasmodium* parasite comprising administering a ligand conjugate comprising at least two ligands for CD81 selected from the group consisting of 73735, 90444, 7962 and 7586 (NCI diversity set ligand numbers); wherein structures of 73735, 90444, 7962 and 75866 are given by the following chemical structures:

73735

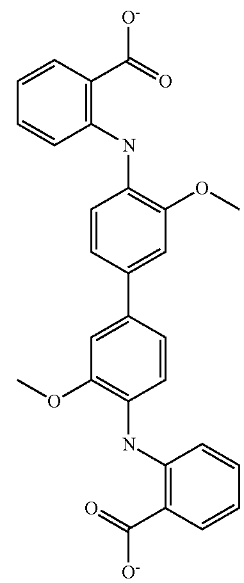

,

90444

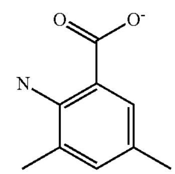

,

7962

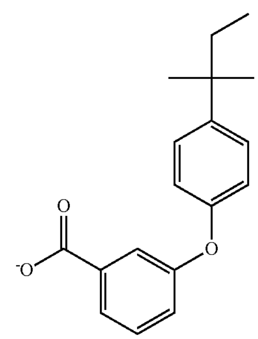

, and

75866

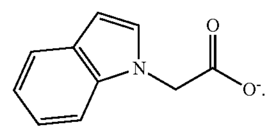

.

2. The method of claim 1, wherein said *Plasmodium* parasite is *Plasmodium falciparum.*

3. The method of claim 1, wherein said *Plasmodium* parasite is *Plasmodium vivax, Plasmodium malariae, Plasmodium ovale, Plasmodium knowlesi*, or other *Plasmodium* species that infects humans.

4. The method of claim 1, wherein said is a covalent conjugate of at least two ligands selected from the group consisting of 73735, 90444, 7962 or 75866 (NCI diversity set ligand numbers).

5. The method of claim 1, wherein the ligand conjugate is a covalent conjugate of 7962 and 73735.

6. The method of claim 1, wherein the ligand conjugate is a covalent conjugate of 7962 and 73735 that comprises the following chemical structure:

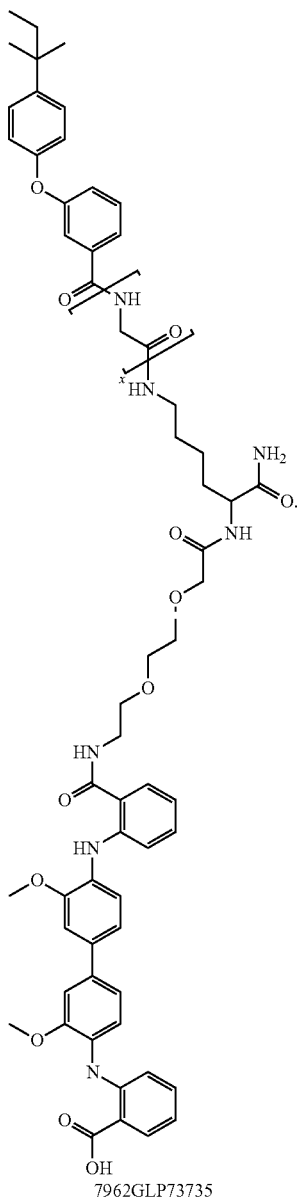

7962GLP73735

7. The method of claim 1, wherein said ligand conjugate is a ligand conjugate comprising at least two of 73735, 90444, 7962 or 75866 (NCI diversity set ligand numbers) covalently-linked to another ligand for CD81.

8. The method of claim 1, wherein said ligand conjugate is a ligand conjugate comprising two of said ligands that are linked via their carboxy or amino groups and an intervening linker comprising lysine, dimethylaminomethane, and/or PEG linker(s).

9. The method of claim 1, wherein said ligand conjugate is a ligand conjugate of two of said ligands directly linked via their carboxy or amino groups; or via their carboxy or amino groups by intervening diaminoalkane or dicarboxylic acid groups.

10. The method of claim 1, wherein said ligand conjugate is a ligand conjugate of two of said ligands linked via a single position on a first ligand to a single position on a second ligand, wherein said single position is a carboxy or amino group.

11. The method of claim 1, wherein said ligand conjugate is a ligand conjugate comprising two of said ligands linked via a chain of no more than 10 atoms.

12. The method of claim 1, wherein said ligand conjugate is a ligand conjugate comprising 7962 covalently-linked to 73735.

13. A composition comprising a covalently-linked ligand conjugate of at least two of 73735, 90444, 7962 or 75866 and a pharmaceutically acceptable carrier.

14. The composition of claim 13, wherein the ligand conjugate comprises 7962 and 73735.

15. The composition of claim 13 wherein the a ligand conjugate is selected from the group consisting of 7962GP73735a7962a90444, 7962GLP73735, 7962GL75866, 7962L73735GL73735, 7962GP73735, 7962GP73735a7962, 73735L73735, 73735a73735, 73735a7962a90444, 75866LP73735, 73735Pdam75866LG7962, 73735Pdam75866LG40614, 75866L7962, 75866LP73735, 73735L73735, and 7962LPG7962.

16. The method of claim 1, wherein said ligand conjugate is at least one selected from the group consisting of 7962GP73735a7962a90444, 7962GLP73735, 7962GL75866, 7962L73735GL73735, 7962GP73735, 7962GP73735a7962, 73735L73735, 73735a73735, 73735a7962a90444, 75866LP73735, 73735Pdam75866LG7962, 73735Pdam75866LG40614, 75866L7962, 75866LP73735, 73735L73735, and 7962LPG7962.

17. The method of claim 1, wherein the subject is infected with *Plasmodium*.

18. The method of claim 1, wherein the subject is at risk of exposure to *Plasmodium*.

* * * * *